(12) United States Patent
Pulst et al.

(10) Patent No.: US 7,927,786 B2
(45) Date of Patent: Apr. 19, 2011

(54) PARKIN INTERACTING POLYPEPTIDES AND METHODS OF USE

(75) Inventors: Stefan M. Pulst, Los Angeles, CA (US); Duong P. Huynh, Long Beach, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 953 days.

(21) Appl. No.: 10/782,375

(22) Filed: Feb. 18, 2004

(65) Prior Publication Data

US 2008/0301824 A1 Dec. 4, 2008

Related U.S. Application Data

(60) Provisional application No. 60/448,252, filed on Feb. 18, 2003.

(51) Int. Cl.
*C12Q 1/00* (2006.01)
*G01N 33/53* (2006.01)

(52) U.S. Cl. ............................................ 435/4; 435/7.1
(58) Field of Classification Search ........................ None
See application file for complete search history.

(56) References Cited

U.S. PATENT DOCUMENTS

2002/0155577 A1  10/2002  Koutnikova

FOREIGN PATENT DOCUMENTS

WO    WO 02/24721    3/2002

OTHER PUBLICATIONS

Abbas et al.,"A wide variety of mutations in the parkin gene are responsible for autosomal recessive parkinsonism in Europe. French Parkinson's Disease Genetics Study Group and the European Consortium on Genetic Susceptibility in Parkinson's Disease," *Hum. Mol. Genet.* 8:567-574 (1999).
Beites et al., "The septin CDCrel-1 binds syntaxin and inhibits exocytosis," *Nat. Neurosci.* 2(5):434-439 (1999).
Berton et al., "Synaptotagmin I and IV define distinct populations of neuronal transport vesicles," *Eur. J. Neurosci.* 12:1294-1302 (2000).
Bommert et al., "Inhibition of neurotransmitter release by C2-domain peptides implicates synaptotagmin in exocytosis," *Nature* 363:163-165 (1993).
Bonifati et al., "Mutations in the DJ-1 gene associated with autosomal recessive early-onset parkinsonism," *Science* 299:256-259 (2003).
Chung et al., "Parkin ubiquitinates the alpha-synuclein-interacting protein, synphilin-1: implications for Lewy-body formation in Parkinson disease," *Nat. Med.* 7:1144-1150 (2001).
Corti et al., "The p38 subunit of the aminoacyl-tRNA synthetase complex is a Parkin substrate: linking protein biosynthesis and neurodegeneration," *Hum Mol. Genet.* 12:1427-1437 (2003).
Damier et al., "The substantia nigra of the human brain. II. Patterns of loss of dopamine-containing neurons in Parkinson's disease," *Brain* 122:1437-1448 (1999).

Davis et al., "Kinetics of synaptotagmin responses to Ca2+ and assembly with the core Snare complex onto membranes," *Neuron.* 24:363-376 (1999).
Diantonio et al., "The effect on synaptic physiology of synaptotagmin mutations in Drosophila," *Neuron.* 12:909-920 (1993).
Diantonio et al., "Synaptic transmission persists in synaptotagmin mutants of Drosophila," *Cell* 73:1281-1290 (1993).
Elferink et al., "A role for synaptotagmin (p65) in regulated exocytosis," *Cell* 72:153-159 (1993).
Engelender et al., "Synphilin-1 associates with alpha-synuclein and promotes the formation of cytosolic inclusions," *Nat. Genet.* 22:110-114 (1999).
Fernandez-Chacon et al., "Synaptotagmin I functions as a calcium regulator of release probability," *Nature* 410:41-49 (2001).
Finney et al., "The cellular protein level of parkin is regulated by its ubiquitin-like domain," *J. Biol. Chem.* 278:16054-16058 (2003).
Fukuda and Mikoshiba, "Characterization of KIAA1427 protein as an atypical synaptotagmin (Syt XIII)," *Biochem. J.* 354:249-257 (2001).
Fukuda et al., "A unique spacer domain of synaptotagmin IV is essential for Golgi localization," *J. Neurochem.* 77:730-740 (2001).
Fukuda et al., "Nerve growth factor-dependent sorting of synaptotagmin IV protein to mature dense-core vesicles that undergo calcium-dependent exocytosis in PC12 cells," *J. Biol. Chem.* 278:3220-3226 (2003).
Geppert et al., "Synaptotagmin I: a major Ca2+ sensor for transmitter release at a central synapse," *Cell* 79(4):717-727 (1994).
Gerona et al., "The C terminus of SNAP25 is essential for Ca2+-dependent binding of synaptotagmin to SNARE complexes," *J. Biol. Chem.* 275:6328-6336 (2000).
Hayashi et al., "An autopsy case of autosomal-recessive juvenile parkinsonism with a homozygous exon 4 deletion in the parkin gene," *Mov. Disord.* 15:884-888 (2000).
Huynh et al., "Parkin is associated with actin filaments in neuronal and nonneuronal cells," *Ann. Neurol.* 48:737-744 (2000).
Huynh et al., "Parkin colocalizes with actin filaments and synaptic vesicles, and interacts with synaptotagmin XI," *Abstr. Soc. Neurosci.* 27:607, abstract 233.1, (2001).
Huynh et al., "Interaction of Parkin with vesicle-associated proteins," *Neurology* 58 (suppl. 3); A410 abstract S53.007 (2002).

(Continued)

*Primary Examiner* — Jeffrey Stucker
*Assistant Examiner* — Stephen Gucker
(74) *Attorney, Agent, or Firm* — McDermott Will & Emery LLP

(57) ABSTRACT

The invention provides parkin binding polypeptides and encoding nucleic acids. The invention also provides antibodies specific for the parkin binding polypeptides. The invention additionally provides methods of detecting a parkin binding polypeptide and detecting a nucleic acid encoding a parkin binding polypeptide. The invention further provides methods of using a parkin binding polypeptide. In one embodiment, the invention provides a method of identifying a candidate drug for treating Parkinson's disease by contacting a parkin binding polypeptide with one or more compounds and identifying a compound that alters the activity of the parkin binding polypeptide.

4 Claims, 26 Drawing Sheets

OTHER PUBLICATIONS

Huynh et al., "The autosomal recessive juvenile Parkinson disease gene product, parkin, interacts with and ubiquitinates synaptotagmin XI," *Hum. Mol. Genet*.12(20):2587-2597 (2003).

Ibata et al., "Synaptotagmin IV is present at the golgi and distal parts of neuritis," *J. Neurochem*. 74:518-526 (2000).

Imai et al., "An unfolded putative transmembrane polypeptide, which can lead to endoplasmic reticulum stress, is a substrate of Parkin," *Cell* 105:891-902 (2001).

Imai et al., "CHIP is associated with Parkin, a gene responsible for familial Parkinson's disease, and enhances its ubiquitin ligase activity," *Mol. Cell*. 10:55-67 (2002).

Imai et al., "Parkin suppresses unfolded protein stress-induced cell death through its E3 ubiquitin-protein ligase activity," *J. Biol. Chem*. 275:35661-35664 (2000).

Ishikawa and Takahashi, "Clinical and neuropathological aspects of autosomal recessive juvenile parkinsonism," *J. Neurol*. 245(Suppl 3): p. 4-p. 9 (1998).

Ishikawa and Tsuji, "Clinical analysis of 17 patients in 12 Japanese families with autosomal-recessive type juvenile parkinsonism," *Neurology* 47:160-166 (1996).

Joazeiro and Weissman, "RING finger proteins: mediators of ubiquitin ligase activity," *Cell* 102:549-552 (2000).

Jorgensen et al., "Defective recycling of synaptic vesicles in synaptotagmin mutants of Caenorhabditis elegans," *Nature* 378:196-199 (1995).

Kitada et al., "Mutations in the parkin gene cause autosomal recessive juvenile parkinsonism," *Nature* 392:605-608 (1998).

Le et al., "Mutations in NR4A2 associated with familial Parkinson 33:85-89 (2003). disease," Nat. Genet. 33:85-89 (2003).

Leveque et al., "Calcium-dependent dissociation of synaptotagmin from synaptic SNARE complexes," *J. Neurochem*. 74:367-374 (2000).

Li et al., "$Ca^{2+}$-dependent and -independent activities of neural and non-neural synaptotagmins," *Nature* 375:594-599 (1995).

Matsumine, "A loss-of-function mechanism of nigral neuron death without Lewy body formation: autosomal recessive juvenile parkinsonism (AR-JP)," *J. Neurol*. 245(Suppl. 3):10-14 (1998).

Mori et al., "Pathologic and biochemical studies of juvenile parkinsonism linked to chromosome 6q," *Neurology* 51:890-892 (1998).

Murphey and Godenschwege, "New roles for ubiquitin in the assembly and function of neuronal circuits," *Neuron* 36:5-8 (2002).

Naoi et al., "Cell death of dopamine neurons in aging and Parkinson's disease," *Mech. Ageing Dev*. 111:175-188 (1999).

Polymeropoulos et al., "Mutation in the alpha-synuclein gene identified in families with Parkinson's disease," *Science* 276:2045-2047 (1997).

Reist et al., "Morphologically docked synaptic vesicles are reduced in synaptotagmin mutants of Drosophila," *J. Neurosci*. 18:7662-7673 (1998).

Ren et al., "Parkin binds to alpha/beta tubulin and increases their ubiquitination and degradation," *J. Neurosci*. 23:3316-3324 (2003).

Ribeiro et al., "Synphilin-1 is developmentally localized to synaptic terminals, and its association with synaptic vesicles is modulated by alpha-synuclein," *J. Biol. Chem*. 277:23927-23933 (2002).

Schiavo et al., "Binding of the synaptic vesicle v-SNARE, synaptotagmin, to the plasma membrane t-SNARE, SNAP-25, can explain docked vesicles at neurotoxin-treated synapses," *Proc. Natl. Acad. Sci. USA* 94:997-1001 (1997).

Schlossmacher et al., "Parkin localizes to the Lewy bodies of Parkinson disease and dementia with Lewy bodies," *Am. J. Pathol*. 160:1655-1667 (2002).

Scoles et al., "Neurofibromatosis 2 tumour suppressor schwannomin interacts with betaII-spectrin," *Nat. Genet*. 18:354-359 (1998).

Shibata et al., "A novel protein with RNA-binding motifs interacts with ataxin-2," *Hum. Mol. Genet*. 9:1303-1313 (2000).

Shimura et al., "Familial Parkinson disease gene product, parkin, is a ubiquitin-protein ligase," *Nat. Genet*. 25:302-305 (2000).

Shimura et al., "Immunohistochemical and subcellular localization of Parkin protein: absence of protein in autosomal recessive juvenile parkinsonism patients," *Ann. Neurol*. 45:668-672 (1999).

Shimura et al., "Ubiquitination of a new form of alpha-synuclein by parkin from human brain: implications for Parkinson's disease," *Science* 293(5528):263-269 (2001).

Staropoli et al., "Parkin is a component of an SCF-like ubiquitin ligase complex and protects postmitotic neurons from kainate excitotoxicity," *Neuron* 37:735-749 (2003).

Sudhof, "Synaptotagmins: why so many?," *J. Biol. Chem*. 277(10):7629-7632 (2001).

Tsai et al., "Parkin facilitates the elimination of expanded polyglutamine proteins and leads to preservation of proteasome function," *J. Biol. Chem*. 278:22044-22055 (2003).

Van De Warrenburg et al., "Clinical and pathologic abnormalities in a family with parkinsonism and parkin gene mutations," *Neurology* 56:555-557 (2001).

Voets et al., "Intracellular calcium dependence of large dense-core vesicle exocytosis in the absence of synaptotagmin I," *Proc. Natl. Acad. Sci. USA* 98:11680-11685 (2001).

Von Poser et al., "The evolutionary pressure to inactivate. A subclass of synaptotagmins with an amino acid substitution that abolishes $Ca^{2+}$binding," *J. Biol. Chem*. 272:14314-14319 (1997).

Wakabayashi et al., "Immunocytochemical localization of synphilin-1, an alpha-synuclein-associated protein, in neurodegenerative disorders," *Acta Neuropathol* 103(3):209-214 (2002).

Wakabayashi et al., "Synphilin-1 is present in Lewy bodies in Parkinson's disease," *Ann. Neurol*. 47:521-523 (2000).

Wang et al., "Synaptotagmin modulation of fusion pore kinetics in regulated exocytosis of dense-core vesicles," *Science* 294:1111-1115 (2001).

Wintermeyer et al., "Mutation analysis and association studies of the UCHL1 gene in German Parkinson's disease patients," *Neuroreport* 11:2079-2082 (2000).

Yamada et al., "Relative sparing in Parkinson's disease of substantia nigra dopamine neurons containing calbindin-$_{D28K}$," *Brain Res*. 526:303-307 (1990).

Zhang et al., "Parkin functions as an E2-dependent ubiquitin-protein ligase and promotes the degradation of the synaptic vesicle-associated protein, CDCrel-1," *Proc. Natl. Acad. Sci. USA* 97:13354-13359 (2000).

Zhang et al., "Synaptotagmin I is a high affinity receptor for clathrin AP-2: implications for membrane recycling," *Cell* 78:751-760 (1994).

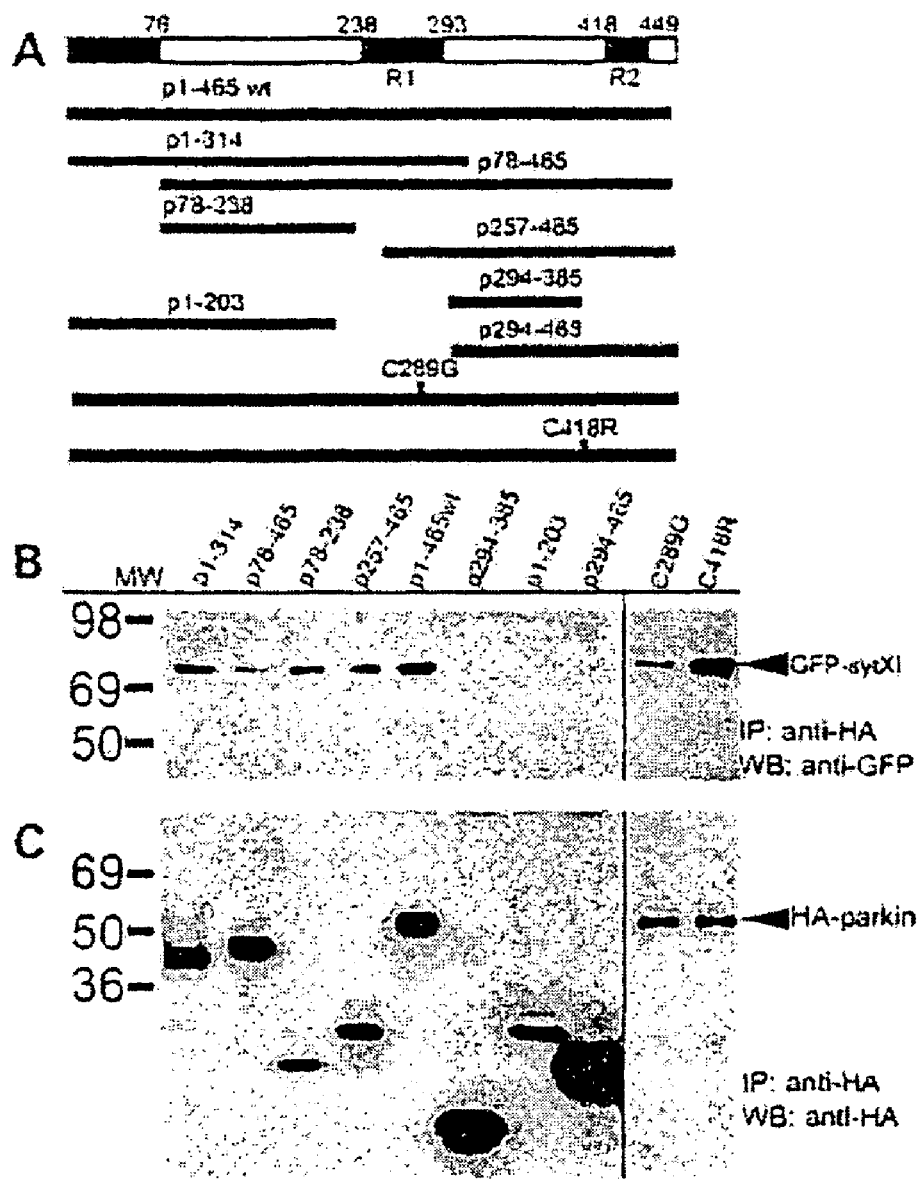
Figures 3A-C

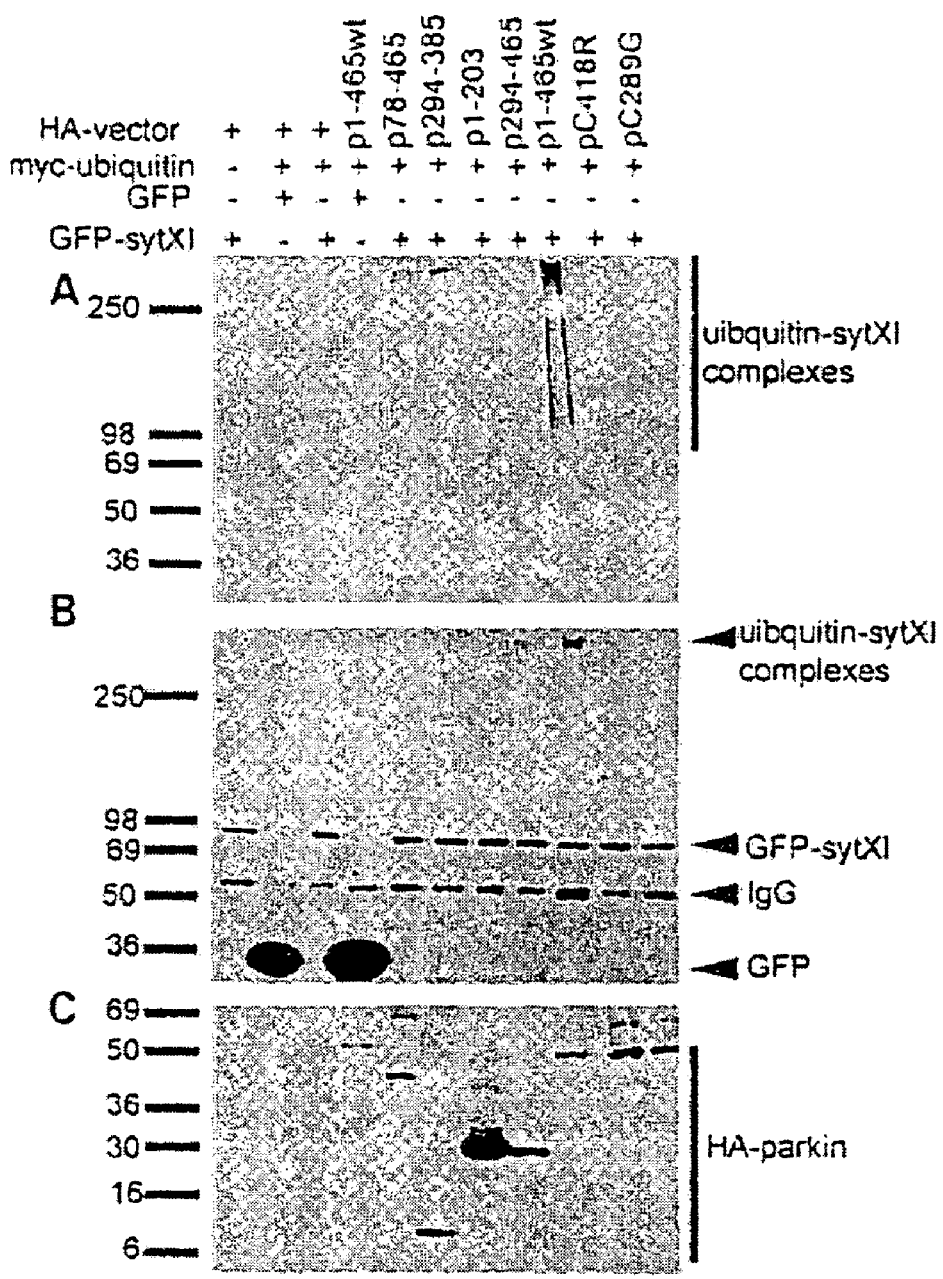
Figures 4A-C

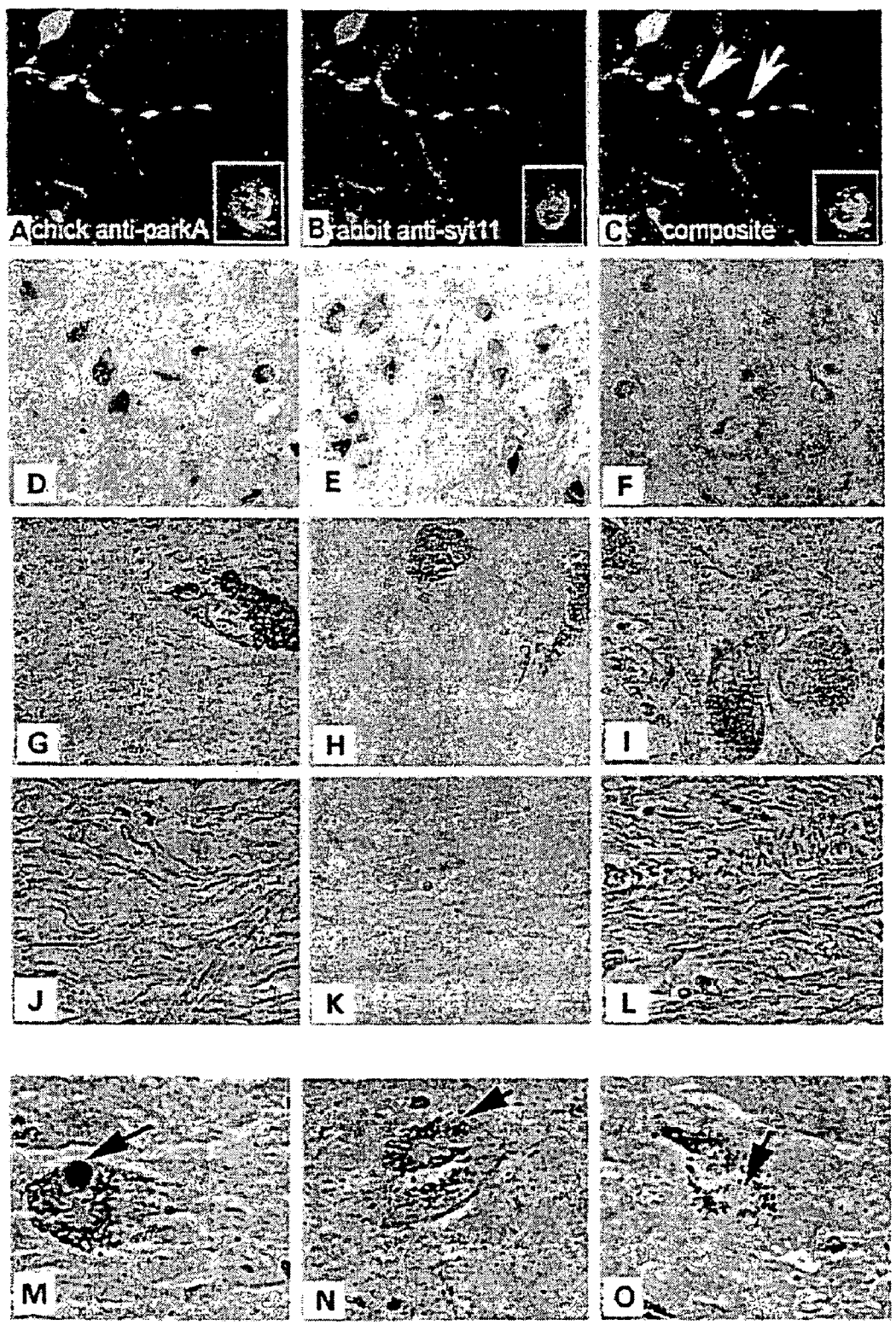
Figures 6A-O

P  Q  R

```
      agtcctcaacgaggggtccagtgtaggcagtgacaggcacatagctgttgagctcagcga
  1   ---------+---------+---------+---------+---------+---------+   60
      tcaggagttgctccccaggtcacatccgtcactgtccgtgtatcgacaactcgagtcgct ggcggggctgtgatacctcggcccggttttaccgatgtcctcctcccgcaggtagaact
 61   ---------+---------+---------+---------+---------+---------+  120
      ccgccccgacactatggagccgggccaaaaatggctacaggaggagggcgtccatcttga gggaggaaagatcagcccactgggcagtgccctggtcatgtagggtaacagccttgaccc
121   ---------+---------+---------+---------+---------+---------+  180
      ccctcctttctagtcgggtgacccgtcacgggaccagtacatcccattgtcggaactggg caccaaggatgatgttcttagcgatctccacgcccaggccccgcaggcctgataccagga
181   ---------+---------+---------+---------+---------+---------+  240
      gtggttcctactacaagaatcgctagaggtgcgggtccggggcgtccggactatggtcct cactggatgtctggagccgcttcattgcctcATGGCCCAACACATACAGCTGCCGGGAGT
241   ---------+---------+---------+---------+---------+---------+  300
      gtgacctacagacctcggcgaagtaacggagTACCGGGTTGTGTATGTCGACGGCCCTCA
                                     M  A  Q  H  I  Q  L  P  G  V AAAGGCCCTCGTCTATGTCTGCTTCACTGCCGTTCTTGGCCATTCCGTTGGTTGGCACCG
301   ---------+---------+---------+---------+---------+---------+  360
      TTTCCGGGAGCAGATACAGACGAAGTGACGGCAAGAACCGGTAAGGCAACCAACCGTGGC
       K  A  L  V  Y  V  C  F  T  A  V  L  G  H  S  V  G  W  H  R AGGGCACTTCGGACAACACGGACTGGGCAGGGGAGCAGTTAGAACCCGGCTTTGGATCAG
361   ---------+---------+---------+---------+---------+---------+  420
      TCCCGTGAAGCCTGTTGTGCCTGACCCGTCCCCTCGTCAATCTTGGGCCGAAACCTAGTC
       G  H  F  G  Q  H  G  L  G  R  G  A  V  R  T  R  L  W  I  R GCCCGGACACGCGACGTTTCTTGGACAGCGGCGAGCTGGACATCAATGCCGGTTCCCCGG
421   ---------+---------+---------+---------+---------+---------+  480
      CGGGCCTGTGCGCTGCAAAGAACCTGTCGCCGCTCGACCTGTAGTTACGGCCAAGGGGCC
       P  G  H  A  T  F  L  G  Q  R  R  A  G  H  Q  C  R  F  P  G GTCGCGCCGCCGCCAACTCCTCAAGGAGCCGAAGCCAAGCCCGGCCGCACCCTCCTCCTT
481   ---------+---------+---------+---------+---------+---------+  540
      CAGCGCGGCGGCGGTTGAGGAGTTCCTCGGCTTCGGTTCGGGCCGGCGTGGGAGGAGGAA
       S  R  R  R  Q  L  L  K  E  P  K  P  S  P  A  A  P  S  S  F CTCCTCCTCCCCGCCGCCTGGGCCGCCTAGAATCGCCGCTGCCGCCTTCTCCTCCCCCGG
541   ---------+---------+---------+---------+---------+---------+  600
      GAGGAGGAGGGGCGGCGGACCCGGCGGATCTTAGCGGCGACGGCGGAAGAGGAGGGGGCC
       S  S  S  P  P  P  G  P  P  R  I  A  A  A  A  F  S  S  P  G

CCGTTGTGGTTGTGGTTGTCCCTGCCACCTCCTTACAGCCGAGCCGCCGACACAAGATGG
```

FIGURE 8A

```
601  ----------+---------+---------+---------+---------+---------+  660
     GGCAACACCAACACCAACAGGGACGGTGGAGGAATGTCGGCTCGGCGGCTGTGTTCTACC
      R  C  G  C  G  C  P  C  H  L  L  T  A  E  P  P  T  Q  D  G

CGGACGCTtGAGCCTGGGGCCGGAACAAAACCTTGGGCCCCACCCCCAGAAACCCGGATG
661  ----------+---------+---------+---------+---------+---------+  720
     GCCTGCGAaCTCGGACCCCGGCCTTGTTTTGGAACCCGGGGTGGGGGTCTTTGGGCCTAC
      G  R  L  S  L  G  P  E  Q  N  L  G  P  H  P  Q  K  P  G  C

CAAGCGGGCCGCGCCTACTTATGAATCATGCATAAAGTTCCCTACTCGGTTGCGATTCAT
721  ----------+---------+---------+---------+---------+---------+  780
     GTTCGCCCGGCGCGGATGAATACTTAGTACGTATTTCAAGGGATGAGCCAACGCTAAGTA
      K  R  A  A  P  T  Y  E  S  C  I  K  F  P  T  R  L  R  F  I

TCGGTTAGAAGTGGAACAGCACCACCTGGTGGACATTGTGGCAGTAACAACGAAAACAGG
781  ----------+---------+---------+---------+---------+---------+  840
     AGCCAATCTTCACCTTGTCGTGGTGGACCACCTGTAACACCGTCATTGTTGCTTTTGTCC
      R  L  E  V  E  Q  H  H  L  V  D  I  V  A  V  T  T  K  T  G

TaAAACAGAgCCCACGCCTCATGGAATGCGACTAATGAATGAATTGTTGCAGCCAGGCTG
841  ----------+---------+---------+---------+---------+---------+  900
     AtTTTGTCTcCGGTGCGGAGTACCTTACGCTGATTACTTACTTAACAACGTCGGTCCGAC
      K  T  E  A  T  P  H  G  M  R  L  M  N  E  L  L  Q  P  G  C

TCAAGGAAGCGAAgAAAAACCGTTAAGGCCATGCTTCCTGATTATAAGTTATGCATGAAG
901  ----------+---------+---------+---------+---------+---------+  960
     AGTTCCTTCGCTTcTTTTTGGCAATTCCGGTACGAAGGACTAATATTCAATACGTACTTC
      Q  G  S  E  E  K  P  L  R  P  C  F  L  I  I  S  Y  A  *

TTGAGTGGTTGGTAGCAACAACCAGCAACCAGAAAGCAGATGTTAAAACATGGAAGCCAC
961  ----------+---------+---------+---------+---------+---------+  1020
     AACTCACCAACCATCGTTGTTGGTCGTTGGTCTTTCGTCTACAATTTTGTACCTTCGGTG

ACACCCCCATTCATGAATNAATGATGATCTTGCAGGGGCCCGGAAGCCAAGGAGACCCAG
1021 ----------+---------+---------+---------+---------+---------+  1080
     TGTGGGGGTAAGTACTTANTTACTACTAGAACGTCCCCGGGCCTTCGGTTCCTCTGGGTC

GCCACAACTTACTTCATGAATAATGCATGAGGCCCAGTGGGTTGGAATAAAAGGGGCACG
1081 ----------+---------+---------+---------+---------+---------+  1140
     CGGTGTTGAATGAAGTACTTATTACGTACTCCGGGTCACCCAACCTTATTTTCCCCGTGC

CCCGCCTATTGCTGCATCTAATACACTGTAAGCAGGGAAATGGGGCTGCTGCAGGGAAAA
1141 ----------+---------+---------+---------+---------+---------+  1200
     GGGCGGATAACGACGTAGATTATGTGACATTCGTCCCTTTACCCCGACGACGTCCCTTTT

CACACTCTCCCAGGTCCTGAATAATGAATTATGCTGCTGCAGTAGCTCAACCTGGAAACT
```

FIGURE 8A CONTINUED

```
1201  ---------+---------+---------+---------+---------+---------+  1260
      GTGTGAGAGGGTCCAGGACTTATTACTTAATACGACGACGTCATCGAGTTGGACCTTTGA

CAGAGAGGTCAAGAAAGGTTCCACCCAATTTATGAATTATGCATAAGGCGAAGAAACACC
1261  ---------+---------+---------+---------+---------+---------+  1320
      GTCTCTCCAGTTCTTTCCAAGGTGGGTTAAATACTTAATACGTATTCCGCTTCTTTGTGG

CAAGACTGCCCTGCCCCTCATTTACATAAATATTATACTAGCATTTACCATCTCACTTCT
1321  ---------+---------+---------+---------+---------+---------+  1380
      GTTCTGACGGGACGGGGAGTAAATGTATTTATAATATGATCGTAAATGGTAGAGTGAAGA

AGGAATACTAGTATATCGCTCACACCTCATATCCTCCCTACTATGCCTAGAAGGAATAAT
1381  ---------+---------+---------+---------+---------+---------+  1440
      TCCTTATGATCATATAGCGAGTGTGGAGTATAGGAGGGATGATACGGATCTTCCTTATTA

ACTATCGCTGTCG
1441  ---------+---  1453
      TGATAGCGACAGC
```

FIGURE 8A CONTINUED gaattcgcggccgcgtcgacCTCCTTCTCCTCCTCCCCGCCGCCTGNGCCGCCTAGAATCGCCGC
TGCCGCCTTCTCCTCCCCCGGCCGTTGTGGTTGTGGTTGTCCCTGCCACCTCCTTACA
GCCGAGCCGCCGACACAAGATGGCGGACGCTGAGCCTGGGGCCGGAACAAAACCTT
GGGCCCCACCCCCAGAAACCCGGATGCAAGCGGGCCGCGCCTACTTATGAATCATG
CATAAAGTTCCCTACTCGGTTGCGATTCATTCGGTTAGAAGTGGAACAGCACCACCT
GGTGGACATTGTGGCAGTAACAACGAAAACAGGTNAAACAGAAGCCACGCCTCATG
GAATGCGACTAATGAATGAATTGTTGCAGCCAGGCTGTCAAGGAAGCGAAAAAAAA
ACCGTTAAGGCCATGCTTCCTGATTATAAGTTATGCATGAAGTTGAGTGGTTGGTAG
ACTTAACAACCAGCAACCAGAAAGCAGATGTTAAAACATGGAAGCCACACACCCCC
ATTCATGAATAATGATGATCTTGCAGGGGCCCGGAAGCCAAGGAGACCCAGGCCAC
AACTTACTTCATGAATAATGCATGAGGCCCAGTGGGTTGGAATAAAAGGGGCACGC
CCGCCTATTGCTGCATCTAATACACTGTAAGCAGGGAAATGGGGCTGCTGCAGGGA
AAACACACTCTCCCAGGTCCTGAATAATGAATTATGCTGCTGCAGTAGCTCAACCTG
GAAACTCAGAGAGGTCAAGAAAGGTTCCACCCAATTTATGAATTATGCATAAGGCG
AAGAAACACCCAAGACTGCCCTGCCCCTCATTTACATAAATATTATACTAGCATTTA
CCATCTCACTTCTAGGAATACTAGTATATCGCTCACACCTCATATCCTCCCTACTATG
CCTAGAAGGAATAATACTATCGCTGTCGacgcgggccgcgaattc

FIGURE 8B

```
   1 agagcactgg ggaccgagac ccggcaccac ctcccggtcc gccctccagg gaaaacggga
  61 aaactagcaa gagctagcaa gaactagcaa gagcttgaac aaacgcctgg actcagattg
 121 gaagactgct catttgtcta ctgcctcatt cctggaaatt gcactggaac tgtctgatta
 181 agaaaaacag aataattctg aaagaaagaa acaaagaaa acatactcc agaattccta
 241 atagaacact tcacctgaac ctaaaatggt gagcgagagt caccatgagg ccctggcagc
 301 cccgcctgtc accactgtcg cgactgttct gccaagcaat gccacagagc cagccagtcc
 361 tggagaagga aaggaagatg cattttctaa gctgaaggag aagtttatga atgagttgca
 421 taaaattcca ttgccaccgt gggccttaat tgcaatagcc atagtcgcag tcctttagt
 481 cctgacctgc tgcttttgta tctgtaagaa atgtttgttc aaaagaaaa acaagaagaa
 541 gggaaaggaa aaaggaggga agaatgccat taacatgaaa gatgtaaaag acttagggaa
 601 gacgatgaaa gatcaggccc tcaaggatga tgatgctgaa actggattga cagatggaga
 661 agaaaaagaa gaacccaaag aagaggagaa actgggaaaa cttcagtatt cactggatta
 721 tgatttccaa aataaccagc tgctggtagg gatcattcag gctgccgaac tgcccgcctt
 781 ggacatgggg ggcacatctg atccttacgt gaaagtgttt ctgctacctg ataagaagaa
 841 gaaatttgag acaaaagtcc accgaaaaac ccttaatcct gtcttcaatg agcaatttac
 901 tttcaaggta ccatactcgg aattgggtgg caaaacccta gtgatggctg tatatgattt
 961 tgatcgtttc tctaagcatg acatcattgg agaatttaaa gtccctatga acacagtgga
1021 ttttggccat gtaactgagg aatggcgtga cctgcaaagt gctgagaagg aagagcaaga
1081 gaaattgggt gatatctgct tctcccttcg ctacgtacct actgctggta agctgactgt
1141 tgtcattctg gaggcaaaga acctgaagaa gatggatgtg ggtggcttat ccgatcctta
1201 tgtgaagatt catctgatgc agaatggtaa gaggctgaag aagaaaaaga caacaattaa
1261 aaagaacaca cttaaccct actacaatga gtcattcagc tttgaagtac cttttgaaca
1321 aatccagaaa gtgcaggtgg tggtaactgt tttggactat gacaagattg gcaagaacga
1381 tgccatcggc aaagtctttg tgggctacaa cagcaccggc gcggagctgc gacactggtc
1441 agacatgctg gccaacccca ggcgacctat tgcccagtgg cacaccctgc aggtagagga
1501 ggaagttgat gccatgctgg ccgtcaagaa gtaaaggaaa gaagaagcct ttctgcattt
```

FIGURE 12A

```
1561 gcccatatag tgctctttag ccagtatctg taaatacctc agtaatatgg gtcctttcat 1621 ttttccagcc atgcattcct aacacaattc agtggtactt ggaatcctgt tttaatttgc 1681 acaaatttaa atgtagagag cccctaagtc cttcatcata ccactgccct ccaaatctac 1741 tcttctttta agcaatatga tgtgtagata gagcatgaat gaattatttt attgtatcac 1801 actgttgtat ataccagtat gctaaagatt tatttctagt ttgtgtattt gtatgttgta 1861 agcgtttcct aatctgtgta tatctagatg tttttaataa gatgttctat tttaaactat 1921 gtaaattgac tgagatatag gagagctgat aatatattat acggtaaata tagtatcgtc 1981 tgcattccag caaaaatatc aactcgtaag gcactagtac agttaaactg acatcttaaa 2041 ggacaactta aacctgagct ttctattgaa tcatttgagt accaagataa acttacacca 2101 catacttggt gggtgaatcc aattttgtag aattcctaca caggcaaaat agcatgatct 2161 gagcagcagc atccaggctg acctcaagga agcatagcca caaaacagaa tagcacctgt 2221 ctgtacatat ttacaaagct aaaataatgg cttcactctt atatttgagg aagcaactga 2281 acaggagtca atgatttcat attactgcat atagaataac aacaaggtgt tccgtgtgtg 2341 tgtgtgtgtg tgtgtgtgtg tgtgcacatt tgtttgggga tgggggagaa gaagctaagg 2401 ggagaagtca acatttatga aatattgcct gactatttaa aaaaaaaaa aaa
```

FIGURE 12A CONTINUED

MVSESHHEALAAPPVTTVATVLPSNATEPASPGEGKEDAFSKLK

EKFMNELHKIPLPPWALIAIAIVAVLLVLTCCFCICKKCLFKKKNKKKGKEKGGKNAI

NMKDVKDLGKTMKDQALKDDDAETGLTDGEEKEEPKEEEKLGKLQYSLDYDFQNNQLL

VGIIQAAELPALDMGGTSDPYVKVFLLPDKKKKFETKVHRKTLNPVFNEQFTFKVPYS

ELGGKTLVMAVYDFDRFSKHDIIGEFKVPMNTVDFGHVTEEWRDLQSAEKEEQEKLGD

ICFSLRYVPTAGKLTVVILEAKNLKKMDVGGLSDPYVKIHLMQNGKRLKKKKTTIKKN

TLNPYYNESFSFEVPFEQIQKVQVVVTVLDYDKIGKNDAIGKVFVGYNSTGAELRHWS

DMLANPRRPIAQWHTLQVEEEVDAMLAVKK

FIGURE 12B

```
   1 agaaggcgga gcctacctct catcaggacc agtctgactg cacctgcatc cttagctcag
  61 agcatcccg  gagcatctta agagctgagc gcagctgaca actagggggcc ggaccgtcgc
 121 aggaggcgtc cgctggatac cttcccccct ccctgaccta gagctctaca gctgctgcct
 181 cggtactgac cgagggttcc cagagctgtc tcaccattgc aaaaacgtta tagcaacagc
 241 ctctgattac gacatggctg agatcaccaa tatccgacct agctttgatg tgtcaccggt
 301 ggtggccggc ctcatcgggg cctctgtgct ggtggtgtgt gtctcggtga ccgtctttgt
 361 ctggtcatgc tgccaccagc aggcagagaa gaagcacaag aacccaccat acaagtttat
 421 tcacatgctc aaaggcatca gcatataccc agagccctc  agcaacaaga gaaaatcat
 481 caaagtgcgg agagacaaag atggtcctgg gagggaaggt ggacgtagga acctgttggt
 541 ggacgcagca gaggctggcc tgctaagccg agacaaagat cccagggggc ctagctctgg
 601 atcttgtata gaccaattac ccatcaaaat ggactatggg gaagaactaa ggagccctat
 661 tacaagcctg acccctgggg agagcaaaac cacctctcca tcatctccag aggaggatgt
 721 catgctagga tccctcacct tctcagtgga ctataacttc ccgaaaaaag ccctggtggt
 781 gacaatccag gaggcccacg ggctgccagt gatggatgac cagacccagg gatctgaccc
 841 ctacatcaaa atgaccatcc ttcctgacaa acggcatcgg gtgaagacca gagtgctgcg
 901 gaagaccctg gaccctgtgt ttgacgagac cttcaccttc tatgtcatcc cctacagcca
 961 gctgcaggac ctggtgctgc acttccttgt cctcagcttt gaccgcttct ctcgggatga
1021 tgtcattggc gaggtcatgg tgccactggc agggtggac  cccagcacag gcaaggtaca
1081 actgaccagg gacatcatca aaaggaatat ccagaagtgc atcagcagag gggagctcca
1141 ggtgtctctg tcatatcagc ctgtggcaca gagaatgaca gtggtggtcc tcaaagccag
1201 acacttgccg aagatggata tcaccggtct ctcaggtaat ccttatgtca aggtgaacgt
1261 ctactacggc agaaagcgca ttgccaagaa gaaaacccat gtgaagaagt gcactttgaa
1321 ccccatcttc aatgaatctt tcatctacga catccccact gacctcctgc ctgatatcag
1381 catcgagttc ctcgttatcg acttcgatcg caccaccaag aatgaggtgg tggggaggct
1441 gatcctgggg gcacacagtg tcacagccag tggtgctgaa cactggagag aggtctgcga
```

FIGURE 12C

```
1501 gagcccccgc aagcctgtgg ccaagtggca cagtctgagc gagtactaat cctgttcttc
1561 tctcctctaa tccccggggg ccaagctggg gagggatgtg gagggaaaa agatgacaga
1621 gaagtggact ccaaacctca ttttagttgt agaagaaaat ttcttacaaa acaaattcca
1681 caaagaacac cctatatgac cacagctgca gatcagttct tagcaatgat gttttttttt
1741 ctgctttgca aggcgctaga atcttttatt ttactttatt tttttgagg tggagtttcg
1801 ctcttgttgc ccgggctgga gtgcaatggt gagatctcaa ctcactgcaa cctctgccct
1861 tcaggttcaa gtgattctcc tccctcagcc tcccaagtag ctgggattac aggcacccac
1921 gagcatgccc ggctaatttt ttgtattttc agtagagatg ggtttcacca tgttggccag
1981 gctggtctcg aattccagac ctcaggtgat ccacccgcct cggcctccca agtgctggg
2041 attacaggtg cgagccaccg tgcccggcct ctggttttgt tttgttttt ttttttaatg
2101 ggggacaaaa gagagggaaa gaccctata aatctatata taacaatgta accatatact
2161 tgcatgtcta atacaaactg aagaaattag cctaactgcc aatatcaagt tgcagatttt
2221 aatccatgga aattgtgttt tgtgctgaat tgtatttgct gattacctga aattggcttc
2281 tttttattgg gcttctctgg agaatttctc ccactcccca cctctgcaga agaaaatttt
2341 gctcttataa aacctcatgt tttcatcatt cctatctttt ctttttattg cctcttatat
2401 ctctgctctt tgacctcaag gtctagaggt ctgcagtaag ccaagaaaca aaggtggggt
2461 ggatgaggca aggtttgcag gagaaagagg aattgagaaa tggggtattt ttgctatcag
2521 ctcttctgct atgaagtagt aaaaggcagt ctataattaa ctgacagacc taactgaagc
2581 acagagaata catcagactt atgcatccaa gacatcagaa cttggatttt atcaaacttg
2641 atgacttctc taaaaggagc tttggaaact tcaaattcag ctataggata gtaccaatga
2701 acacatccag ctgatcccaa aagctgtttt caggtataag gacaaggaga ggagacaagt
2761 gacgacagcc attccccttt gcagctatct actgtagtga cagccatttc ttggttgatg
2821 ggttggaagt catcagaggt ttgaagaatt acactggcct ttgtttttct ggaaatgccg
2881 accatggaga tgctttagag tcttctaaaa tagcttagat gttgtaatga ggttagcttt
2941 gcttcataaa acaggggccc tcagaagttc tccttaaatt tttcaataaa aatttagctc
3001 ttaaaaaaat aacagtgtga ctgagtgaat gaagataagt tggattcttt cagagcattc
3061 ttttcctcaa aacgagctgc ataattcttg gaatttatgt cttaccacat ggtggaggga
```

FIGURE 12C CONTINUED

```
3121 tgggggaact acaggatgca attcttcttc taccaatggg caatagaggt tgagagagat
3181 tcagcatctt tctgggatta gaattcaagt ctctttactc ctacagcagc tgcgtctcca
3241 acgttgagac tttgcagatg gcacagactc catggataat aggtaaactt ggggccgggc
3301 gcagtggctc acgcctgtaa tcccggtatt ttgggaggcc gaggtggaaa gatcgcttga
3361 gcccaggagt tcaagaccag cctgggctac atgacgaaac tccatctcta tcaaaaatac
3421 aaaaaattaa ctaggtgtgg tgctgcacgc ctgtggtccc agctattcag gaggctgagg
3481 tgggaggatc atttgagccc agaggtagag gctgcagtga gccatgatca tgccactgca
3541 ctctgggctg ggtaacagag tgagatcctg tctcaaaaat taattaatta attaattaaa
3601 ataaactagg taaacttgga taggcagtag atattttgc ccacctgagg aggatctcag
3661 tcaagctgtt gcttaacagc ttgatccagg gcgtgaaagg ttagttgaga ctgaagtgtt
3721 cacttccata gaagaacatc acttttaacc ttgctttggc gaagggagtc ggaaagctga
3781 gtctctatgg acgggggggt gatcttgctt tcagtgttcc ctcagctttt gtggatttaa
3841 aaccattctg ctcccctaa accttttgtt tgatttcagc ccatgttctt gacaatgcag
3901 agcaattctg agcagtcaca aagcctactc tctgttcttg tccctgccaa ccccccaccc
3961 ccataatctg actcacaact tcaccatcag ttggggtcat accactagtc tctgtcctat
4021 accccatgaa atgtaaatac tgtatcataa gtagaagaaa ataattttg ttttctaaaa
4081 atgcattttg agatagttta atgtaaatct gacaggagca ttctgaagcc ccattaggaa
4141 aaaatttaaa tggttcctct tcatcgcctt aatgtctaaa gatcagaaat cgctgagcaa
4201 acccgctttt gtttccttcc cagaaacaat gcaaaacaac aggtggagat agtctggtct
4261 ttgccctgct gtgtgtgcct ctgtagctcc tcctgacaaa cgtctgggaa aacagcctca
4321 ccccactctc ctctctcttc cccatttcct tgtagcttta ttccttgcat ctttgggtct
4381 actgagcagt gggtgctgag gtgacagggg aggaaccagt tgttctgtag cctaggaact
4441 gcctcagtgt ctttgccaga aaaggcaaa gaggcggaca gtgcagggct cctccctcct
4501 acctcaggcc tgatccatcg tgcccttgac tttgccgtct caaagtttct tagctgactt
4561 tggctttcac atttgttctt tccagagcta actgataaga gtggaggagg aatgccttct
4621 cctaagagtc agttgaaaga aagacaagag agtcacatct tagcttttgc acaaggcatt
4681 cgtggtcagg aataggttag ggaatggtca cttctgattt tccaacagtt gctccttctc
```

FIGURE 12C CONTINUED

```
4741 tgaagagatc ttgattcctt tgggaagaca agaattttc ttaataacaa aggtcacttt
4801 atgagttatt ccttctttca gttcatctca ctggagcaca gccaagatgg acatgtttat
4861 ggacagtgct ctagatgtga aaacagatag aactggtttg tgggacaggg gcagcttgct
4921 caggagaggg aataacgcag gtcccttttc ttggaaggct tgtactatgg ccatgacagt
4981 gacattgccc tcaccatgat ccctctccaa agtggttgtc tttctttacc ttgtgtcttc
5041 tcttgtaaaa atgaaactca aaataaaat aaatgtgtca aatttcgaaa aaaaaaaaa
5101 aaa
```

FIGURE 12C CONTINUED

MAEITNIRPSFDVSPVVAGLIGASVLVVCVSVTVFVWSCCHQQA

EKKHKNPPYKFIHMLKGISIYPETLSNKKKIIKVRRDKDGPGREGGRRNLLVDAAEAG

LLSRDKDPRGPSSGSCIDQLPIKMDYGEELRSPITSLTPGESKTTSPSSPEEDVMLGS

LTFSVDYNFPKKALVVTIQEAHGLPVMDDQTQGSDPYIKMTILPDKRHRVKTRVLRKT

LDPVFDETFTFYVIPYSQLQDLVLHFLVLSFDRFSRDDVIGEVMVPLAGVDPSTGKVQ

LTRDIIKRNIQKCISRGELQVSLSYQPVAQRMTVVVLKARHLPKMDITGLSGNPYVKV

NVYYGRKRIAKKKTHVKKCTLNPIFNESFIYDIPTDLLPDISIEFLVIDFDRTTKNEV

VGRLILGAHSVTASGAEHWREVCESPRKPVAKWHSLSEY

SEQUENCE LISTING

<160> NUMBER OF SEQ ID NOS: 15

<210> SEQ ID NO 1
<211> LENGTH: 1453

<212> TYPE: DNA
<213> ORGANISM: Homo sapiens
<220> FEATURE:
<221> NAME/KEY: CDS
<222> LOCATION: (272)...(955)
<221> NAME/KEY: misc_feature
<222> LOCATION: (1)...(1453)
<223> OTHER INFORMATION: n = A,T,C or G

<400> SEQUENCE: 1

```
agtcctcaac gagggtcca gtgtaggcag tgacaggcac atagctgttg agctcagcga     60
ggcggggctg tgatacctcg gcccggtttt taccgatgtc ctcctcccgc aggtagaact    120
gggaggaaag atcagcccac tgggcagtgc cctggtcatg tagggtaaca gccttgaccc    180
caccaaggat gatgttctta gcgatctcca cgcccaggcc ccgcaggcct gataccagga    240
cactggatgt ctggagccgc ttcattgcct c atg gcc caa cac ata cag ctg       292
                                   Met Ala Gln His Ile Gln Leu
                                    1               5 ccg gga gta aag gcc ctc gtc tat gtc tgc ttc act gcc gtt ctt ggc      340
Pro Gly Val Lys Ala Leu Val Tyr Val Cys Phe Thr Ala Val Leu Gly
         10                  15                  20 cat tcc gtt ggt tgg cac cga ggg cac ttc gga caa cac gga ctg ggc      388
His Ser Val Gly Trp His Arg Gly His Phe Gly Gln His Gly Leu Gly
     25                  30                  35 agg gga gca gtt aga acc cgg ctt tgg atc agg ccc gga cac gcg acg      436
Arg Gly Ala Val Arg Thr Arg Leu Trp Ile Arg Pro Gly His Ala Thr
 40                  45                  50                  55 ttt ctt gga cag cgg cga gct gga cat caa tgc cgg ttc ccc ggg tcg      484
Phe Leu Gly Gln Arg Arg Ala Gly His Gln Cys Arg Phe Pro Gly Ser
                 60                  65                  70 cgc cgc cgc caa ctc ctc aag gag ccg aag cca agc ccg gcc gca ccc      532
Arg Arg Arg Gln Leu Leu Lys Glu Pro Lys Pro Ser Pro Ala Ala Pro
             75                  80                  85 tcc tcc ttc tcc tcc tcc ccg ccg cct ggg ccg cct aga atc gcc gct      580
Ser Ser Phe Ser Ser Ser Pro Pro Pro Gly Pro Pro Arg Ile Ala Ala
         90                  95                 100 gcc gcc ttc tcc tcc ccc ggc cgt tgt ggt tgt ggt tgt ccc tgc cac      628
Ala Ala Phe Ser Ser Pro Gly Arg Cys Gly Cys Gly Cys Pro Cys His
     105                 110                 115 ctc ctt aca gcc gag ccg ccg aca caa gat ggc gga cgc ttg agc ctg      676
Leu Leu Thr Ala Glu Pro Pro Thr Gln Asp Gly Gly Arg Leu Ser Leu
120                 125                 130                 135 ggg ccg gaa caa aac ctt ggg ccc cac ccc cag aaa ccc gga tgc aag      724
Gly Pro Glu Gln Asn Leu Gly Pro His Pro Gln Lys Pro Gly Cys Lys
                 140                 145                 150 cgg gcc gcg cct act tat gaa tca tgc ata aag ttc cct act cgg ttg      772
Arg Ala Ala Pro Thr Tyr Glu Ser Cys Ile Lys Phe Pro Thr Arg Leu
             155                 160                 165 cga ttc att cgg tta gaa gtg gaa cag cac cac ctg gtg gac att gtg      820
Arg Phe Ile Arg Leu Glu Val Glu Gln His His Leu Val Asp Ile Val
         170                 175                 180 gca gta aca acg aaa aca ggt aaa aca gag gcc acg cct cat gga atg      868
Ala Val Thr Thr Lys Thr Gly Lys Thr Glu Ala Thr Pro His Gly Met
     185                 190                 195 cga cta atg aat gaa ttg ttg cag cca ggc tgt caa gga agc gaa gaa      916
Arg Leu Met Asn Glu Leu Leu Gln Pro Gly Cys Gln Gly Ser Glu Glu
200                 205                 210                 215 aaa ccg tta agg cca tgc ttc ctg att ata agt tat gca tgaagttgag       965
Lys Pro Leu Arg Pro Cys Phe Leu Ile Ile Ser Tyr Ala
                 220                 225 tggttggtag caacaaccag caaccagaaa gcagatgtta aaacatggaa gccacacacc   1025
```

```
cccattcatg aataatgat gatcttgcag gggcccggaa gccaaggaga cccaggccac    1085
aacttacttc atgaataatg catgaggccc agtgggttgg aataaagggg gcacgcccgc    1145
ctattgctgc atctaataca ctgtaagcag ggaaatgggg ctgctgcagg gaaaacacac    1205
tctcccaggt cctgaataat gaattatgct gctgcagtag ctcaacctgg aaactcagag    1265
aggtcaagaa aggttccacc caatttatga attatgcata aggcgaagaa acacccaaga    1325
ctgccctgcc cctcatttac ataaatatta tactagcatt taccatctca cttctaggaa    1385
tactagtata tcgctcacac ctcatatcct ccctactatg cctagaagga ataatactat    1445
cgctgtcg                                                             1453
```

<210> SEQ ID NO 2
<211> LENGTH: 228
<212> TYPE: PRT
<213> ORGANISM: Homo sapiens

<400> SEQUENCE: 2

```
Met Ala Gln His Ile Gln Leu Pro Gly Val Lys Ala Leu Val Tyr Val
 1               5                  10                  15

Cys Phe Thr Ala Val Leu Gly His Ser Val Gly Trp His Arg Gly His
                20                  25                  30

Phe Gly Gln His Gly Leu Gly Arg Gly Ala Val Arg Thr Arg Leu Trp
            35                  40                  45

Ile Arg Pro Gly His Ala Thr Phe Leu Gly Gln Arg Arg Ala Gly His
        50                  55                  60

Gln Cys Arg Phe Pro Gly Ser Arg Arg Arg Gln Leu Leu Lys Glu Pro
65                  70                  75                  80

Lys Pro Ser Pro Ala Ala Pro Ser Ser Phe Ser Ser Pro Pro
                85                  90                  95

Gly Pro Pro Arg Ile Ala Ala Ala Phe Ser Ser Pro Gly Arg Cys
            100                 105                 110

Gly Cys Gly Cys Pro Cys His Leu Leu Thr Ala Glu Pro Pro Thr Gln
        115                 120                 125

Asp Gly Gly Arg Leu Ser Leu Gly Pro Glu Gln Asn Leu Gly Pro His
130                 135                 140

Pro Gln Lys Pro Gly Cys Lys Arg Ala Ala Pro Thr Tyr Glu Ser Cys
145                 150                 155                 160

Ile Lys Phe Pro Thr Arg Leu Arg Phe Ile Arg Leu Glu Val Glu Gln
                165                 170                 175

His His Leu Val Asp Ile Val Ala Val Thr Thr Lys Thr Gly Lys Thr
            180                 185                 190

Glu Ala Thr Pro His Gly Met Arg Leu Met Asn Glu Leu Leu Gln Pro
        195                 200                 205

Gly Cys Gln Gly Ser Glu Glu Lys Pro Leu Arg Pro Cys Phe Leu Ile
210                 215                 220

Ile Ser Tyr Ala
225
```

<210> SEQ ID NO 3
<211> LENGTH: 684
<212> TYPE: DNA
<213> ORGANISM: Homo sapiens

<400> SEQUENCE: 3

```
atggcccaac acatacagct gccgggagta aaggccctcg tctatgtctg cttcactgcc    60
```

-continued

| | |
|---|---|
| gttcttggcc attccgttgg ttggcaccga gggcacttcg acaacacgg actgggcagg | 120 |
| ggagcagtta gaacccggct ttggatcagg cccggacacg cgacgtttct tggacagcgg | 180 |
| cgagctggac atcaatgccg gttccccggg tcgcgccgcc gccaactcct caaggagccg | 240 |
| aagccaagcc cggccgcacc ctcctccttc tcctcctccc cgccgcctgg gccgcctaga | 300 |
| atcgccgctg ccgccttctc ctccccggc cgttgtggtt gtggttgtcc ctgccacctc | 360 |
| cttacagccg agccgccgac acaagatggc ggacgcttga gcctggggcc ggaacaaaac | 420 |
| cttgggcccc accccagaa accggatgc aagcgggccg cgcctactta tgaatcatgc | 480 |
| ataaagttcc ctactcggtt gcgattcatt cggttagaag tggaacagca ccacctggtg | 540 |
| gacattgtgg cagtaacaac gaaaacaggt aaaacagagg ccacgcctca tggaatgcga | 600 |
| ctaatgaatg aattgttgca gccaggctgt caaggaagcg aagaaaaacc gttaaggcca | 660 |
| tgcttcctga ttataagtta tgca | 684 |

<210> SEQ ID NO 4
<211> LENGTH: 958
<212> TYPE: DNA
<213> ORGANISM: Homo sapiens
<220> FEATURE:
<221> NAME/KEY: misc_feature
<222> LOCATION: (1)...(958)
<223> OTHER INFORMATION: n = A,T,C or G

<400> SEQUENCE: 4

| | |
|---|---|
| gaattcgcgg ccgcgtcgac ctccttctcc tcctccccgc cgcctgngcc gcctagaatc | 60 |
| gccgctgccg ccttctcctc ccccggccgt tgtggttgtg gttgtccctg ccacctcctt | 120 |
| acagccgagc cgccgacaca agatggcgga cgctgagcct ggggccggaa caaaaccttg | 180 |
| ggccccaccc ccagaaaccc ggatgcaagc gggccgcgcc tacttatgaa tcatgcataa | 240 |
| agttccctac tcggttgcga ttcattcggt tagaagtgga acagcaccac ctggtggaca | 300 |
| ttgtggcagt aacaacgaaa acaggtnaaa cagaagccac gcctcatgga atgcgactaa | 360 |
| tgaatgaatt gttgcagcca ggctgtcaag gaagcgaaaa aaaaccgtt aaggccatgc | 420 |
| ttcctgatta taagttatgc atgaagttga gtggttggta gacttaacaa ccagcaacca | 480 |
| gaaagcagat gttaaaacat ggaagccaca cccccatt catgaataat gatgatcttg | 540 |
| caggggcccg gaagccaagg agacccaggc acaacttac ttcatgaata atgcatgagg | 600 |
| cccagtgggt tggaataaaa ggggcacgcc cgcctattgc tgcatctaat acactgtaag | 660 |
| cagggaaatg gggctgctgc agggaaaaca cactctccca ggtcctgaat aatgaattat | 720 |
| gctgctgcag tagctcaacc tggaaactca gagaggtcaa gaaaggttcc acccaattta | 780 |
| tgaattatgc ataaggcgaa gaaacaccca agactgccct gccctcatt tacataaata | 840 |
| ttatactagc atttaccatc tcacttctag gaatactagt atatcgctca cacctcatat | 900 |
| cctccctact atgcctagaa ggaataatac tatcgctgtc gacgcgggcc gcgaattc | 958 |

<210> SEQ ID NO 5
<211> LENGTH: 2453
<212> TYPE: DNA
<213> ORGANISM: Homo sapiens
<220> FEATURE:
<221> NAME/KEY: CDS
<222> LOCATION: (266)...(1534)

<400> SEQUENCE: 5

| | |
|---|---|
| agagcactgg ggaccgagac ccggcaccac ctcccggtcc gccctccagg gaaaacggga | 60 |
| aaactagcaa gagctagcaa gaactagcaa gagcttgaac aaacgcctgg actcagattg | 120 |

```
gaagactgct catttgtcta ctgcctcatt cctggaaatt gcactggaac tgtctgatta      180
agaaaaacag aataattctg aaagaaagaa acaaagaaa acatactcc agaattccta        240 atagaacact tcacctgaac ctaaa atg gtg agc gag agt cac cat gag gcc        292
                            Met Val Ser Glu Ser His His Glu Ala
                             1               5 ctg gca gcc ccg cct gtc acc act gtc gcg act gtt ctg cca agc aat        340
Leu Ala Ala Pro Pro Val Thr Thr Val Ala Thr Val Leu Pro Ser Asn
 10              15                  20                  25 gcc aca gag cca gcc agt cct gga gaa gga aag gaa gat gca ttt tct        388
Ala Thr Glu Pro Ala Ser Pro Gly Glu Gly Lys Glu Asp Ala Phe Ser
                 30                  35                  40 aag ctg aag gag aag ttt atg aat gag ttg cat aaa att cca ttg cca        436
Lys Leu Lys Glu Lys Phe Met Asn Glu Leu His Lys Ile Pro Leu Pro
             45                  50                  55 ccg tgg gcc tta att gca ata gcc ata gtc gca gtc ctt tta gtc ctg        484
Pro Trp Ala Leu Ile Ala Ile Ala Ile Val Ala Val Leu Leu Val Leu
         60                  65                  70 acc tgc tgc ttt tgt atc tgt aag aaa tgt ttg ttc aaa aag aaa aac        532
Thr Cys Cys Phe Cys Ile Cys Lys Lys Cys Leu Phe Lys Lys Lys Asn
 75                  80                  85 aag aag aag gga aag gaa aaa gga ggg aag aat gcc att aac atg aaa        580
Lys Lys Lys Gly Lys Glu Lys Gly Gly Lys Asn Ala Ile Asn Met Lys
 90                  95                 100                 105 gat gta aaa gac tta ggg aag acg atg aaa gat cag gcc ctc aag gat        628
Asp Val Lys Asp Leu Gly Lys Thr Met Lys Asp Gln Ala Leu Lys Asp
                110                 115                 120 gat gat gct gaa act gga ttg aca gat gga gaa gaa aaa gaa gaa ccc        676
Asp Asp Ala Glu Thr Gly Leu Thr Asp Gly Glu Glu Lys Glu Glu Pro
            125                 130                 135 aaa gaa gag gag aaa ctg gga aaa ctt cag tat tca ctg gat tat gat        724
Lys Glu Glu Glu Lys Leu Gly Lys Leu Gln Tyr Ser Leu Asp Tyr Asp
        140                 145                 150 ttc caa aat aac cag ctg ctg gta ggg atc att cag gct gcc gaa ctg        772
Phe Gln Asn Asn Gln Leu Leu Val Gly Ile Ile Gln Ala Ala Glu Leu
    155                 160                 165 ccc gcc ttg gac atg ggg ggc aca tct gat cct tac gtg aaa gtg ttt        820
Pro Ala Leu Asp Met Gly Gly Thr Ser Asp Pro Tyr Val Lys Val Phe
170                 175                 180                 185 ctg cta cct gat aag aag aag aaa ttt gag aca aaa gtc cac cga aaa        868
Leu Leu Pro Asp Lys Lys Lys Lys Phe Glu Thr Lys Val His Arg Lys
                190                 195                 200 acc ctt aat cct gtc ttc aat gag caa ttt act ttc aag gta cca tac        916
Thr Leu Asn Pro Val Phe Asn Glu Gln Phe Thr Phe Lys Val Pro Tyr
            205                 210                 215 tcg gaa ttg ggt ggc aaa acc cta gtg atg gct gta tat gat ttt gat        964
Ser Glu Leu Gly Gly Lys Thr Leu Val Met Ala Val Tyr Asp Phe Asp
        220                 225                 230 cgt ttc tct aag cat gac atc att gga gaa ttt aaa gtc cct atg aac       1012
Arg Phe Ser Lys His Asp Ile Ile Gly Glu Phe Lys Val Pro Met Asn
    235                 240                 245 aca gtg gat ttt ggc cat gta act gag gaa tgg cgt gac ctg caa agt       1060
Thr Val Asp Phe Gly His Val Thr Glu Glu Trp Arg Asp Leu Gln Ser
250                 255                 260                 265 gct gag aag gaa gag caa gag aaa ttg ggt gat atc tgc ttc tcc ctt       1108
Ala Glu Lys Glu Glu Gln Glu Lys Leu Gly Asp Ile Cys Phe Ser Leu
                270                 275                 280 cgc tac gta cct act gct ggt aag ctg act gtt gtc att ctg gag gca       1156
Arg Tyr Val Pro Thr Ala Gly Lys Leu Thr Val Val Ile Leu Glu Ala
            285                 290                 295
```

| | | | | | | | | | | | | | | | |
|---|---|---|---|---|---|---|---|---|---|---|---|---|---|---|---|
| aag | aac | ctg | aag | aag | atg | gat | gtg | ggt | ggc | tta | tcc | gat | cct | tat gtg | 1204 |
| Lys | Asn | Leu | Lys | Lys | Met | Asp | Val | Gly | Gly | Leu | Ser | Asp | Pro | Tyr Val | |
| | | 300 | | | | | 305 | | | | | 310 | | | |
| aag | att | cat | ctg | atg | cag | aat | ggt | aag | agg | ctg | aag | aag | aaa | aag aca | 1252 |
| Lys | Ile | His | Leu | Met | Gln | Asn | Gly | Lys | Arg | Leu | Lys | Lys | Lys | Lys Thr | |
| | | 315 | | | | | 320 | | | | | 325 | | | |
| aca | att | aaa | aag | aac | aca | ctt | aac | ccc | tac | tac | aat | gag | tca | ttc agc | 1300 |
| Thr | Ile | Lys | Lys | Asn | Thr | Leu | Asn | Pro | Tyr | Tyr | Asn | Glu | Ser | Phe Ser | |
| 330 | | | | | 335 | | | | | 340 | | | | 345 | |
| ttt | gaa | gta | cct | ttt | gaa | caa | atc | cag | aaa | gtg | cag | gtg | gta | act | 1348 |
| Phe | Glu | Val | Pro | Phe | Glu | Gln | Ile | Gln | Lys | Val | Gln | Val | Val | Thr | |
| | | | | 350 | | | | | 355 | | | | | 360 | |
| gtt | ttg | gac | tat | gac | aag | att | ggc | aag | aac | gat | gcc | atc | ggc | aaa gtc | 1396 |
| Val | Leu | Asp | Tyr | Asp | Lys | Ile | Gly | Lys | Asn | Asp | Ala | Ile | Gly | Lys Val | |
| | | | | 365 | | | | | 370 | | | | | 375 | |
| ttt | gtg | ggc | tac | aac | agc | acc | ggc | gcg | gag | ctg | cga | cac | tgg | tca gac | 1444 |
| Phe | Val | Gly | Tyr | Asn | Ser | Thr | Gly | Ala | Glu | Leu | Arg | His | Trp | Ser Asp | |
| | | | | 380 | | | | | 385 | | | | | 390 | |
| atg | ctg | gcc | aac | ccc | agg | cga | cct | att | gcc | cag | tgg | cac | acc | ctg cag | 1492 |
| Met | Leu | Ala | Asn | Pro | Arg | Arg | Pro | Ile | Ala | Gln | Trp | His | Thr | Leu Gln | |
| | | | | 395 | | | | | 400 | | | | | 405 | |
| gta | gag | gag | gaa | gtt | gat | gcc | atg | ctg | gcc | gtc | aag | aag | taa | | 1534 |
| Val | Glu | Glu | Glu | Val | Asp | Ala | Met | Leu | Ala | Val | Lys | Lys | * | | |
| 410 | | | | | 415 | | | | | 420 | | | | | |

| | |
|---|---|
| aggaaagaag aagcctttct gcatttgccc atatagtgct ctttagccag tatctgtaaa | 1594 |
| tacctcagta atatgggtcc tttcattttt ccagccatgc attcctaaca caattcagtg | 1654 |
| gtacttggaa tcctgtttta atttgcacaa atttaaatgt agagagcccc taagtccttc | 1714 |
| atcataccac tgccctccaa atctactctt cttttaagca atatgatgtg tagatagagc | 1774 |
| atgaatgaaa ttatttattg tatcacactg ttgtatatac cagtatgcta aagatttatt | 1834 |
| tctagtttgt gtatttgtat gttgtaagcg tttcctaatc tgtgtatatc tagatgtttt | 1894 |
| taataagatg ttctatttta aactatgtaa attgactgag atataggaga gctgataata | 1954 |
| tattatacgg taaatatagt atcgtctgca ttccagcaaa aatatcaact cgtaaggcac | 2014 |
| tagtacagtt aaactgacat cttaaaggac aacttaaacc tgagctttct attgaatcat | 2074 |
| ttgagtacca agataaactt acaccacata cttggtgggt gaatccaatt ttgtagaatt | 2134 |
| cctacacagg caaaatagca tgatctgagc agcagcatcc aggctgacct caaggaagca | 2194 |
| tagccacaaa acagaatagc acctgtctgt acatatttac aaagctaaaa taatggcttc | 2254 |
| actcttatat ttgaggaagc aactgaacag gagtcaatga tttcatatta ctgcatatag | 2314 |
| aataacaaca aggtgttccg tgtgtgtgtg tgtgtgtgtg tgtgtgtgtg cacatttgtt | 2374 |
| tggggatggg ggagaagaag ctaaggggag aagtcaacat ttatgaaata ttgcctgact | 2434 |
| atttaaaaaa aaaaaaaaa | 2453 |

<210> SEQ ID NO 6
<211> LENGTH: 422
<212> TYPE: PRT
<213> ORGANISM: Homo sapiens

<400> SEQUENCE: 6

Met Val Ser Glu Ser His His Glu Ala Leu Ala Ala Pro Pro Val Thr
1               5                   10                  15

Thr Val Ala Thr Val Leu Pro Ser Asn Ala Thr Glu Pro Ala Ser Pro
                20                  25                  30

Gly Glu Gly Lys Glu Asp Ala Phe Ser Lys Leu Lys Glu Lys Phe Met

```
                    35                  40                  45
Asn Glu Leu His Lys Ile Pro Leu Pro Pro Trp Ala Leu Ile Ala Ile
 50                  55                  60

Ala Ile Val Ala Val Leu Leu Val Leu Thr Cys Cys Phe Cys Ile Cys
 65                  70                  75                  80

Lys Lys Cys Leu Phe Lys Lys Asn Lys Lys Gly Lys Glu Lys
                 85                  90                  95

Gly Gly Lys Asn Ala Ile Asn Met Lys Asp Val Lys Asp Leu Gly Lys
                100                 105                 110

Thr Met Lys Asp Gln Ala Leu Lys Asp Asp Ala Glu Thr Gly Leu
                115                 120                 125

Thr Asp Gly Glu Glu Lys Glu Glu Pro Lys Glu Glu Lys Leu Gly
130                 135                 140

Lys Leu Gln Tyr Ser Leu Asp Tyr Asp Phe Gln Asn Asn Gln Leu Leu
145                 150                 155                 160

Val Gly Ile Ile Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
                180                 185                 190

Lys Phe Glu Thr Lys Val His Arg Lys Thr Leu Asn Pro Val Phe Asn
                195                 200                 205

Glu Gln Phe Thr Phe Lys Val Pro Tyr Ser Glu Leu Gly Gly Lys Thr
210                 215                 220

Leu Val Met Ala Val Tyr Asp Phe Asp Arg Phe Ser Lys His Asp Ile
225                 230                 235                 240

Ile Gly Glu Phe Lys Val Pro Met Asn Thr Val Asp Phe Gly His Val
                245                 250                 255

Thr Glu Glu Trp Arg Asp Leu Gln Ser Ala Glu Lys Glu Glu Gln Glu
                260                 265                 270

Lys Leu Gly Asp Ile Cys Phe Ser Leu Arg Tyr Val Pro Thr Ala Gly
                275                 280                 285

Lys Leu Thr Val Val Ile Leu Glu Ala Lys Asn Leu Lys Lys Met Asp
290                 295                 300

Val Gly Gly Leu Ser Asp Pro Tyr Val Lys Ile His Leu Met Gln Asn
305                 310                 315                 320

Gly Lys Arg Leu Lys Lys Lys Thr Thr Ile Lys Lys Asn Thr Leu
                325                 330                 335

Asn Pro Tyr Tyr Asn Glu Ser Phe Ser Phe Glu Val Pro Phe Glu Gln
                340                 345                 350

Ile Gln Lys Val Gln Val Val Val Thr Val Leu Asp Tyr Asp Lys Ile
                355                 360                 365

Gly Lys Asn Asp Ala Ile Gly Lys Val Phe Val Gly Tyr Asn Ser Thr
370                 375                 380

Gly Ala Glu Leu Arg His Trp Ser Asp Met Leu Ala Asn Pro Arg Arg
385                 390                 395                 400

Pro Ile Ala Gln Trp His Thr Leu Gln Val Glu Glu Val Asp Ala
                405                 410                 415

Met Leu Ala Val Lys Lys
                420

<210> SEQ ID NO 7
<211> LENGTH: 5103
<212> TYPE: DNA
<213> ORGANISM: Homo sapiens
<220> FEATURE:
```

<221> NAME/KEY: CDS
<222> LOCATION: (254)...(1549)

<400> SEQUENCE: 7

```
agaaggcgga gcctacctct catcaggacc agtctgactg cacctgcatc cttagctcag      60
agcatccccg gagcatctta agagctgagc gcagctgaca actaggggcc ggaccgtcgc     120
aggaggcgtc cgctggatac cttcccccett ccctgaccta gagctctaca gctgctgcct    180
cggtactgac cgagggttcc cagagctgtc tcaccattgc aaaaacgtta tagcaacagc     240
ctctgattac gac atg gct gag atc acc aat atc cga cct agc ttt gat        289
            Met Ala Glu Ile Thr Asn Ile Arg Pro Ser Phe Asp
              1               5                  10 gtg tca ccg gtg gtg gcc ggc ctc atc ggg gcc tct gtg ctg gtg gtg       337
Val Ser Pro Val Val Ala Gly Leu Ile Gly Ala Ser Val Leu Val Val
            15                  20                  25 tgt gtc tcg gtg acc gtc ttt gtc tgg tca tgc tgc cac cag cag gca       385
Cys Val Ser Val Thr Val Phe Val Trp Ser Cys Cys His Gln Gln Ala
 30                  35                  40 gag aag aag cac aag aac cca cca tac aag ttt att cac atg ctc aaa       433
Glu Lys Lys His Lys Asn Pro Pro Tyr Lys Phe Ile His Met Leu Lys
 45                  50                  55                  60 ggc atc agc ata tac cca gag acc ctc agc aac aag aag aaa atc atc       481
Gly Ile Ser Ile Tyr Pro Glu Thr Leu Ser Asn Lys Lys Lys Ile Ile
                 65                  70                  75 aaa gtg cgg aga gac aaa gat ggt cct ggg agg gaa ggt gga cgt agg       529
Lys Val Arg Arg Asp Lys Asp Gly Pro Gly Arg Glu Gly Gly Arg Arg
            80                  85                  90 aac ctg ttg gtg gac gca gca gag gct ggc ctg cta agc cga gac aaa       577
Asn Leu Leu Val Asp Ala Ala Glu Ala Gly Leu Leu Ser Arg Asp Lys
            95                 100                 105 gat ccc agg ggg cct agc tct gga tct tgt ata gac caa tta ccc atc       625
Asp Pro Arg Gly Pro Ser Ser Gly Ser Cys Ile Asp Gln Leu Pro Ile
110                 115                 120 aaa atg gac tat ggg gaa gaa cta agg agc cct att aca agc ctg acc       673
Lys Met Asp Tyr Gly Glu Glu Leu Arg Ser Pro Ile Thr Ser Leu Thr
125                 130                 135                 140 cct ggg gag agc aaa acc acc tct cca tca tct cca gag gag gat gtc       721
Pro Gly Glu Ser Lys Thr Thr Ser Pro Ser Ser Pro Glu Glu Asp Val
                145                 150                 155 atg cta gga tcc ctc acc ttc tca gtg gac tat aac ttc ccg aaa aaa       769
Met Leu Gly Ser Leu Thr Phe Ser Val Asp Tyr Asn Phe Pro Lys Lys
            160                 165                 170 gcc ctg gtg gtg aca atc cag gag gcc cac ggg ctg cca gtg atg gat       817
Ala Leu Val Val Thr Ile Gln Glu Ala His Gly Leu Pro Val Met Asp
            175                 180                 185 gac cag acc cag gga tct gac ccc tac atc aaa atg acc atc ctt cct       865
Asp Gln Thr Gln Gly Ser Asp Pro Tyr Ile Lys Met Thr Ile Leu Pro
            190                 195                 200 gac aaa cgg cat cgg gtg aag acc aga gtg ctg cgg aag acc ctg gac       913
Asp Lys Arg His Arg Val Lys Thr Arg Val Leu Arg Lys Thr Leu Asp
205                 210                 215                 220 cct gtg ttt gac gag acc ttc acc ttc tat gtc atc ccc tac agc cag       961
Pro Val Phe Asp Glu Thr Phe Thr Phe Tyr Val Ile Pro Tyr Ser Gln
            225                 230                 235 ctg cag gac ctg gtg ctg cac ttc ctt gtc ctc agc ttt gac cgc ttc      1009
Leu Gln Asp Leu Val Leu His Phe Leu Val Leu Ser Phe Asp Arg Phe
            240                 245                 250 tct cgg gat gat gtc att ggc gag gtc atg gtg cca ctg gca ggg gtg      1057
Ser Arg Asp Asp Val Ile Gly Glu Val Met Val Pro Leu Ala Gly Val
            255                 260                 265
```

```
gac ccc agc aca ggc aag gta caa ctg acc agg gac atc atc aaa agg      1105
Asp Pro Ser Thr Gly Lys Val Gln Leu Thr Arg Asp Ile Ile Lys Arg
    270                 275                 280 aat atc cag aag tgc atc agc aga ggg gag ctc cag gtg tct ctg tca      1153
Asn Ile Gln Lys Cys Ile Ser Arg Gly Glu Leu Gln Val Ser Leu Ser
285                 290                 295                 300 tat cag cct gtg gca cag aga atg aca gtg gtc ctc aaa gcc aga          1201
Tyr Gln Pro Val Ala Gln Arg Met Thr Val Val Leu Lys Ala Arg
                    305                 310                 315 cac ttg ccg aag atg gat atc acc ggt ctc tca ggt aat cct tat gtc      1249
His Leu Pro Lys Met Asp Ile Thr Gly Leu Ser Gly Asn Pro Tyr Val
                320                 325                 330 aag gtg aac gtc tac tac ggc aga aag cgc att gcc aag aag aaa acc      1297
Lys Val Asn Val Tyr Tyr Gly Arg Lys Arg Ile Ala Lys Lys Lys Thr
            335                 340                 345 cat gtg aag aag tgc act ttg aac ccc atc ttc aat gaa tct ttc atc      1345
His Val Lys Lys Cys Thr Leu Asn Pro Ile Phe Asn Glu Ser Phe Ile
350                 355                 360 tac gac atc ccc act gac ctc ctg cct gat atc agc atc gag ttc ctc      1393
Tyr Asp Ile Pro Thr Asp Leu Leu Pro Asp Ile Ser Ile Glu Phe Leu
365                 370                 375                 380 gtt atc gac ttc gat cgc acc acc aag aat gag gtg gtg ggg agg ctg      1441
Val Ile Asp Phe Asp Arg Thr Thr Lys Asn Glu Val Val Gly Arg Leu
                385                 390                 395 atc ctg ggg gca cac agt gtc aca gcc agt ggt gct gaa cac tgg aga      1489
Ile Leu Gly Ala His Ser Val Thr Ala Ser Gly Ala Glu His Trp Arg
            400                 405                 410 gag gtc tgc gag agc ccc cgc aag cct gtg gcc aag tgg cac agt ctg      1537
Glu Val Cys Glu Ser Pro Arg Lys Pro Val Ala Lys Trp His Ser Leu
        415                 420                 425 agc gag tac taa tcctgttctt ctctcctcta atccccgggg gccaagctgg          1589
Ser Glu Tyr  *
    430 ggagggatgt ggaggggaaa aagatgacag agaagtggac tccaaacctc attttagttg    1649 tagaagaaaa tttcttacaa aacaaattcc acaaagaaca ccctatatga ccacagctgc    1709 agatcagttc ttagcaatga tgttttttt tctgctttgc aaggcgctag aatcttttat     1769 tttactttat tttttttgag gtggagtttc gctcttgttg cccgggctgg agtgcaatgg    1829 tgagatctca actcactgca acctctgccc ttcaggttca agtgattctc ctccctcagc    1889 ctcccaagta gctgggatta caggcaccca cgagcatgcc cggctaattt tttgtatttt    1949 cagtagagat gggtttcacc atgttggcca ggctggtctc gaattccaga cctcaggtga    2009 tccacccgcc tcggcctccc aaagtgctgg gattacaggt gcgagccacc gtgcccggcc    2069 tctggttttg ttttgttttt ttttttaat ggggacaaa agagagggaa agaccccta      2129 aaatctatat ataacaatgt aaccatatac ttgcatgtct aatacaaact gaagaaatta    2189 gcctaactgc caatatcaag ttgcagattt taatccatgg aaattgtgtt ttgtgctgaa    2249 ttgtatttgc tgattacctg aaattggctt cttttttattg ggcttctctg gagaatttct   2309 cccactcccc acctctgcag aagaaaattt tgctcttata aaacctcatg tttttcatcat   2369 tcctatcttt tctttttatt gcctcttata tctctgctct ttgacctcaa ggtctagagg    2429 tctgcagtaa gccaagaaac aaaggtgggg tggatgaggc aaggtttgca ggagaaagag    2489 gaattgagaa atggggtatt tttgctatca gctcttctgc tatgaagtag taaaaggcag    2549 tctataatta actgacagac ctaactgaag cacagagaat acatcagact tatgcatcca    2609 agacatcaga acttggattt tatcaaactt gatgacttct ctaaaaggag ctttggaaac    2669
```

```
ttcaaattca gctataggat agtaccaatg aacacatcca gctgatccca aaagctgttt    2729
tcaggtataa ggacaaggag aggagacaag tgacgacagc cattcccctt tgcagctatc    2789
tactgtagtg acagccattt cttggttgat gggttggaag tcatcagagg tttgaagaat    2849
tacactggcc tttgttttc tggaaatgcc gaccatggag atgctttaga gtcttctaaa    2909
atagcttaga tgttgtaatg aggttagctt tgcttcataa aacagggcc ctcagaagtt    2969 ctccttaaat ttttcaataa aaatttagct cttaaaaaaa taacagtgtg actgagtgaa    3029
tgaagataag ttggattctt tcagagcatt cttttcctca aaacgagctg cataattctt    3089
ggaatttatg tcttaccaca tggtggaggg atggggaac tacaggatgc aattcttctt    3149
ctaccaatgg gcaatagagg ttgagagaga ttcagcatct ttctgggatt agaattcaag    3209
tctctttact cctacagcag ctgcgtctcc aacgttgaga ctttgcagat ggcacagact    3269
ccatggataa taggtaaact tggggccggg cgcagtggct cacgcctgta atcccggtat    3329
tttgggaggc cgaggtggaa agatcgcttg agcccaggag ttcaagacca gcctgggcta    3389
catgacgaaa ctccatctct atcaaaaata caaaaaatta actaggtgtg gtgctgcacg    3449
cctgtggtcc cagctattca ggaggctgag gtggaggat catttgagcc cagaggtaga    3509
ggctgcagtg agccatgatc atgccactgc actctgggct gggtaacaga gtgagatcct    3569
gtctcaaaaa ttaattaatt aattaattaa aataaactag gtaaacttgg ataggcagta    3629 gatattttg cccacctgag gaggatctca gtcaagctgt tgcttaacag cttgatccag    3689
ggcgtgaaag gttagttgag actgaagtgt tcacttccat agaagaacat cacttttaac    3749
cttgctttgg cgaagggagt cggaaagctg agtctctatg gacggggggg tgatcttgct    3809
ttcagtgttc cctcagcttt tgtggattta aaaccattct gctcccccta aaccttttgt    3869
ttgatttcag cccatgttct tgacaatgca gagcaattct gagcagtcac aaagcctact    3929
ctctgttctt gtccctgcca acccccaccc cccataatct gactcacaac ttcaccatca    3989
gttggggtca taccactagt ctctgtccta tacccatga aatgtaaata ctgtatcata    4049
agtagaagaa aataattttt gttttctaaa aatgcatttt gagatagttt aatgtaaatc    4109
tgacaggagc attctgaagc cccattagga aaaaatttaa atggttcctc ttcatcgcct    4169
taatgtctaa agatcagaaa tcgctgagca aacccgcttt tgtttccttc ccagaaacaa    4229
tgcaaaacaa caggtggaga tagtctggtc tttgccctgc tgtgtgtgcc tctgtagctc    4289
ctcctgacaa acgtctggga aaacagcctc accccactct cctctctctt ccccatttcc    4349
ttgtagcttt attccttgca tctttgggtc tactgagcag tgggtgctga ggtgacaggg    4409
gaggaaccag ttgttctgta gcctaggaac tgcctcagtg tctttgccag aaaaaggcaa    4469
agaggcggac agtgcagggc tcctccctcc tacctcaggc ctgatccatc gtgcccttga    4529
ctttgccgtc tcaaagtttc ttagctgact ttggctttca catttgttct ttccagagct    4589
aactgataag agtggaggag gaatgccttc tcctaagagt cagttgaaag aaagacaaga    4649
gagtcacatc ttagcttttg cacaaggcat tcgtggtcag gaataggtta gggaatggtc    4709
acttctgatt ttccaacagt tgctccttct ctgaagagat cttgattcct ttgggaagac    4769
aagaattttt cttaataaca aaggtcactt tatgagttat tccttctttc agttcatctc    4829 actgagcac agccaagatg gacatgttta tggacagtgc tctagatgtg aaaacagata    4889
gaactggttt gtgggacagg ggcagcttgc tcaggagagg gaataacgca ggtccctttt    4949 cttgaaggc ttgtactatg gccatgacag tgacattgcc ctcaccatga tccctctcca    5009
aagtggttgt cttctctac cttgtgtctt ctcttgtaaa aatgaaactc aaaaataaaa    5069
```
taaatgtgtc aaatttcgaa aaaaaaaaaa aaaa                    5103

<210> SEQ ID NO 8
<211> LENGTH: 431
<212> TYPE: PRT
<213> ORGANISM: Homo sapiens

<400> SEQUENCE: 8

Met Ala Glu Ile Thr Asn Ile Arg Pro Ser Phe Asp Val Ser Pro Val
1               5                   10                  15

Val Ala Gly Leu Ile Gly Ala Ser Val Leu Val Val Cys Val Ser Val
            20                  25                  30

Thr Val Phe Val Trp Ser Cys Cys His Gln Gln Ala Glu Lys Lys His
        35                  40                  45

Lys Asn Pro Pro Tyr Lys Phe Ile His Met Leu Lys Gly Ile Ser Ile
    50                  55                  60

Tyr Pro Glu Thr Leu Ser Asn Lys Lys Ile Ile Lys Val Arg Arg
65                  70                  75                  80

Asp Lys Asp Gly Pro Gly Arg Glu Gly Gly Arg Arg Asn Leu Leu Val
                85                  90                  95

Asp Ala Ala Glu Ala Gly Leu Leu Ser Arg Asp Lys Asp Pro Arg Gly
            100                 105                 110

Pro Ser Gly Ser Cys Ile Asp Gln Leu Pro Ile Lys Met Asp Tyr
            115                 120                 125

Gly Glu Glu Leu Arg Ser Pro Ile Thr Ser Leu Thr Pro Gly Glu Ser
130                 135                 140

Lys Thr Thr Ser Pro Ser Ser Pro Glu Glu Asp Val Met Leu Gly Ser
145                 150                 155                 160

Leu Thr Phe Ser Val Asp Tyr Asn Phe Pro Lys Lys Ala Leu Val Val
                165                 170                 175

Thr Ile Gln Glu Ala His Gly Leu Pro Val Met Asp Asp Gln Thr Gln
            180                 185                 190

Gly Ser Asp Pro Tyr Ile Lys Met Thr Ile Leu Pro Asp Lys Arg His
        195                 200                 205

Arg Val Lys Thr Arg Val Leu Arg Lys Thr Leu Asp Pro Val Phe Asp
210                 215                 220

Glu Thr Phe Thr Phe Tyr Val Ile Pro Tyr Ser Gln Leu Gln Asp Leu
225                 230                 235                 240

Val Leu His Phe Leu Val Leu Ser Phe Asp Arg Phe Ser Arg Asp Asp
                245                 250                 255

Val Ile Gly Glu Val Met Val Pro Leu Ala Gly Val Asp Pro Ser Thr
            260                 265                 270

Gly Lys Val Gln Leu Thr Arg Asp Ile Ile Lys Arg Asn Ile Gln Lys
        275                 280                 285

Cys Ile Ser Arg Gly Glu Leu Gln Val Ser Leu Ser Tyr Gln Pro Val
    290                 295                 300

Ala Gln Arg Met Thr Val Val Leu Lys Ala Arg His Leu Pro Lys
305                 310                 315                 320

Met Asp Ile Thr Gly Leu Ser Gly Asn Pro Tyr Val Lys Val Asn Val
                325                 330                 335

Tyr Tyr Gly Arg Lys Arg Ile Ala Lys Lys Thr His Val Lys Lys
            340                 345                 350

Cys Thr Leu Asn Pro Ile Phe Asn Glu Ser Phe Ile Tyr Asp Ile Pro
        355                 360                 365

```
Thr Asp Leu Leu Pro Asp Ile Ser Ile Glu Phe Leu Val Ile Asp Phe
    370                 375                 380

Asp Arg Thr Thr Lys Asn Glu Val Val Gly Arg Leu Ile Leu Gly Ala
385                 390                 395                 400

His Ser Val Thr Ala Ser Gly Ala Glu His Trp Arg Glu Val Cys Glu
                405                 410                 415

Ser Pro Arg Lys Pro Val Ala Lys Trp His Ser Leu Ser Glu Tyr
                420                 425                 430
```

<210> SEQ ID NO 9
<211> LENGTH: 15
<212> TYPE: PRT
<213> ORGANISM: Homo sapiens

<400> SEQUENCE: 9

```
His Gln Gln Ala Glu Lys Lys Gln Lys Asn Pro Pro Tyr Lys Phe
1               5                   10                  15
```

<210> SEQ ID NO 10
<211> LENGTH: 16
<212> TYPE: PRT
<213> ORGANISM: Homo sapiens

<400> SEQUENCE: 10

```
Lys Val Arg Arg Asp Lys Asp Gly Pro Arg Arg Glu Ser Gly Arg Gly
1               5                   10                  15
```

<210> SEQ ID NO 11
<211> LENGTH: 16
<212> TYPE: PRT
<213> ORGANISM: Artificial Sequence
<220> FEATURE:
<223> OTHER INFORMATION: forward primer

<400> SEQUENCE: 11

```
Lys Val Arg Arg Asp Lys Asp Gly Pro Arg Arg Glu Ser Gly Arg Gly
1               5                   10                  15
```

<210> SEQ ID NO 12
<211> LENGTH: 19
<212> TYPE: PRT
<213> ORGANISM: Artificial Sequence
<220> FEATURE:
<223> OTHER INFORMATION: reverse primer

<400> SEQUENCE: 12

```
Thr Thr Thr Cys Cys Thr Thr Thr Ala Cys Thr Thr Cys Thr Thr Gly
1               5                   10                  15

Ala Cys Gly
```

<210> SEQ ID NO 13
<211> LENGTH: 21
<212> TYPE: PRT
<213> ORGANISM: Artificial Sequence
<220> FEATURE:
<223> OTHER INFORMATION: reverse primer

<400> SEQUENCE: 13

```
Thr Gly Ala Ala Gly Gly Ala Cys Thr Thr Ala Gly Gly Gly Gly Cys
1               5                   10                  15

Thr Cys Thr Cys Thr
                20
```

<210> SEQ ID NO 14

```
-continued

<211> LENGTH: 20
<212> TYPE: PRT
<213> ORGANISM: Artificial Sequence
<220> FEATURE:
<223> OTHER INFORMATION: forward primer

<400> SEQUENCE: 14

Gly Ala Gly Gly Gly Thr Thr Cys Cys Cys Ala Gly Ala Gly Cys Thr
 1               5                  10                  15

Gly Thr Cys Thr
            20

<210> SEQ ID NO 15
<211> LENGTH: 19
<212> TYPE: PRT
<213> ORGANISM: Artificial Sequence
<220> FEATURE:
<223> OTHER INFORMATION: reverse primer

<400> SEQUENCE: 15

Cys Ala Cys Ala Thr Cys Cys Cys Thr Cys Cys Cys Cys Ala Gly Cys
 1               5                  10                  15

Thr Thr Gly
```

PARKIN INTERACTING POLYPEPTIDES AND METHODS OF USE

This application claims the benefit of priority of U.S. Provisional application Ser. No. 60/448,252, filed Feb. 18, 2003, the entire contents of which is incorporated herein by reference.

This invention was made with government support under grant number NS33124 awarded by the National Institutes of Health. The government has certain rights in the invention.

BACKGROUND OF THE INVENTION

The present invention relates generally to the field of molecular biology, cell biology and medicine and more specifically to Parkinson's disease.

Parkinson's disease (PD) is a major neurodegenerative disease characterized by muscle rigidity, tremor, and bradykinesia (Dunnett and Bjorklund, Nature 399:A32-A39 (1999)). Other symptoms such as postural deficits, gait impairment, and dementia are also observed in a subpopulation of PD patients. Although the majority of idiopathic PD cases are sporadic and probably influenced by environmental factors, familial aggregation of cases and rare mendelian inheritance of PD traits evince the importance of genetics.

Parkinsonism is a clinical syndrome dominated by four cardinal signs: tremor at rest, bradykinesia, a decrease in spontaneity and movement, rigidity, and postural instability. Less prominent manifestations concern the mood and intellect, autonomic function and the sensory system. The average age at onset is 55 years, with about 1% of persons 60 years of age or older having the disease. Men are affected more frequently than women.

Resting tremor and bradykinesia are the most typical parkinsonian signs and are virtually synonymous with the diagnosis. Bradykinesia accounts for most of the associated parkinsonian symptoms and signs: general slowing down of movements and of activities of daily living; lack of facial expression (hypomimia or masked facies); staring expression due to decreased frequency of blinking; impaired swallowing, which causes drooling; hypokinetic and hypophonic dysarthria; monotonous speech; small handwriting (micrographia); difficulties with repetitive and simultaneous movements; difficulty in arising from chair and turning over in bed; shuffling gait with short steps; decreased arm swing and other automatic movements; and start hesitation and freezing. Freezing, manifested by sudden and often unpredictable inability to move, is one of the most disabling of all parkinsonian symptoms.

As the population ages and the number of people over 60 increases, it is likely that a growing number of individuals will develop Parkinson's disease. Although treatments are available for treating Parkinson's disease, many of these treatments use drugs having undesirable side effects. Given the debilitating symptoms associated with Parkinson's disease, it is important to understand the cause(s) of Parkinson's disease so that additional modes of treatment can be developed.

Thus, there exists a need to identify and characterize genes and gene products associated with the development of Parkinson's disease. The present invention satisfies this need and provides related advantages as well.

SUMMARY OF THE INVENTION

The invention provides parkin binding polypeptides and encoding nucleic acids. The invention also provides antibodies specific for the parkin binding polypeptides. The invention additionally provides methods of detecting a parkin binding polypeptide and detecting a nucleic acid encoding a parkin binding polypeptide. The invention further provides methods of using a parkin binding polypeptide. In one embodiment, the invention provides a method of identifying a candidate drug for treating Parkinson's disease by contacting a parkin binding polypeptide with one or more compounds and identifying a compound that alters the activity of the parkin binding polypeptide.

BRIEF DESCRIPTION OF THE DRAWINGS

FIGS. 3A-C show the mapping of the sytXI binding site maps to a domain of parkin. FIG. 3A shows a map of parkin. Full-length and truncated parkins were constructed by PCR and cloned in-frame with a HA-epitope tag; C289G and C418R denote parkins containing missense mutation at amino acid positions 289 and 418, respectively. FIG. 3B shows that the sytXI binding site maps to the RING1 motif of the parkin. Truncated parkins missing amino acid residues 204-293, which encompass the RING1 finger motif, fail to bind to sytXI. The C289G missense mutated parkin interacts weakly with sytXI compared to the C418R mutant. FIG. 3C shows expression of HA-tagged parkins in HEK293 cells. Western blot of HEK293 cells overexpressing the full-length wild-type, missense mutated, or various truncated parkins was detected with anti-HA-peroxidase.

FIG. 4C shows a western blot of the same lysate with anti-HA antibody, indicating that the truncated and mutated parkins are expressed at higher levels than wild-type parkin.

FIGS. 6A-R show subcellular distribution of endogenous synaptotagmins I and XI in nontransfected PC12 cells and human substantia nigra neurons. FIGS. 6A-C and P—R show immunofluorescence of PC12 cells induced with 50 ng/ml NGF for 7 days. The cells were immunofluoroscently co-labeled with antibodies to rabbit parkin (stained red, FIG. 6P) and mouse syt1 (staine green, FIG. 6Q), or chicken parkin (stained green, FIG. 6A) and rabbit-syt11 (stained red, FIG. 6B). Images were acquired by Leica TCSSP microscopy using a 100× oil immersion lens. Stacked images were merged (FIGS. 6C and R). Yellow indicates colocalization of two proteins. Inserts in FIGS. 6 A-C and P-R are from the cell body of the same cell from which the long neurite arises (shown at lower magnification). Parkin and syt colocalize in the perinuclear area and boutons (arrows) along the neurite. FIGS. 6M-O show adjacent PD brain sections labeled with rabbit anti-ubiquitin (M), anti-sytXIA (N), and anti-sytXIA sytXIA peptide (O); black arrows point to Lewy bodies. Note the absence of Lewy body labeling by preabsorbed sytXIA antibody. Images were acquired using a 20× lens (FIGS. 6D-F), and 63× oil immersion lens (FIGS. 6G-O).

FIG. 8 shows the nucleotide (SEQ ID NO:1) and amino acid (SEQ ID NO:2) sequences of a parkin binding polypeptide, human synapsin-like protein (SLP), also referred to herein as MP23. The SLP cDNA coding region is nucleotide 272 to 955 (SEQ ID NO:3). FIG. 8B shows a partial cDNA sequence (SEQ ID NO:4) of SLP (MP23a). Lower case letters are the pGAD10 vector. The first nucleotide of the SLP sequence corresponds to nucleotide 535 of the nucleotide sequence shown in FIG. 8A.

FIGS. 10C and D show the labeling of LBs with anti-SLP (FIG. 10C) and anti-ubiquitin (FIG. 10D) antibodies.

FIGS. 12A and 12B show the nucleotide (SEQ ID NO:5) and amino acid (SEQ ID NO:6) sequences, respectively, of human synaptotagmin I (syt1) cDNA (GenBank accession number BC058917). FIGS. 12C and 12D show the nucleotide (SEQ ID NO:7) and amino acid (SEQ ID NO:8) sequences, respectively, of human synaptotagmin XI (syt11) cDNA (GenBank accession number BC039205).

DETAILED DESCRIPTION OF THE INVENTION

Figure 1:
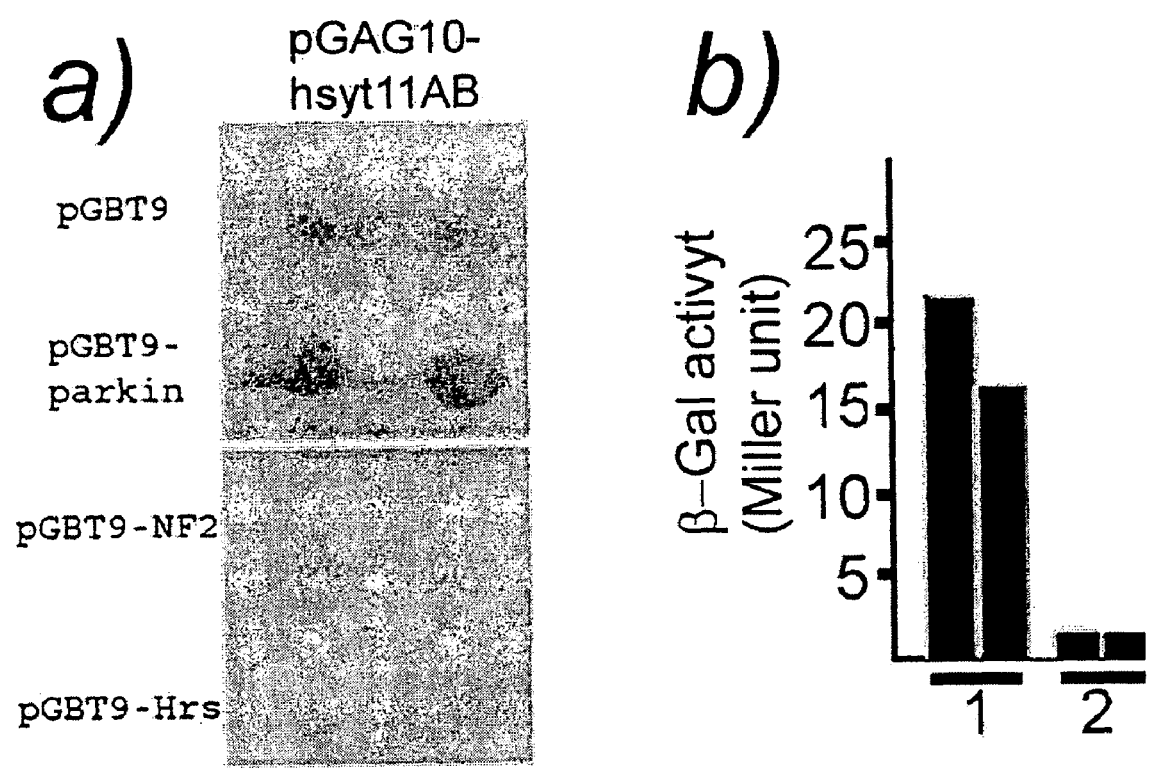
FIG. 1A shows a yeast two-hybrid filter assay. Yeast cells transformed with pGAD10-hyst11AB and pGBT9-parkin produced a positive reaction with β-galactosidase substrate.
FIG. 1B shows a representative yeast two-hybrid liquid assay. Yeast were transformed with pGAD10-hsyt11AB and pGBT9-parkin plasmids ("1" in FIG. 1B) or with pGAD10-hsyt11AB and the pGBT9 vector control ("2" in FIG. 1B).

The present invention provides parkin binding polypeptides (PBPs). The present invention additionally provides methods using parkin binding polypeptides.

In Parkinson's disease (PD), the level of dopamine is decreased in the striatum, but most severely in the putamen. This is largely a result of degeneration of dopamine-producing neurons in the substantia nigra pars compacta (Yamada et al., *Brain Res.* 526:303-307 (1990); Damier et al., *Brain* 122:1437-1448 (1999); and Naoi et al., *Mech. Ageing Dev.* 111:175-188 (1999)). Three genes have been associated with autosomal dominant PD, NR4A2 (Le et al., *Nat. Genet.* 33:85-89 (2003), α-synuclein (Polymeropoulos et al., *Science* 276:2045-2047 (1997), and ubiquitin C-terminal hydroxylase L1 (UCHL1) (Wintermeyer et al., *Neuroreport* 11:2079-2082 (2000). The two genes that have been associated with autosomal recessive PD are parkin (Kitada et al., *Nature* 392:605-608 (1998) and DJ-1 (Bonifati et al., *Science* 299:256-259 (2003). Inactivating mutations of the parkin gene cause PARK2 autosomal recessive juvenile parkinsonism (AR-JP). Similar to other PD forms, PARK2 is characterized by loss of dopaminergic neurons in the substantia nigra. However, PARK2 is unique in that Lewy bodies in substantia nigra neurons are absent in most cases of AR-JP (Ishikawa and Tsuji, *Neurology* 47:160-166 (1996); Ishikawa and Takahashi, *J. Neurol.* 245:4-9 (1998); and Matsumine, *J. Neurol.* 245:10-14 (1998)). Mutations in the parkin gene cause a from of AR-JP but are also found in older PD patients, demonstrating that parkin mutations are not limited to juvenile onset (Abbas et al., *Hum. Mol. Genet.* 8:567-574 (1999)).

Inactivating mutations of the gene encoding parkin are responsible for some forms autospomal recessive juvenile Parkinson disease. Parkin is a ubiquitin ligase that ubiquitinates misfolded proteins targeted for the proteasome-dependent protein degradation pathway. Clues to the function of parkin are suggested by the primary structure of parkin and the localization of the mutation sites in the parkin gene. Parkin is composed of a ubiquitin-like domain in the N-terminal domain and two RING finger motifs toward the C-terminal domain (Kitada et al., supra, 1998, and Shimura et al., *Nat. Genet.* 25:302-305 (2000)). Several inactivating mutations are found in the RING finger domains and suggest that these domains are functionally important (Shimura et al., *Ann. Neurol.* 45:668-672 (1999)). To date, only one missense (Arg42Pro) and three frameshift mutations have been found in the ubiquitin-like domain. The arginine at position 42 is appears to function in the binding of target proteins. Shimura et al., supra, 2000, demonstrated that the ubiquitin-conjugating H7 protein binds to the RING finger domain and that the RING domains of parkin are required for ubiquitination in human dopaminergic SH-Sy5Y neuroblastoma cells. These observations suggest different roles for the ubiquitin-like and RING finger domains. The ubiquitin-like domain was found to be important for the stability of parkin (Finney et al., *J. Biol. Chem.* 278:16054-16058 (2003) and probably for targeting the ubiquitinated substrates to the proteasome. The RING fingers, on the other hand, bind to substrates and other ubiquitin components, such as UbCH7 (E2), required for the ubiquitin-ligase activity. This observation was confirmed (Zhang et al., *Proc. Natl. Acad. Sci. USA* 97:13354-13359 (2000)), and it was further found that parkin bound to CDCrel-1, a member of a synaptic vesicle associated protein family named septin, and that parkin stimulated the ubiquitylation and turnover of this protein. Together, these data led to the suggestion that parkin functions as an E3 ubiquitin ligase.

The E3 ubiquitin ligases, together with the activating E1 and often with the conjugating E2 enzymes, catalyze the conjugation of ubiquitin chains to cytoplasmic proteins targeted for degradation in the 26S proteasome complex to regulate important cellular processes such as cell cycle, cell death, and cell differentiation. The ubiquitinated substrate can be degraded either through the proteasome-dependent pathway (Joazeiro and Weissman, *Cell* 102:549-552 (2000)), if the substrate is polyubiquitinated (contains chains of more than 5 ubiquitin units), or through the lysosomal degradation pathway, if the protein is monoubiquitinated (contains less 5 chains of short ubiquitins). Monoubiquitination can cause certain cell surface receptors, for example, EGF receptor, to internalize (endocytose) or can function as a protein sorting signal in the endosomal pathway (Helliwell et al., *J. Cell. Biol.* 153:649-662 (2001); Hicke, *Cell* 106:527-530 (2001); and Hicke, *Nat. Rev. Mol. Cell. Biol.* 2:195-201 (2001)) and direct these monoubiquitinated proteins to the lysosome. Parkin has been found to interact with several proteins, which include the Pael-1 receptor (Imai et al., *Cell* 105:891-902 (2001)); CDCrel-1 (Zhang et al., *Proc. Natl. Acad. Sci. USA* 97:13354-13359 (2000)); glycosylated α-synuclein (Shimura et al., *Science* 293:263-269 (2001)); synphilin-1 (Chung et al., *Nat. Med.* 7:1144-1150 (2001)); CHIP (Imai et al., *Mol. Cell.* 10:55-67 (2002)); cyclin E (Starpoli et al., *Neuron* 37:735-749 (2003)); HSP70 (Tsai et al., *J. Biol. Chem.* 278:22044-22055 (2003)); α/β-tubulin (Ren et al., *J. Neurosci.* 23:3316-3324 (2003)); and the p38 subunit of the aminoacyl t-RNA synthetase complex (Corti et al., *Hum. Mol. Genet.* 12:1427-1437 (2003)). Parkin-mediated ubiquitination led to the degradation of these proteins by the proteasome system. Absence of parkin-mediated degradation of the Pael-1 receptor resulted in the accumulation of the Pael receptor, causing cell death (Imai et al., supra, 2001).

As disclosed herein, the yeast two-hybrid system was used to identify parkin interacting polypeptides. In particular, it was found that parkin interacts with synaptotagmins 1 and 11 (see Examples I-VI) and SLP (Example VII). Interaction with parkin causes the ubiquitination of synaptotagmins, and alters subcellular localization of synaptotagmins. The yeast two-hybrid system and co-immunoprecipitation methods were used to identify that parkin interacts with members of the synaptotagmin family through their C2A and C2B domains. Parkin polyubiquitinates and degrades synaptotagmin 1 and 11. Coexpression of parkin and synaptotagmin results in a change of the normal synaptotagmin localization to perinuclear structures containing both parkin and synaptotagmin. Truncated and missense parkins, including parkins containing disease-causing amino acid substitutions, inhibited the interaction with synaptotagmins 1 and 11 and their ubiquitination. Mutant parkins failed to alter subcellular localization of synaptotagmins. Parkin-mediated ubiquitination also enhances the turnover of synaptotagmin 11. As synaptotagmins are well characterized in their importance for vesicle formation and docking, these results indicates a role for parkin and synaptotagmins in the regulation of the synaptic vesicle pool and in vesicle release. Thus, the interaction of parkin with members of the synaptotagmin family suggests an involvement of parkin in the regulation of proteins involved in controlling neurotransmitter trafficking at the presynaptic terminal. Parkin binds to C2 domains in synaptotagmin, a calcium-sensing domain that is found in many proteins involved in synaptic function. Loss of parkin can thus affect multiple proteins controlling vesicle pools, docking and release and explain the deficits in dopaminergic function seen in patients with parkin mutations.

As disclosed herein, two members of the synaptotagmin family that interact with parkin were identified and characterized. The results disclosed herein confirm that parkin bound to synaptotagmin 1 and 11 based on the following observations. First, parkin co-immunoprecipitated only with GFP tagged synaptotagmin 1 or 11 but not with the GFP tag alone (Example III and FIG. 2B). Second, endogenous parkin interacts with endogenous syt1 (Example III and FIG. 2C). Third, only wild type parkin and truncated parkins containing the RING finger motifs bound to synaptogomin 1 and 11 (Example IV and FIG. 3C). Fourth, truncated parkins lacking the RING finger motif and parkins with amino acid substitutions failed to interact or interacted weakly with synaptotagmins (Example IV and FIG. 3C). Fifth, only wild type parkin ubiquitinated synaptotagmin leading to its degradation, while all truncated and mutated parkins showed reduced or absent ubiquitination of synaptotagmins (Example V FIGS. 4 and 6). Sixth, endogenous parkin co-localized with synaptotagmin 1 and 11 at synaptic boutons along the neurites of NGF-induced PC12 cells and in a perinuclear location (Example VI and FIG. 5). Finally, coexpression of parkin and synaptotagmins resulted in the recruitment of parkin-synaptotagmin complexes to structures in a perinuclear distribution (Example VI and FIG. 6).

Parkin has been found to interact with synphilin-1 (Chung et al., supra (2001)), Pael-1 receptor (Imai et al., supra (2001)), CDCrel-1 (Zhang et al., supra 2000)), and glycosylated synuclein (Shimura et al., Science (2001)). Two of these proteins are synaptic vesicle associated proteins, the CDCrel-1 and synphilin-1 (Ribeiro et al., J. Biol. Chem. 277: 23927-23933 (2002); Wakabayashi et al., Acta Neuropathol 103-209-214 (2002); and Beites et al., Nat. Neurosci. 2:434-439 (1999)), while the Pael-1 receptor is a transmembrane protein with unknown function, and the glycosylated synuclein is a rare protein found in Lewry bodies. CDCrel-1 interacts with syntaxin, and overexpression of the wild type CDCrel-1 inhibits secretion in HIT-T15 cells (Ribeiro et al., supra (2002); Wakabayashi et al., supra (2002); and Beites et al., supra (1999)). Synphilin-1 interacts with α-synuclein and stimulates the formation of cytosolic Lewy bodies in PD (Engelender et al., Nat. Genet. 22:110-114 (1999)). The presence of wild type parkin appears to be essential for synphilin-1 induced formation of the Lewry bodies. It is currently unknown how CDCrel-1 or synphilin-1 participate in the regulation of presynaptic neurotransmission, and it is also unclear whether CDCrel-1 or synphilin-1 is involved in regulating the presynaptic secretion of dopamine. The finding that parkin interacts with and ubiquitinates members of the synaptotagmin family further supports the hypothesis that parkin plays an important role in regulating synaptic vesicle associated proteins.

Synaptotagmin 1 and 11 (also referred to herein as synaptotagmins I and XI or syt1 and sytXI) belong to a large family of approximately 50 calcium binding proteins with high homology in the $C_2A$ and $C_2B$ domains (BLAST search). These proteins include synaptotagmins 1 to 13, raphilin-2a, protein kinase C, GTPase-activating protein (GAP), rat/yeast ubiquitin ligase Nedd4, and phospholipase. Together, these proteins serve a common function as regulators of cell signal transduction ranging from calcium sensor (syts and protein kinase C) to phosphorylation (GAP) and phospholipid degradation (phospholipase C). Among the synaptotagmins, syt1 has the highest homology with syt2 and is expressed abundantly in synaptic vesicles and secretory granules (Sudhof, J. Biol. Chem. 277:7629-7632 (2002)). Syts 1 and 2 function as a calcium sensor in fast presynaptic neurotransmission (Fernandez-Chacon et al., Nature 410:41-49 (2001) and Geppert et al., Cell 79:717-727 (1994)) similar to syt 3, 5-7, and 10. Synaptotagmin 11, in contrast, is similar to syt4 owing to a conserved substitution of an aspartate by a serine residue in the $C_2A$ domain, resulting in the deficiency of $Ca^{+2}$ binding to this domain (von Poser et al., J. Biol. Chem. 272:14314-14319 (1997)). Although the cellular localization of syt11 is unknown, syt4 is localized in the Golgi apparatus (Fukuda et al., J. Neurochem. 77:730-740 (2001) and Berton et al., Eur. J. Neurosci. 12:1294-1302 (2000)). The functions of syts 4 and 11, 8, 9, 12, and 13 are currently speculative, although syt4 is thought to function as a down regulator of the fast presynaptic neurotransmission (Wang et al., Science 294:1111-1115 (2001)). Overall, members of the syt family have high homology at the C2 domains with amino acid identity ranging from 30% to 50%. Since parkin binds to the $C_2A$ and $C_2B$ domains of syt 11, it is likely that parkin interacts with other syts as well. The observation that parkin also interacts with and regulates syt 1, a protein that contains the lowest $C_2$ domain homology (30% identity) with syt11, suggest that parkin may interact with a wide range of proteins containing domains related to $C_2A$ and $C_2B$ sequences.

Presynaptic neurotransmission involves three processes: 1) docking, 2) fusion, and 3) recycling of synaptic vesicles. Experimental evidence has linked synaptotagmin 1 to all three processes. At the docking stage, synaptotagmin 1 interacts with t-SNARE proteins, syntaxin and SNAP25 to stimulate synaptic vesicle docking (Schiavo et al., Proc. Natl. Acad. Sci. USA 94:997-1001 (1997) and Li et al., Nature 375:594-599 (1995)). At the fusion stage, syt 1 interacts with the assembled SNARE complex and phospholipids to stimulate and stabilize the fusion of synaptic vesicles (Leveque et al., J. Neurochem. 74:367-374 (2000); Gerona et al., J. Biol. Chem. 275:6328-6336 (2000); and Davis et al., Neuron. 24:363-376 (1999)). At the recycling stage, the interaction of syt 1 with the clathrin assembly protein complex AP-2 is important for synaptic vesicle recycling (Zhang et al., Cell 78:7510760 (1994). In addition to these interactions, functional data also suggest that synaptotagmin 1 plays important roles in synaptic vesicle docking (Reist et al., J. Neurosci. 18:7662-7673 (1998)), fusion (Geppert et al., supra (1994); Elferink et al., Cell 72:153-159 (1993); DiAntonio et al., Cell 73:1281-1290 (1993); DiAntonio et al., Neuron. 12:909-920 (1993); and Bommert et al., Nature 363:163-165 (1993)), and recycling (Jorgensen et al., Nature 378:196-199 (1995)).

Furthermore, studies in syt1 knock-out mice suggest that syt1 is the major $Ca^{++}$ sensor for rapid neurotransmitter exocytosis (Fernandez-Chacon et al., supra (2001)) and $Ca^{++}$-sensitive large dense-core vesicle exocytosis (Voets et al., Proc. Natl. Acad. Sci. USA 98:11680-11685 (20010)). Overexpression of syt1 extends the time of fusion pore opening, while overexpression of syt 4 shortens the fusion pore opening time (Wang et al., supra (2001)), suggesting that synaptotagmins 1 and 4 possess complementing functions. It is unknown whether members of the syt family are involved in regulating dopamine secretion in dopaminergic neurons. It is also unknown whether failure of the regulated degradation of syts by mutated parkins results in impaired synaptogenesis (Murphey and Godenschwege, *Neuron* 36:5 (2002)), leading to a reduction in dopamine secretion in dopaminergic neurons. However, the observation disclosed herein that wild type parkin but not mutated or truncated parkins interacts and regulates syts 1 and 11 indicates that parkin is an important E3 ubiquitin ligase and regulates synaptic vesicle functioning at the presynaptic membrane.

Figure 6:
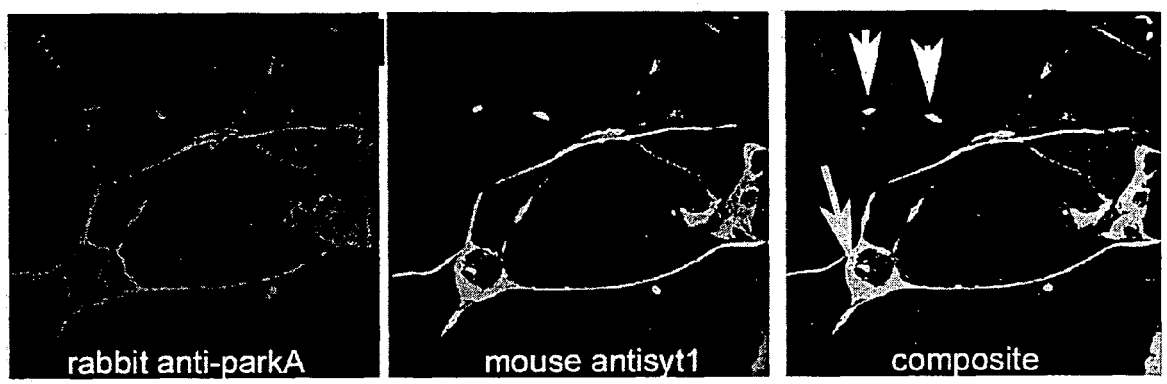
FIG. 6 D-L shows distribution of synaptotagmin XI and parkin in a normal human substantia nigra section. Human substantia nigra sections were labeled with the rabbit anti-sytXIA antibody (D, G, J), anti-sytXIA antibody preabsorbed with 100 sytXIA peptide (E, H, K), or rabbit anti-parka antibody (F, I, L). Images show the cell bodies and neurites of dopaminergic neurons in the substantia nigra.

SytXI is found in the central core of LBs in substantia nigra neurons from patients with idiopathic PD (see FIG. 6). This distribution is also observed for other parkin substrates, p38 subunit of the aminoacyl tRNA synthetase complex and synphilin-1 (Corti et al., *Hum. Mol. Genet.* 12:1427-1437 (2003); Wakabayashi et al., *Ann. Neurol.* 47:521-523 (2000); Schlossmacher et al., *Am. J. Pathol.* 160:1655-1667 (2002)). The finding of sytxI in LBs suggests a potential link of abnormal processing of synaptotagmins in PD. Whether LBs play a role in dopaminergic neuronal death in Parkinsonism is speculative. The absence of LBs in parkin associated parkinsonism (Hayashi et al., *Mov. Discord.* 15:884-888 (2000); Mori et al., *Neurology* 51:890-892 (1998); van de Warrenburg et al., *Neurology* 56:555-557 (2001)) implies that these inclusions are not the primary cause of dopaminergic neuronal degeneration in parkin-associated parkinsonism.

Parkin consists of three functional domains, the ubiquitin like, RING1 and RING2 domains (Shimura et al., *Nat. Genet.* 25:302-305 (2000)). The RING2 domain was found to be required for binding to ubiquitin-conjugating enzymes (Shimura et al., supra, 2000; Zhang et al., *Proc. Natl. Acad. Sci. USA* 97:13354-13359 (2000); Imai et al., *J. Biol. Chem.* 275:35661-35664 (2000)) and the ubiquitin-like domain is important for the stability of parkin (Finney et al., *J. Biol. Chem.* 278:16054-16058 (2003)). However, the RING finger motifs were found later to be essential for parkin binding to its two substrates, CDCrel-1 (Zhang et al., supra, 2000) and Pael-R (Imai et al., supra, 2000). Consistent with these findings and as disclosed herein, sytXI was found to bind to the region between amino acid residues 204 and 293 (FIG. 3). This region contains the RING1 motif. Furthermore, a parkin peptide lacking only the ubiquitin-like domain (p78-465) bound more weakly to synaptotagmins than parkins containing the ubiquitin-like domain (FIG. 3B). These observations suggest that the ubiquitin-like domain is important for the correct folding of the full-length parkin to expose the RING finger motif for synaptotagmin binding. We suggest that the three parkin domains serve distinct functions: the ubiquitin-like domain is required for the correct folding and stability of parkin, the p204-293 domain, which contains the RING1 finger motif, is essential for the interaction with the C2 domain containing proteins such as sytXI, whereas the RING2 finger motif is important for complex formation with the E1 ubiquitin-activating enzyme and the E2 ubiquitin-conjugate proteins.

Figure 4:
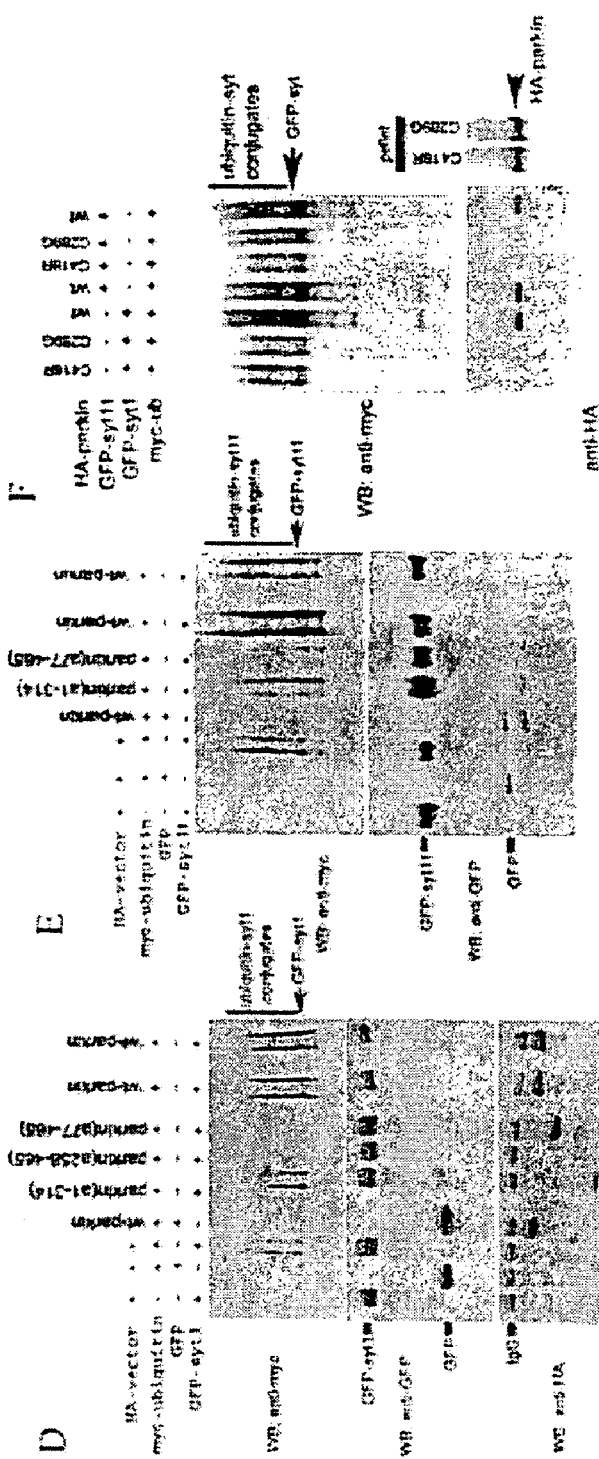
FIGS. 4A-C show ubiquitination assays of sytxI. HEK293 cells overexpressing HA-parkins or controls with the corresponding myc-ubiquitin and GFP-tagged proteins were treated with lactacystin for 4 h, and protein extracts were immunoprecipitated with anti-GFP antibody. IP products of the ubiquitination assays were detected with an antibody to the myc tag (FIG. 4A) and anti-GFP antibody (FIG. 4B). Note the lack of ubiquitinated products in cells expressing HA-parkin and GFP, and the undetectable level of ubiquitination of GFP-sytXI in other controls. Cells expressing parkin mutants and GFP-sytXI produce a lower amount of ubiquitin-conjugated sytXI compared with the wild-type parkin. The anti-GFP antibody detects near equal amounts of GFP-sytXI monomer in all samples containing GFP-sytXI and a large GFP-sytXI band near the well containing the sample co-expressed with both GFP-sytXI and HA-parkin.
FIG. 4D shows immunoprecipitation with anti-GFP antibody of protein extracts of HEK293 cells overexpressing HA-parkins and the corresponding myc-ubiquitin and GFP-tagged syt1 proteins. The cells were treated with lactacystin, an inhibitor of the proteosome complex, for 4 hours. Immunoprecipitation products of the ubiquitination assays were detected with antibodies to myc- (top panel), GFP- (middle panel), and HA-tags (bottom panel).
FIG. 4E is similar to FIG. 4D except that GFP-syt11 was used. Western blots were detected with anti-myc (top panel) and anti-GFP (bottom panel) antibodies.
FIG. 4F shows co-ip and western blots with mutated parkins, C289G and C418R.

Parkin is an E3 ubiquitin ligase (Shimura et al., supra, 2000; Zhang et al., supra, 2000) that catalyzes the ubiquitination of targeted proteins. Polyubiquitination will lead to the degradation of the ubiquitin-conjugated substrate by the proteasome. Wild-type parkin strongly catalyzes the polyubiquitination of sytXI compared with truncated parkins, missense mutated parkins, or negative controls (FIG. 4). Parkin-dependent ubiquitination also led to rapid turnover of sytXI (FIG. 5) further supporting the hypothesis that parkin regulates the level of sytXI. Cells expressing truncated parkins or missense mutated parkins (C289G and C418R) produced the same amounts of ubiquitinylated sytXI as cells expressing only GFP-sytXI (FIG. 4). These observations suggest that truncating or missense mutations of parkin reduce or eliminate the ubiquitination of sytXI. In PARK2 AR-JP, mutations of parkin probably cause a decrease in the ubiquitination of specific proteins, resulting in an increase in their intracellular levels of sytXI and other proteins regulated by parkin. The net effect of the abnormal increase in the intracellular levels of parkin regulated proteins probably contributes to the pathological conditions of AR-JP.

SytXI mRNA is expressed abundantly in the brain, but at lower levels in nonneural tissues (von Poser et al., *J. Biol. Chem.* 272:14314-14319 (1997)). However, information on the specific subcellular distribution of endogenous sytXI protein is unknown. Exogenous sytXI in PC12 cells was mainly localized in the Golgi network (Fukuda and Mikoshiba, *Biochem. J.* 354:249-257 (2001)). In non-transfected NGF-induced PC12 cells, endogenous parkin and sytXI were found co-localized in a perinuclear distribution and in dense-core vesicles in the NGF-induced processes (FIG. 6). The distribution pattern of endogenous parkin was similar to previous observations (Huynh et al., *Ann. Neurol.* 48:737-744 (2000)). The distribution of sytXI was also similar to the subcellular distribution of sytIV, a protein with 48% identity to sytXI. In PC12 cells, sytIV is localized mainly in the Golgi and immature vesicles (Berton et al. *Eur. J. Neurosci.* 12:1294-1302 (2000); Ibata et al., *J. Neurochem.* 74:518-526 (2000); Fukuda et al., *J. Neurochem.* 77:730-740 (2003); Fukuda et al., *J. Biol. Chem.* 278:3220-3226 (2003)). When PC12 cells are treated with NGF, sytIV protein redistributes to the mature dense-core vesicles (Fukuda et al., *J. Biol. Chem.* 278:3220-3226 (2003)). Dense-core vesicles are secretory granules that carry neuropeptides or biogenic amines, and release their contents under the stimulation of calcium ions. Therefore, the observation that both sytXI and parkin co-localize in the dense-core vesicles suggests that both proteins probably play a role in the calcium-dependent exocytosis. This hypothesis is further supported by the observation that both parkin and sytXI have similar distribution patterns in the neurites and cell bodies of neurons in the human substantia nigra (FIG. 6).

The loss of parkin function in patients with AR-JP is expected to alter synaptotagmin XI function, resulting in altered dopamine release, which in turn causes the symptoms of dystonia and parkinsonism. Altered vesicle functioning, be it at the stages of release or recycling, may cause an increase of cytoplasmic dopamine, resulting in increased oxidative damage and subsequently in cell death, explaining the neurodegeneration seen in patients with parkin mutations.

The results disclosed herein indicate that loss of parkin could result in altered dopamine release resulting in the initial symptoms of dystonia and parkinsonism. Altered vesicle functioning, either at the stages of release or recycling, could result in an increase of cytoplasmic dopamine resulting in increased oxidative damage and subsequently in cell death.

The invention provides exemplary parkin binding polypeptides, including synaptotagmins 1 and 11 and SLP. The invention also provides methods of identifying parkin binding polypeptides, as disclosed herein. The invention further provides methods of using parkin binding polypeptides.

The invention provides an isolated polypeptide encoding a parkin binding polypeptide (PBP). In a particular embodiment, the invention provides an isolated polypeptide having the amino acid sequence referenced as SEQ ID NO:2. The invention also provides a functional fragment of a PBP.

As used herein, the term "functional fragment," when used in reference to a parkin binding polypeptide (PBP), is intended to refer to a portion of a parkin binding polypeptide that retains some or all or the activity of a parkin binding polypeptide. An exemplary functional fragment of a PBP includes a parkin binding fragment of a PBP Another exemplary functional fragment of a PBP is a functional fragment that specifically binds to an antibody specific for the PBP. Other functional fragments of a PBP include peptide fragments that are epitopes that function as antigenic fragments, which can be used to generate an antibody specific for a particular PBP.

As used herein, the term "polypeptide" when used in reference to a parkin binding polypeptide (PBP) refers to a peptide or polypeptide of ten or more amino acids, including up to a full length parkin binding polypeptide. As used herein, a "peptide fragment" refers to a peptide or polypeptide of two or more amino acids. A "modification" of a parkin binding polypeptide can include a conservative substitution of the PBP amino acid sequence, so long as the modification retains a function of the PBP. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln.); (3) polar acidic amino acids (Asp and Glu); (4) polar basic amino acids (Lys, Arg and His); and (5) aromatic amino acids (Phe, Trp, Tyr, and His). Other minor modifications are included within PBPs so long as the polypeptide retains some or all of its function as described herein.

A modification of a polypeptide can also include derivatives, analogues and functional mimetics thereof, so long as the modification retains a function of the PBP. For example, derivatives can include chemical modifications of the polypeptide such as alkylation, acylation, carbamylation, iodination, or any modification that derivatives the polypeptide. Analogues can include modified amino acids, for example, hydroxyproline or carboxyglutamate, and can include amino acids that are not linked by peptide bonds. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide a function of a PBP, are included within the meaning of a derivative of a PBP.

As used herein, the term "substantially" or "substantially the same" when used in reference to a nucleotide or amino acid sequence is intended to mean that the nucleotide or amino acid sequence shows a considerable degree, amount or extent of sequence identity when compared to a reference sequence. A substantially the same amino acid sequence retains a functional and/or biological activity characteristic of the reference polypeptide.

As used herein, the term "nucleic acid" means a polynucleotide such as deoxyribonucleic acid (DNA) or ribonucleic acid (RNA) and encompasses both single-stranded and double-stranded nucleic acid as well as an oligonucleotide. Nucleic acids useful in the invention include genomic DNA, cDNA and mRNA and can represent the sense strand, the anti-sense strand, or both. A genomic sequence of the invention includes regulatory regions such as promoters and enhancers that regulate expression of a PBP gene and introns that are outside of the exons encoding a PBP but does not include proximal genes that do not encode a PBP. An exemplary PBP nucleic acid includes the nucleotide sequence referenced as SEQ ID NOS:1, 3 and 4, or fragments thereof. The term "isolated" used in reference to a PBP nucleic acid molecule is intended to mean that the molecule is substantially removed or separated from components with which it is naturally associated, or otherwise modified by a human hand, thereby excluding a PBP nucleic acid molecule as it exists in nature.

As used herein, the term "oligonucleotide" refers to a nucleic acid molecule that includes at least 15 contiguous nucleotides from a reference nucleotide sequence, and can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, up to 350 contiguous nucleotides from the reference nucleotide sequence. The reference nucleotide sequence can be the sense strand or the anti-sense strand. The oligonucleotide can be chemically synthesized or expressed recombinantly.

As used herein, a "modification" of a nucleic acid can include one or several nucleotide additions, deletions, or substitutions with respect to a reference sequence. A modification of a nucleic acid can include substitutions that do not change the encoded amino acid sequence due to the degeneracy of the genetic code. Such modifications can correspond to variations that are made deliberately, or which occur as mutations during nucleic acid replication. As such, a modification of a nucleic acid includes a substantially the same sequence, which is recognizable as related to a parent nucleic acid molecule such as the PBP nucleotide sequences disclosed herein. A substantially the same nucleotide sequence can hybridize to the reference nucleotide sequence under moderately stringent or higher stringency conditions.

Exemplary modifications of the PBP nucleic acid sequences disclosed herein include sequences that correspond to homologs of other species such as human, primates, rat, rabbit, bovine, porcine, ovine, canine, feline or other animal species. The sequences of corresponding PBPs of non-human species can be determined by methods known in the art, such as by polymerase chain reaction (PCR) or by screening genomic, cDNA or expression libraries. Another exemplary modification of PBP nucleic acid molecule can correspond to splice variant forms of the PBP nucleotide sequence. Additionally, a modification of a nucleotide sequence can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a modification of a nucleotide sequence can include, for example, a detectable moiety, such as a radiolabel, a fluorochrome, a ferromagnetic substance, a luminescent tag or a detectable binding agent such as biotin. Such modifications can be advantageous in applications where detection of a PBP nucleic acid molecule is desired.

As used herein, a "vector" refers to a recombinant DNA or RNA plasmid or virus that comprises a polynucleotide. A vector can include an expression element operationally linked to a polynucleotide such that the expression element controls the expression of the polynucleotide. An "expression element" is a nucleotide sequence involved in an interaction of molecules that contributes to the functional regulation of a polynucleotide, including replication, transcription, splicing, translation, or degradation of the polynucleotide. An expression element that controls transcription of a gene can be a promoter, the site of initiation of transcription, or an enhancer, a DNA sequence that increases the rate of transcription.

As used herein, the term "sample" is intended to mean a biological fluid, cell, tissue, organ or portion thereof, that includes or potentially includes a parkin binding protein nucleic acid or polypeptide. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can also be chemically synthesized, for example, by synthesizing degenerate oligonucleotides.

As used herein, the term "specifically hybridize" refers to the ability of a nucleic acid molecule to hybridize, under at least moderately stringent conditions or higher stringency conditions, as described herein, to a reference PBP nucleic acid molecule, without hybridization under the same conditions with nucleic acid molecules that are not the reference PBP nucleic acid molecule, for example, a negative control such as actin cDNA.

The invention provides an isolated parkin binding polypeptide (PBP), or functional fragment thereof. An exemplary parkin binding polypeptide includes the synapsin-like protein disclosed herein (see Example VIII). The isolated PBPs and peptides of the invention can be prepared by methods known in the art, including biochemical, recombinant and synthetic methods. For example, a PBP can be purified by routine biochemical methods from a cell or tissue source that expresses the corresponding transcript encoding the PBP or the PBP. The methods disclosed herein can be adapted for determining which cells and tissues, and which subcellular fractions therefrom, are appropriate starting materials. Biochemical purification can include, for example, steps such as solubilization of the appropriate tissue or cells, isolation of desired subcellular fractions, size, ion exchange, hydrophobic or affinity chromatography, electrophoresis, and immunoaffinity procedures. The methods and conditions for biochemical purification of a polypeptide of the invention can be chosen by those skilled in the art, and purification monitored, for example, by an immunological assay or a functional assay.

The invention also provides antibodies that specifically bind a parkin binding polypeptide (PBP). In a particular embodiment, the invention provides an antibody that specifically binds to the PBP having the amino acid sequence referenced as SEQ ID NO:2. As used herein, the term "antibody" is used in its broadest sense to include polyclonal and monoclonal antibodies, as well as antigen binding fragments of such antibodies. With regard to an antibody of the invention specific for a PBP, the term "antigen" means a native or synthesized PBP or fragment thereof.

An antibody specific for a PBP, or an antigen binding fragment of such an antibody, is characterized by having specific binding activity for a PBP or a peptide portion thereof of at least about $1\times10^5 M^{-1}$. Thus, Fab, $F(ab')_2$, Fd and Fv fragments of an antibody specific for a PBP, which retain specific binding activity for a PBP, are included within the definition of an antibody. Specific binding activity of a PBP can be readily determined by one skilled in the art, for example, by comparing the binding activity of an antibody to a PBP versus a control polypeptide that is not the PBP. One skilled in the art will readily understand the meaning of an antibody having specific binding activity for a particular PBP. The antibody can be a polyclonal or a monoclonal antibody. Methods of preparing polyclonal or monoclonal antibodies are well known to those skilled in the art (see, for example, Harlow and Lane, *Antibodies: A Laboratory Manual*, Cold Spring Harbor Laboratory Press (1988)). When using polyclonal antibodies, the polyclonal sera can be affinity purified using the antigen to generate mono-specific antibodies having reduced background binding and a higher proportion of antigen-specific antibodies.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989))). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988; Hilyard et al., *Protein Engineering: A practical approach* (IRL Press 1992); Borrabeck, *Antibody Engineering,* 2d ed. (Oxford University Press 1995)).

Antibodies specific for a PBP can be raised using an immunogen such as an isolated PBP, or a fragment thereof, which can be prepared from natural sources or produced recombinantly, or a peptide portion of the PBP that can function as an epitope. Such peptide portions of a PBP are functional antigenic fragments if the antigenic peptides can be used to generate an antibody specific for a PBP. A non-immunogenic or weakly immunogenic PBP or portion thereof can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art (see, for example, Harlow and Lane, supra, 1988). An immunogenic PBP fragment can also be generated by expressing the peptide portion as a fusion protein, for example, to glutathione S transferase (GST), polyHis, or the like. Methods for expressing peptide fusions are well known to those skilled in the art (Ausubel et al., *Current Protocols in Molecular Biology* (Supplement 47), John Wiley & Sons, New York (1999)).

The invention also provides a method of detecting a PBP by contacting a sample with an antibody that specifically binds a PBP and detecting specific binding of the antibody. An antibody specific for a PBP is therefore useful, for example, for determining the presence and/or level of a PBP in a sample. An antibody specific for a PBP is also useful for cloning a nucleic acid molecule encoding a gene encoding a polypeptide immunologically related to a PBP from an appropriate expression library, for example, a lambda gt11 library, or other type of expression library. An antibody specific for a PBP also can be used to substantially purify a PBP from a sample, for example, from a cell extract of a cell or tissue expressing a PBP or a cell extract from a cell expressing a PBP from a recombinant nucleic acid molecule.

Assays for detecting PBPs include, for example, immunohistochemistry, immunofluorescence, ELISA assays, radioimmunoassay, FACS analysis, immunoprecipitation, immunoblot analysis, and flow cytometry, using antibodies or antigen binding fragments specific for a PBP (Harlow and Lane, supra, 1988; Harlow and Lane, *Using Antibodies: A Laboratory Manual*, Cold Spring Harbor Press (1999)). Various immunoassays are well known in the art, and can be readily modified by those skilled in the art, as desired. For example, the antibody used in an immunological assay can be rendered detectable by incorporation of, or by conjugation to, a detectable moiety, or binding to a secondary molecule that is itself detectable or detectably labeled.

A PBP or an antibody specific for a PBP can be labeled so as to be detectable using methods well known in the art (Hermanson, *Bioconjugate Techniques*, Academic Press, 1996; Harlow and Lane, supra, 1988). For example, the peptide or antibody can be labeled with various detectable moieties including a radiolabel, an enzyme, biotin or a fluorochrome. Reagents for labeling a peptide or antibody can be included in a kit containing the peptide or antibody or can be purchased separately from a commercial source. The invention further provides a kit, which contains a PBP, an antibody specific for a PBP, or both. Such a kit also can contain a reaction cocktail that provides the proper conditions for performing an assay, for example, an ELISA or other immunoassay for determining the level of expression of a PBP in a sample, and can contain control samples that contain known amounts of a PBP and, if desired, a second antibody that can bind to an antibody specific for the PBP. Where the kit is to be used for an immunoassay, it can include a simple method for detecting the presence or amount of a PBP in a sample that is bound to the antibody.

The invention also provides an isolated nucleic acid molecule encoding a PBP amino acid sequence as disclosed herein, for example, the amino acid sequence referenced as SEQ ID NO:2. The invention also provides a modification of such a nucleic acid molecule. Such a nucleic acid molecule includes degenerate nucleotide sequences that encode the referenced amino acid sequence. Additionally, the invention provides an isolated PBP nucleic acid molecule comprising the nucleotide sequence referenced as SEQ ID NOs:1, 3 or 4, as well as a modification thereof. The invention additionally provides nucleic acid molecules having nucleotide sequences that encode a functional fragment of a PBP, as disclosed herein.

The invention also provides a modification of a PBP nucleotide sequence that hybridizes to a PBP nucleic acid molecule, for example, a nucleic acid molecule referenced as SEQ ID NO:1, 3 or 4, under at least moderately stringent conditions. Modifications of PBP nucleotide sequences, where the modification has at least 60% identity to a PBP nucleotide sequence, are also provided. The invention also provides modification of a PBP nucleotide sequence having at least 65% identity, at least 70% identity, at least 75% identity, at least 80% identity, at least 85% identity, at least 90% identity, at least 95% identity, at least 98% identity, or at least 99% identity to a PBP nucleic acid such as that referenced as SEQ ID NO:1, 3 or 4.

Moderately stringent conditions, as used herein, refers to hybridization conditions that permit a nucleic acid molecule to bind a nucleic acid that has substantial identity to a reference sequence. Moderately stringent conditions include conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 42° C. In contrast, "highly stringent conditions" include conditions equivalent to hybridization of filter-bound nucleic acid in 50% formamide, 5× Denhart's solution, 5×SSPE, 0.2% SDS at 42° C., followed by washing in 0.2× SSPE, 0.2% SDS, at 65° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderately stringent and highly stringent hybridization buffers and conditions, including varying salt and temperature conditions, are well known to those of skill in the art and are described, for example, in Sambrook et al., *Molecular Cloning: A Laboratory Manual*, 2nd ed., Cold Spring Harbor Press, Plainview, N.Y. (1989); and Ausubel et al., supra, 1999).

In general, a nucleic acid molecule that hybridizes to a recited sequence under moderately stringent conditions will have greater than about 60% identity, such as greater than about 70% identity or greater than about 80% identity to the reference sequence over the length of the two sequences being compared. A nucleic acid molecule that hybridizes to a recited sequence under highly stringent conditions will generally have greater than about 90% identity, including greater than about 95% identity, to the reference sequence over the length of the two sequences being compared. Identity of any two nucleic acid sequences can be determined by those skilled in the art based, for example, on a BLAST computer alignment, or similar methods for aligning sequences, using default parameters or other desired parameters (see, for example, Tatiana et al., *FEMS Microbiol Lett.* 174:247-250 (1999); Altschul et al., *J. Mol. Biol.* 215:403-410 (1990); Gish and States, (1993) *Nature Genet.* 3:266-272 (1993); Madden et al., *Meth. Enzymol.* 266:131-141 (1996); Altschul et al., *Nucleic Acids Res.* 25:3389-3402 (1997).

An isolated PBP nucleic acid molecule of the invention can be used in a variety of diagnostic and therapeutic applications. For example, an isolated PBP nucleic acid molecule of the invention, or a fragment thereof, can be used as a probe or to derive a probe or primers suitable for amplification of a PBP nucleic acid molecule or fragment thereof, as described herein; as a template for the recombinant expression of a parkin binding polypeptide; or in screening assays such as two-hybrid assays to identify cellular molecules that bind a PBP, similar to those used to the binding of a PBP to parkin (see Example I).

The invention also provides an oligonucleotide containing at least 15 contiguous nucleotides of a PBP nucleotide sequence disclosed herein, or the antisense strand thereof. The oligonucleotides of the invention that contain at least 15 contiguous nucleotides of a reference PBP nucleotide sequence are able to hybridize to under moderately stringent or higher stringency hybridization conditions to a PBP nucleic acid molecule and thus can be advantageously used, for example, as probes to detect a PBP DNA or RNA in a sample, or to detect splice variants thereof; as sequencing or PCR primers; as antisense reagents to block transcription of RNA in cells or to generate short interfering RNAs (siRNAs), as disclosed herein; or in other applications known to those skilled in the art in which hybridization to a PBP nucleic acid molecule is desirable.

It is understood that a PBP nucleic acid molecule, as used herein, specifically excludes previously known nucleic acid molecules consisting of nucleotide sequences having identity with a PBP nucleotide sequence, as disclosed herein, such as SEQ ID NO:1, 3 or 4, for example, Expressed Sequence Tags (ESTs), Sequence Tagged Sites (STSs) and genomic fragments, deposited in public databases such as the nr, dbest, dbsts, gss and htgs databases, which are available for searching on databases (Altschul et al., *Nucleic Acids Res.* 25:3389-3402 (1997)).

In a particular embodiment, the invention provides an oligonucleotide containing 20 to 200 contiguous nucleotides having 100% identity with nucleotides 796-955 of SEQ ID NO:1, or the antisense strand thereof. The oligonucleotide can contain at least 25, 30, 40, 50, 60, 70, 80, 90, 100, 125, 150, 175 contiguous nucleotides, and up to 200 contiguous nucleotides having 100% identity with nucleotides 896-955 of SEQ ID NO:1. Specifically excluded from oligonucleotides of the invention are nucleotide sequences corresponding to GenBank accession numbers BI041917; CD614598; CD614596; CD614594; CD614592; CD614590; CD614588; CD614576; CD614574; CD614570; BU542453; BF666086;

AW374529; BU687172; BM975158; BM910986; BG765308; BG745915; BG745175; BG698661; BG113587; BF837913; BE909317; BE899012; AL135049; AI143229, as well as other known sequences having identity with the nucleic acid molecules of the invention.

The PBP nucleic acid molecules and oligonucleotides of the invention can be produced or isolated by methods known in the art (see, for example, Sambrook et al., supra, 1989; Ausubel et al., supra, 1999). The method chosen will depend, for example, on the type of nucleic acid molecule desired. Those skilled in the art, based on knowledge of the nucleotide sequences disclosed herein, can readily isolate PBP nucleic acid molecules as genomic DNA, or can isolate desired introns, exons or regulatory sequences therefrom; as full-length cDNA or desired fragments therefrom; or as full-length mRNA or desired fragments therefrom, by methods known in the art.

One useful method for producing a PBP nucleic acid molecule of the invention involves amplification of the nucleic acid molecule using PCR and suitable oligonucleotides. Either PCR or RT-PCR can be used to produce a PBP nucleic acid molecule having desired nucleotide boundaries. Desired modifications to the nucleic acid sequence can also be introduced by choosing an appropriate oligonucleotide primer with one or more additions, deletions or substitutions. Such nucleic acid molecules can be amplified exponentially starting from as little as a single gene or mRNA copy, from any cell, tissue or species of interest.

The invention additionally provides a method of detecting a PBP nucleic acid molecule in a sample by contacting the sample with a PBP nucleic acid molecule or one or more oligonucleotides derived therefrom under conditions allowing specific hybridization to a PBP nucleic acid molecule, and detecting specific hybridization. The PBP nucleic acid molecule can be, for example, the PBP nucleotide sequence referenced as SEQ ID NO:1, 3 or 4 or an oligonucleotide derived therefrom containing at least 15 contiguous nucleotides of a reference PBP nucleotide sequence such as SEQ ID NO:1, 3 or 4. It is understood that such a PBP nucleic acid molecule or oligonucleotide derived therefrom can be the sense or anti-sense, as needed for the desired detection method.

The invention additionally provides a method of detecting a PBP nucleic acid molecule in a sample by contacting the sample with two or more oligonucleotides suitable for amplification of the desired nucleic acid molecule, amplifying a nucleic acid molecule, and detecting the amplification. The methods of detecting a PBP nucleic acid in a sample can be either qualitative or quantitative, as desired. For example, the presence, abundance, integrity or structure of a PBP nucleic acid can be determined, as desired, depending on the assay format and the probe or primer pair chosen.

Useful assays for detecting a PBP nucleic acid based on specific hybridization with an isolated PBP nucleic acid molecule are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Useful assays for detecting a PBP nucleic acid in a sample based on amplifying a PBP nucleic acid with two or more oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified PBP nucleic acid can be sequenced to detect mutations and mutational hot-spots, and specific assays for large-scale screening of samples to identify such mutations can be developed.

The invention further provides a kit containing a PBP nucleic acid molecule, for example, a PBP nucleotide sequence referenced as SEQ ID NO:1, 3 or 4 or a PBP oligonucleotide of the invention. For example, the diagnostic nucleic acids can be derived from any portion of a PBP nucleic acid molecule such as SEQ ID NO:1, 3 or 4 or an anti-sense strand thereof. Kits of the invention are useful as diagnostic systems for assaying for the presence or absence of nucleic acid encoding a PBP in either genomic DNA, mRNA or cDNA. A suitable diagnostic system includes at least one invention nucleic acid and can contain two or more invention nucleic acids as a separately packaged chemical reagent(s) in an amount sufficient for at least one assay. Instructions for use of the packaged reagent are also typically included. Those of skill in the art can readily incorporate invention nucleic acid probes and/or oligonucleotides useful as primers into kit form in combination with appropriate buffers and solutions for the practice of the invention methods as described herein.

The PBP nucleic acid molecules of the invention can be used to screen for nucleic acid molecules related to a PBP nucleic acid molecule. Nucleic acid molecules related to a PBP nucleic acid molecule can be identified, for example, by screening a library, such as a genomic library, cDNA library or expression library, with a detectable agent. Such libraries are commercially available or can be produced from any desired tissue, cell, or species of interest using methods known in the art. For example, a cDNA or genomic library can be screened by hybridization with a detectably labeled PBP nucleic acid molecule. Additionally, an expression library can be screened with an antibody raised against a polypeptide corresponding to the coding sequence of a PBP nucleic acid. The library clones containing PBP nucleic acid molecules of the invention can be isolated from other clones by methods known in the art and, if desired, fragments therefrom can be isolated by restriction enzyme digestion and gel electrophoresis.

The invention also provides a vector containing a PBP nucleic acid molecule. The vectors of the invention are useful for subcloning and amplifying a PBP nucleic acid molecule and for recombinantly expressing a PBP polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

The invention additionally provides a host cell containing a vector comprising a PBP nucleic acid molecule. Exemplary host cells that can be used to express recombinant PBP molecules include mammalian primary cells; established mammalian cell lines, such as COS, CHO, HeLa, NIH3T3, HEK 293 and PC12 cells; amphibian cells, such as *Xenopus* embryos and oocytes; and other vertebrate cells. Exemplary host cells also include insect cells such as *Drosophila*, yeast cells such as *Saccharomyces cerevisiae, Saccharomyces pombe*, or *Pichia pastoris*, and prokaryotic cells such as *Escherichia coli*.

The invention also provides methods of identifying molecules that modulate expression and/or activity of a PBP. These molecules can be used, for example, in therapeutic applications to promote or inhibit a biological function of a PBP.

Various binding assays to identify cellular proteins that interact with protein binding domains are known in the art and include, for example, yeast two-hybrid screening assays. (see, for example, U.S. Pat. Nos. 5,283,173, 5,468,614 and 5,667,973; Ausubel et al., supra, 1999; Luban et al., *Curr. Opin. Biotechnol.* 6:59-64 (1995)), which, as disclosed herein, was used to identify exemplary parkin binding polypeptides (PBPs). Other methods include affinity column chromatography methods using cellular extracts. By synthesizing or expressing polypeptide fragments containing various PBP sequences or deletions, the PBP binding interface can be readily identified.

The invention also provides a method of identifying molecules, such as PBP modulatory compounds, that modulate PBP expression and/or activity. A PBP modulatory compound is a molecule that specifically binds a PBP nucleic acid molecule or PBP and alters its expression or activity. A PBP modulatory compound can be a naturally occurring macromolecule, such as a peptide or polypeptide, nucleic acid, carbohydrate, lipid, or any combination thereof. A PBP modulatory compound also can be a partially or completely synthetic derivative, analog or mimetic of such a macromolecule, or a small organic or inorganic molecule prepared partly or completely by combinatorial chemistry methods. An exemplary PBP modulatory compound includes an inhibitor, as disclosed herein. Methods for producing pluralities of compounds to use in screening for PBP modulatory compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art, as described herein.

A variety of low- and high-throughput assays known in the art are suitable for detecting specific binding interactions between a PBP nucleic acid molecule or polypeptide and a candidate PBP modulatory compound. Both direct and competitive assays can be performed, including, for example, fluorescence correlation spectroscopy (FCS) and scintillation proximity assays (SPA) (reviewed in Major, *J. Receptor Signal Transduction Res.* 15:595-607 (1995); and in Sterrer et al., *J. Receptor Signal Transduction Res.* 17:511-520 (1997)). Assays for detecting specific binding interactions can include affinity separation methods using a PBP-specific ligand, for example, an antibody used in ELISA assays, FACS analysis or affinity separation.

Assays to identify compounds that modulate gene expression of a PBP can involve first transducing cells with a PBP promoter-reporter nucleic acid construct such that a change in expression of a protein such as β-lactamase, luciferase, green fluorescent protein or β-galactosidase will be detected in response to contacting the cell with a PBP modulatory compound that upregulates or downregulates expression of a PBP. Such assays and reporter systems are well known in the art and are described, for example, in Ausubel et al., supra, 1999.

Other assays to identify compounds that modulate gene expression of a PBP include assays that measure levels of PBP transcripts, such as Northern blots, RNase protection assays, and RT-PCR. Methods of identifying a promoter and/or enhancer from genomic DNA encoding a PBP are well known in the art. A reporter gene construct can be generated using the promoter region of PBP gene and screened for compounds that increase or decrease PBP gene promoter activity. Such compounds can also be used to alter PBP expression.

Assays to identify compounds that modulate expression of a PBP can involve detecting a change in PBP abundance in response to contacting the cell with a PBP modulatory compound. Assays for detecting changes in polypeptide expression include, for example, immunoassays with specific PBP antibodies, such as immunoblotting, immunofluorescence, immunohistochemistry and immunoprecipitation assays.

Appropriate assays to determine whether a PBP modulatory compound inhibits or promotes a PBP activity can be determined by those skilled in the art based on a biological activity of the PBP. For example, a PBP can be screened with various compounds, as described above, to identify a PBP modulatory compound that alters expression of a PBP nucleic acid or a PBP or that alters a biological activity of a PBP.

The polypeptides and nucleic acid molecules of the invention can be used in various diagnostic or therapeutic applications. The diagnostic and therapeutic applications can be based on a biological activity of a PBP. For example, a PBP nucleic acid molecule can be used in therapeutic methods to treat an individual having an altered PBP activity. The loss of parkin function in patients with AR-JP can alter the function of a PBP, such as synaptotagmin 1 or 11 or SLP. Since parkin ubiquitinates PBPs, a loss of parkin function can serve to increase expression of a PBP. In a therapeutic method, an altered PBP activity that is increased relative to normal PBP expression can be decreased by administering a PBP antisense nucleic acid or siRNA, as disclosed herein.

A vector containing nucleic acid molecule to inhibit expression of a PBP can be introduced into an individual by in vivo or ex vivo methods to decrease expression of a PBP. Vectors useful for such therapeutic methods include, for example, retrovirus, adenovirus, lentivirus, herpesvirus, poxvirus DNA or any viral DNA that allows expression of a heterologous polynucleotide of interest. Other vectors can also be employed, for example, DNA vectors, pseudotype retroviral vectors, adeno-associated virus, gibbon ape leukemia vector, vesicular stomatitis virus (VSV), VL30 vectors, liposome mediated vectors, and the like.

PBP modulatory compounds can also be used in therapeutic methods. For example, a PBP modulatory compound can be used to alter the expression or activity of a PBP that is aberrantly expressed, for example, having increased expression resulting from a loss of parkin function. For example, increased expression of a PBP can be reduced with a PBP modulatory compound that decreases expression and/or activity of the PBP.

The invention further provides a method of generating an animal model of Parkinson's disease by generating a transgenic animal expressing an increased level of a parkin binding polypeptide. The parkin binding polypeptide can be selected from synaptotagmin I, synaptotagmin XI, or synpasin-like protein. The invention additionally provides an animal model of Parkinson's disease generated by such a method.

The present invention further provides transgenic non-human mammals that are capable of expressing exogenous nucleic acids encoding a PBP. Since the loss of parkin leads to decreased ubiquitination of PBPs and therefore increased expression, expression of a PBP in a transgenic non-human mammal can serve as an animal for at least some aspects of Parkinson's disease. The PBP transgene can be targeted to a cell or tissue known to express the PBP, as disclosed herein (see Examples VI-VIII). An exogenous nucleic acid refers to a nucleic acid sequence which is not native to the host, or which is present in the host in other than its native environment, for example, as part of a genetically engineered DNA construct. In addition to naturally occurring levels of PBP, a PBP of the invention can either be overexpressed, as discussed above, or underexpressed in transgenic mammals, for example, as in the well-known knock-out transgenics.

Also contemplated herein is the use of homologous recombination of mutant or normal versions of a PBP gene with the native gene locus in transgenic animals to alter the regulation of expression or the structure of a PBP by replacing the endogeneous gene with a recombinant or mutated PBP gene. Methods for producing a transgenic non-human mammal, including a gene knock-out non-human mammal, are well known to those skilled in the art (see, Capecchi et al., *Science* 244:1288 (1989); Zimmer et al., *Nature* 338:150 (1989); Shastry, *Experentia,* 51:1028-103.9 (1995); Shastry, *Mol. Cell. Biochem.,* 181:163-179 (1998); and U.S. Pat. No. 5,616, 491, issued Apr. 1, 1997, U.S. Pat. No. 5,750,826, issued May 12, 1998, and U.S. Pat. No. 5,981,830, issued Nov. 9, 1999).

Also provided are transgenic non-human mammals capable of expressing nucleic acids encoding a PBP so mutated as to be incapable of normal activity and which, therefore, do not express native PBP. The present invention also provides transgenic non-human mammals having a genome comprising antisense nucleic acids complementary to nucleic acids encoding a PBP, placed so as to be transcribed into antisense mRNA complementary to mRNA encoding a PBP, which hybridizes, to the mRNA and, thereby, reduces the translation thereof. The nucleic acid can additionally comprise an inducible promoter and/or tissue specific regulatory elements, so that expression can be induced, or restricted to specific cell types. An example of a non-human transgenic mammal is a transgenic mouse. Examples of tissue specificity-determining elements are the metallothionein promoter and the L7 promoter.

Animal model systems that elucidate the physiological and behavioral roles of a PBP are also provided and are produced by creating transgenic animals in which the expression of the PBP is altered using a variety of techniques. Examples of such techniques include the insertion of normal or mutant versions of nucleic acids encoding a PBP by microinjection, retroviral infection or other means well known to those skilled in the art, into appropriate fertilized embryos to produce a transgenic animal (see, for example, Hogan et al., *Manipulating the Mouse Embryo: A Laboratory Manual* (Cold Spring Harbor Laboratory, (1986)).

As discussed herein, parkin functions as an E3 ubiquitin ligase. Parkin was found to ubiquitinate synaptotagmins 1 and 11. Inactivating mutations of the parkin gene cause autosomal recessive juvenile parkinsonism. Inactivation of parkin therefore can affect the ability of parkin interacting polypeptides to be processed, for example, by ubiquitination. It is possible that mimicking the activity of parkin, that is decreasing an activity of a parkin interacting polypeptide, can be used to ameliorate a sign or symptom associated with Parkinson's disease. One skilled in the art can readily recognize or determine the amelioration of a sign or symptom associated with Parkinson's disease.

Methods of decreasing an activity of a polypeptide are well known to those skilled in the art. It is understood that a decrease in activity of a polypeptide includes both decreasing the expression level of the polypeptide as well as decreasing a biological activity exhibited by the polypeptide.

Methods for decreasing the expression of a polypeptide can include, for example, the use of ribozymes, antisense nucleic acids or RNA interference. RNA interference has been described previously (Fire et al., *Nature* 391:806-811 (1998). In RNA interference as it occurs naturally, during the initiation step, input dsRNA is digested into 21-23 nucleotide small interfering RNAs (siRNAs), which have also been called "guide RNAs" as described in Hammond et al. *Nature Rev Gen* 2: 110-119 (2001); Sharp, *Genes Dev* 15: 485-490 (2001); and Hutvagner and Zamore, *Curr Opin Genetics & Development* 12:225-232 (2002). The siRNAs are produced when an enzyme belonging to the RNase III family of dsRNA-specific ribonucleases progressively cleaves dsRNA, which can be introduced directly or via a transgene or vector. Successive cleavage events degrade the RNA to 19-21 base pair duplexes (siRNAs), each with 2-nucleotide 3' overhangs as described by Hutvagner and Zamore, *Curr. Opin. Genetics & Development* 12:225-232 (2002); Bernstein et al., *Nature* 409:363-366 (2001). In the effector step, the siRNA duplexes bind to a nuclease complex to form what is known as the RNA-induced silencing complex, or RISC. The active RISC then targets the homologous transcript by base pairing interactions and cleaves the mRNA approximately 12 nucleotides from the 3' terminus of the siRNA (Nykanen et al., *Cell* 107:309-321 (2001)).

A parkin interacting polypeptide activity can also be decreased using an inhibitor. An inhibitor can be a compound that decreases expression, activity or intracellular signaling of a parkin interacting polypeptide. Such an inhibitor can be, for example, a small molecule, protein, peptide, peptidomimetic, ribozyme, nucleic acid molecule or oligonucleotide, oligosaccharide, or combination thereof. Methods for generating such molecules are well known to those skilled in the art (Huse, U.S. Pat. No. 5,264,563; Francis et al., *Curr. Opin. Chem. Biol.* 2:422-428 (1998); Tietze et al., *Curr. Biol.,* 2:363-371 (1998); Sofia, *Mol. Divers.* 3:75-94 (1998); Eichler et al., *Med. Res. Rev.* 15:481-496 (1995); Gordon et al., *J. Med. Chem.* 37: 1233-1251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997)). Libraries containing large numbers of natural and synthetic compounds also can be obtained from commercial sources. Combinatorial libraries of molecules can be prepared using well known combinatorial chemistry methods, as discussed above. An inhibitor can include, for example, an antagonist; a dominant negative molecule that prevents activation of a parkin interacting polypeptide; antibodies, proteins, small molecules and oligonucleotides that inhibit an activity or expression of a parkin interacting polypeptide; ribozymes, antisense nucleic acid molecules, and nucleic acid molecules encoding negative regulatory transcription factors that prevent or reduce parkin interacting polypeptide expression, as well as cells or viruses containing such ribozymes and nucleic acid molecules. One skilled in the art will readily understand that these and other molecules that inhibit parkin interacting polypeptide expression, activity or signaling can be used as an inhibitor.

A sequence-specific ribonuclease such as a ribozyme or an antisense nucleic acid molecule can also be used to inhibit the expression of a parkin interacting polypeptide. A sequence-specific ribonuclease refers to a molecule that catalyzes the cleavage of RNA at a defined ribonucleotide sequence. A ribozyme refers to an RNA molecule that catalyzes the cleavage of RNA at a defined ribonucleotide sequence. Ribozymes such as hammerheads and hairpins can be designed and prepared by routine methods. The specificity of ribozymes such as hammerheads and hairpins for a target cleavage site is determined by base-pairing between the ribozyme and its RNA target. Methods of designing ribozymes are well known as described, for example, in Hauswirth and Lewin, *Prog. Retin. Eye Res.* 19:689-710 (2000), and Lewin and Hauswirth, *Trends. Mol. Med.* 7:221-228 (2001).

Sequence-specific ribonucleases, including ribozymes and DNA enzymes, can be designed as described above and prepared by standard methods for synthesis of nucleic acid molecules. See, also, Ke et al., *Int. J. Oncol.* 12:1391-1396 (1998); Doherty et al., *Ann. Rev. Biophys. Biomol. Struct.* 30:457-475 (2001); Hauswirth and Lewin, supra, 2000; and Lewin and Hauswirth, supra, 2001. Sequence-specific ribozymes also can be identified by in vitro selection from pools of random sequences. Such methods are well-established, as described, for example, in Bartel and Szostak, *Science* 261:1411-1418 (1993), Breaker, *Chem. Rev.* 97:371-390 (1997) and Santoro and Joyce, *Proc. Natl. Acad. Sci., USA* 94:4262-4266 (1997)).

Where a ribozyme is to be administered to a patient without being delivered using a viral or other vector, the ribozyme can be modified, if desired, to enhance stability. Modifications useful in a therapeutic ribozyme include, but are not limited to, blocking the 3' end of the molecule and the 2' positions of pyrimidines. Stabilized ribozymes can have half-lives of hours and can be administered repeatedly using, for example, intravenous or topical injection. Those skilled in the art understand that a ribozyme also can be administered by expression in a viral gene therapy vector. A DNA oligonucleotide encoding the ribozyme can be cloned downstream of a ERA pol II or RNA pol III promoter and, if desired, can be embedded within the transcripts of genes such as tRNAval, U6 snRNA or the adenoviral VA1 RNA.

An antisense nucleic acid molecule refers to a nucleic acid molecule that is complementary in sequence to all or part of a molecule of messenger RNA or another specific RNA transcript. An antisense nucleic acid molecule can be, for example, DNA or RNA, and can include naturally occurring nucleotides as well as synthetic nucleotides or other non-naturally occurring modifications such as modifications to the phosphate backbone that improve stability. Antisense oligonucleotides, including phosphorothioate and other modified oligonucleotides, are encompassed by the term antisense nucleic acid molecule as used herein. Without being bound by the following, an antisense nucleic acid molecule useful in the invention can reduce mRNA translation or increase mRNA degradation, thereby reducing expression of the target mRNA.

The homology requirement for reduction of expression using antisense methodology can be determined empirically. Generally, at least about 80-90% nucleic acid sequence identity is present in an antisense nucleic acid molecule useful in the invention, with higher nucleic acid sequence identity often used in antisense oligonucleotides, which can be perfectly identical to the patient's endogenous transcript. The target sequence can be chosen, if desired, to have a small single-stranded region at which nucleation takes place, in addition to a double-stranded, helically ordered stem that is invaded by the antisense molecule to displace one of the strands (Mir and Southern, *Nature Biotech.* 17:788-792 (1999). Methods for selecting and preparing antisense nucleic acid molecules are well known in the art and include in silico approaches (Patzel et al. *Nucl. Acids Res.* 27:4328-4334 (1999); Cheng et al., *Proc. Natl. Acad. Sci., USA* 93:8502-8507 (1996); Lebedeva and Stein, *Ann. Rev. Pharmacol. Toxical.* 41:403-419 (2001); Juliano and Yoo, *Curr. Opin. Mol. Ther.* 2:297-303 (2000); and Cho-Chung, *Pharmacol. Ther.* 82:437-449 (1999)).

One skilled in the art can readily determine a decrease in activity or expression of a parkin binding polypeptide. For example, nucleic acid probes or primers can be used to examine expression of a parkin interacting polypeptide mRNA, and parkin interacting polypeptide antibodies can be used to examine expression levels of the polypeptide. The effect of an inhibitor can be readily determined by assaying its effect on a biological activity of a parkin interacting polypeptide. For example, an activity of a synaptotagmin can be determined (Sudhof, *J. Biol. Chem.* 277:7629-7632 (2002)). These and other suitable methods, which can be readily determined by those skilled in the art, can be used to test the effect of a compound as a potential inhibitor of a parkin interacting polypeptide. Compounds can also be screened for the ability to increase ubiquitination of a parkin interacting polypeptide to compensate for a decrease in parkin ubiquitination activity in Parkinson's disease.

The invention provides, in another embodiment, a method of identifying a candidate drug for treating Parkinson's disease by contacting a parkin binding polypeptide with one or more compounds and identifying a compound that alters the activity of the parkin binding polypeptide. Exemplary parkin binding polypeptides include synaptotagmin I, synaptotagmin XI, and synpasin-like protein. The method can be used to screen for a compound that decreases the activity of the parkin binding polypeptide.

The invention further provides a method of identifying a candidate drug for treating Parkinson's disease by contacting a cell expressing a parkin binding polypeptide with one or more compounds and identifying a compound that decreases the expression of the parkin binding polypeptide. In another embodiment, the invention provides a method of treating Parkinsons's disease by administering a molecule that decreases expression or activity of a parkin binding polypeptide. Such a molecule can be identified by the methods disclosed herein.

It is understood that modifications which do not substantially affect the activity of the various embodiments of this invention are also provided within the definition of the invention provided herein. Accordingly, the following examples are intended to illustrate but not limit the present invention.

EXAMPLE I

Identification of Parkin Interacting Polypeptides by the Yeast

This example describes the identification of polypeptides that interact with parkin using the yeast two-hybrid system.

The yeast two-hybrid method was used to screen a human fetal brain pGAD10-cDNA library using the pGBT9-parkin (1-465) construct (Fields and Song, *Nature* 340:245-246 (1989)). To prepare the yeast two-hybrid bait plasmid pGBT9-parkin(1-465), the full-length parkin cDNA encoding amino acids 1-465 was excised from pEGFPC1-parkin (Huynh et al *Ann. Neurol.* 48:737-744 (2000)) and ligated into the pGBT9 plasmid (Clontech; Palo Alto Calif.).

To identify parkin interacting proteins, a yeast two-hybrid screen of a human adult brain cDNA library cloned in the GAL4 activation domain vector pGAD10 was performed using as bait pGBT9-parkin(1-465), encoding parkin amino acids 1-465 fused to the GAL4 binding domain (vectors and library from Clontech). As previously described (Shibata et al., *Hum. Mol. Genet.* 9:1303-1313 (2000) and Scoles et al., *Nat. Genet.* 18:354-359 (1998)), the bait plasmid was cotransformed in yeast strain Y190 and grown on synthetic media without leucine, tryptophan, and histidine, and with 25 mM 3-amino-1,2,4-triazole and 2% glucose. The Y190 strain allows for nutritional selection of the HIS3 gene that allows growth in media lacking histidine and color selection using the LacZ gene encoding β-galactosidase. The β-galactosidase reporter was assayed on stamped nitrocellulose filters by incubating freeze-fractured colonies in Z-buffer (60 mM $Na_2HPO_4$, 40 mM $NaH_2PO_4$, 10 mM KCl, 1 mM $MgSO_4$, pH 7.0, 0.03 mM β-mercaptoethanol, and 2.5 µM X-gal) at 37° C. for 15 min to 8 hr. Positive clones were restreaked on synthetic media without leucine or tryptophan, and retested for β-galactosidase activity, and then pGAD10. "prey" plasmids were isolated.

A pGAD10 plasmid containing a partial sequence encoding the human synaptotagmin 11 gene was purified and then retransformed with pGBT9-parkin(1-465) or negative control plasmids (pGBT9 vector, pGBT9-NF2, pGBT9-HRS) and retested for β-galactosidase activity. To obtain semi-quantitative estimates of interaction strengths between various parkin and synaptotagmin 11 protein fragments, liquid assays for β-galactosidase were conducted by incubating Y190 yeast cells extracted in Z-buffer and 5% chloroform with 0.6 mg/ml o-nitrophenylgalactoside for 2 min to 1 hour. Standard deviations were calculated from triplicate measures of replicate cultures. β-Galactosidase activity was expressed as Miller units (Miller unit=1000×[$OD_{420}$/($OD_{600}$×time× volume)] (Poullet and Tamanoi *Methods Enzymol.* 255:488-497 (1995)).

Six potential clones were identified in $2 \times 10^6$ independent human fetal brain pGAD10-cDNA colonies. These clones were individually isolated, sequenced, and subjected to further yeast two-hybrid filter assays to confirm the interactions. Two of these clones had a long open-reading frame and therefore were purified and sequenced. Nucleotide sequences showed that one of the two clones encoded the C2A and C2B domains of synaptotagmin 11, and this clone was designated hsyt11AB (for human synaptotagmin 11, domains C2A and C2B). To further determine if the hsyt11AB fragment was a true parkin interactor, the purified pGAD10-hsyt11AB was co-transfected into Y190 yeast cells with either pGBT9-parkin(1-465), or with two unrelated baits, pGBT9-NF2 (encoding the schwannomin tumor suppressor), and pGBT9-Hrs (encoding hepatocyte growth factor regulated kinase substrate) constructs (Scoles et al., supra 2000) or the pGBT9 vector. Filter binding assays demonstrated that the pGAD10-hystXIAB clone showed positive interaction with the pGBT9-parkin construct but not with the pGBT9 vector control or unrelated proteins (FIG. 1A).

Parkin was found to interact with the $C_2A$ and $C_2B$ domains of syt11. FIG. 1A shows a yeast two-hybrid filter assay. Yeast Y190 cells transformed with pGAD10-hsyt11AB and pGBT9-parkin produced a positive reaction with β-galactosidase substrate (gray patches), while yeast cells transformed with pGAD10-hsyt11AB and the pGBT9-vector control did not (FIG. 1A). Yeast cells transformed with pGAD10-hsyt11ANTIBODY and two other controls expressing neurofibromin and Hrs (pGBT9-NF1, and pGBT9-Hrs) failed to form positive reaction with the β-galactosidase substrate. These controls proteins are functional in the yeast two-hybrid system as previously described (Scoles et al., supra (1998)). These filter binding assays showed that only the pGAD10-hsyt11AB clone showed positive interaction with the pGBT9-parkin construct but not with the pGBT9 vector control or unrelated proteins (FIG. 1A).

To confirm parkin interaction by yeast two-hybrid liquid assays, triplicates of single transfected yeast colonies were grown in liquid culture and tested for β-galactosidase activity. Yeast cells co-transfected with pGAD10-hsyt11AB and pGBT9-parkin produced about 20-fold higher β-galactosidase activity ("1" in FIG. 1B) compared with yeast cells co-expressing pGAD10-hsyt11AB and pGBT9 vector control ("12" in FIG. 1B). Each bar graph shown in FIG. 1B represents n=3.

These results demonstrate that parkin interacts with the C2A and C2B domains of synaptotagmin 11 (syt11).

EXAMPLE II

Generation and Specificity of Antibodies to Synaptotagmins 1 and 11

This example describes the production and characterization of synaptotagmin 1 and 11 antibodies.

To generate anti-synaptotagmin 11 antibodies, the rabbit anti-syt11 antibody was made against the sytXIA peptide (HQQAEKKQKNPPYKF; SEQ ID NO:9) by QCP. Another antibody against the sytXIB peptide (KVRRDKDGPRRES-GRG; SEQ ID NO:10) was made, but this antibody recognized multiple bands in western blots of human and PC12 cells protein extracts. The anti-sytXIA antibody was affinity purified by a Sepharose™ sytXIA column. The rabbit and chicken anti-parkin was made against peptide ParkA as described previously (Huynh et al, *Ann. Neurol.* 48:737-744 (2000)).

Rabbit antibodies to three peptides of synaptotagmin 11 (anti-syt11) were generated. A mouse antibody to synaptotagmin 1 (anti-syt65) was purchased (Stressgen; Victoria, British Columbia, Canada). Mouse monoclonal antibodies to β-actin (Sigma) and β-COP (Sigma), and rabbit ubiquitin antibody (DAKO; Carpinteria CA) were purchased. Since syt1 and syt11 are related proteins and have close homology to at least 11 other synaptotagmins, the anti-syt65 and anti-syt11 antibodies were tested for cross-reactivity with the other antigens before using these antibodies to investigate parkin-syt interactions.

For protein extraction, cells were extracted with CO-IP buffer (20 mM Hepes, pH 7.2, 150 mM NaCl, 0.5% Triton X100) at a predetermined time point after transfection. For ubiquitination assays and antibody analysis, cells or tissues were extracted with strong triple detergent buffer (20 mM Hepes, pH 7.2, 150 mM NaCl, 1% Triton X-100, 0.1% SDS, 0.5% deoxycholate). The protein extracts were clarified by 30 minutes centrifugation using a table-top Beckmann Microfuge (Beckman Coulter; Fullerton Calif.). For western blot analysis, 10 µl of the protein extract was loaded per well of a 15-well, 4-20% gradient, mini sodium dodecl sulfate (SDS)-polyacrylamide gel. Proteins were resolved at 100V for 2 hours and transferred to Amersham's nitrocellulose filter overnight at 30V in the cold room (Amersham; Piscataway N.J.). The filter was then removed from the Western blot apparatus and blocked with 5% nonfat milk for 1 hour at room temperature. The blocking solution was then replaced with blocking solution containing the desired concentration of primary antibody. The western blot was visualized with the Amersham Chemiluminescent Western blot detection kit.

Figure 2:
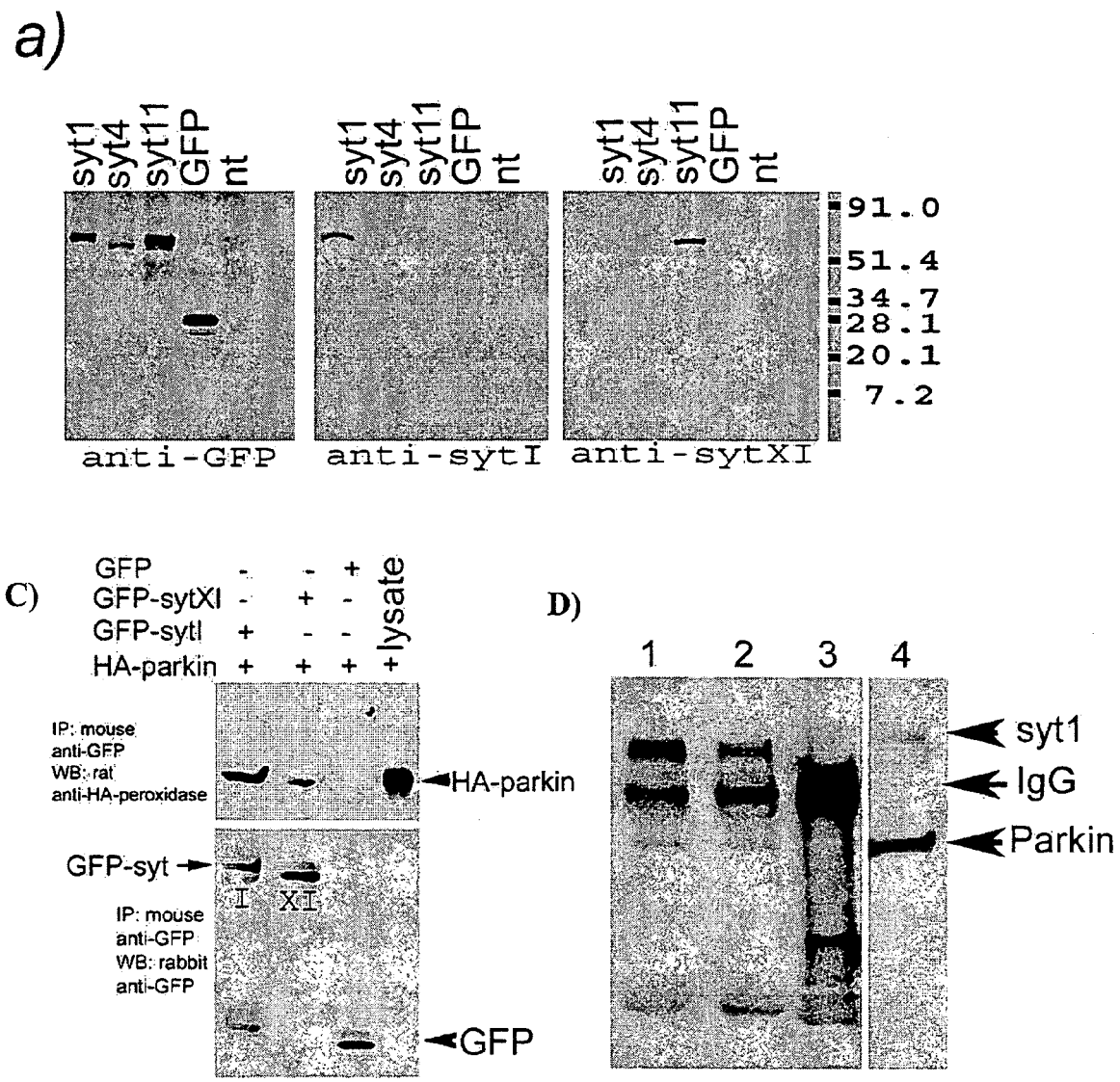
FIG. 2A shows the specificity of antibodies to synaptotagmins 1 and 11. Western blots of protein extracts from HEK293 cells transfected with green fluorescent protein (GFP) and GFP-syt1, 4, and 11 plasmids were detected with antibodies to GFP, syt1, and syt11. The lane marked "Int" were loaded with non-transfected cells.
FIG. 2B shows western blots of protein extract from PC12 cells detected with rabbit anti-sytXIA antibody. Lane 1, incubation with 1 µg/ml of anti-sytXIA antibody; lane 2, incubation with anti-sytXIA antibody preincubated with sytXIA peptide; lane 3, incubation with anti-syXIA antibody preincubated with sytXIB peptide. The anti-sytXIA antibody detects a single band at 64 kDa. This band was preabsorbed out with preincubation with the sytXIA peptide but not with sytXIB peptide.
FIG. 2C shows in vitro interaction of GFP-syt1 and syt 11 with hemaglutinin-parkin (HA-parkin). Protein extracts from HEK293 cells overexpressing HA-parkin and the corresponding GFP fusion proteins were communoprecipitated with a mouse anti-GFP antibody. The immunoprecipitation products were detected with rat anti-HA-peroxidase (top panel) and a rabbit anti-GFP antibody (bottom panel).
FIG. 2D shows in vivo interaction of endogenous parkin with symatotagmin 1 in PC12 cells. Co-ip of protein extracts from PC12 cells with 5 µl (lane 1) and 1 µl (lane 2) mouse anti-syt1, and 1 µl mouse IgG (lane 3). Co-IP products were detected with rabbit anti-parkin and mouse anti-syt1 antibodies simultaneously. Lane 4 shows a blot of the PC12 protein lysate.
FIG. 2E shows co-immunoprecipitation of endogenous parkin and sytXIA. Protein extracts from a human cerebral cortex were coimmunoprecipitated with rabbit anti-parka antibody (lane 1), or rabbit IgG (lane 2) as a control. The precipitates were detected with anti-parka (top panel) or anti-sytXIA antibody (bottom panel). The anti-parka antibody co-immunoprecipitated sytXI but the rabbit IgG control did not. To do the reverse co-ip, protein extracts were co-ip with rabbit anti-sytXI antiserum (lane 3) or the corresponding preserum at identical dilutions (lane 4). The western blot was detected with the chicken anti-parka (lanes 3 and 4), which detected the endogenous parkin band in the anti-sytXI antiserum (lane 3), but not in the preserum control (lane 4).

Rabbit antibodies to two peptides of synaptotagmin XI (anti-sytXIA and anti-sytXIB) were generated, and a mouse antibody to synaptotagmin 1 (anti-syt65) was purchased. Since sytI and sytXI are related proteins and have close homology to other synaptotagmins, the anti-syt65 and anti-sytXI antibodies were tested for cross-reactivity with the respective antigens before using these antibodies to investigate parkin-sytXI interactions. FIG. 2A shows the specificity of antibodies to synaptotagmins 1 and 11 using immunoblotting (Western blotting). Protein extracts were isolated from human embryonic kidney (HEK) 293T cells expressing GFP-syt1, GFP-syt4, GFP-syt11, or GFP. Western blots of protein extracts from HEK293 cells transfected with GFP or GFP-syt1, 4, and 11 plasmids were detected with antibodies to GFP, syt1, and syt11 (FIG. 2A). The western blots were separately detected with anti-GFP, anti-syt65 or anti-sytXIA antibodies. Both the anti-syt1 and anti-syt11 antibodies specifically detected their respective epitope but not the GFP-syt4 fusion protein. As expected, both the anti-syt65 and anti-syt11 antibodies detected only the respective GFP-syt1 or GFP-syt11 proteins, while the anti-GFP antibodies detected all GFP-tagged proteins. The anti-syt11 antibody did not detect the GFP-syt4, even through syt4 has the closest homology with syt11. The lanes indicated in FIG. 2A as "nt" were non-transfected cells. The positions of molecular weight markers are indicated on the right.

Figures 2B, 2E:
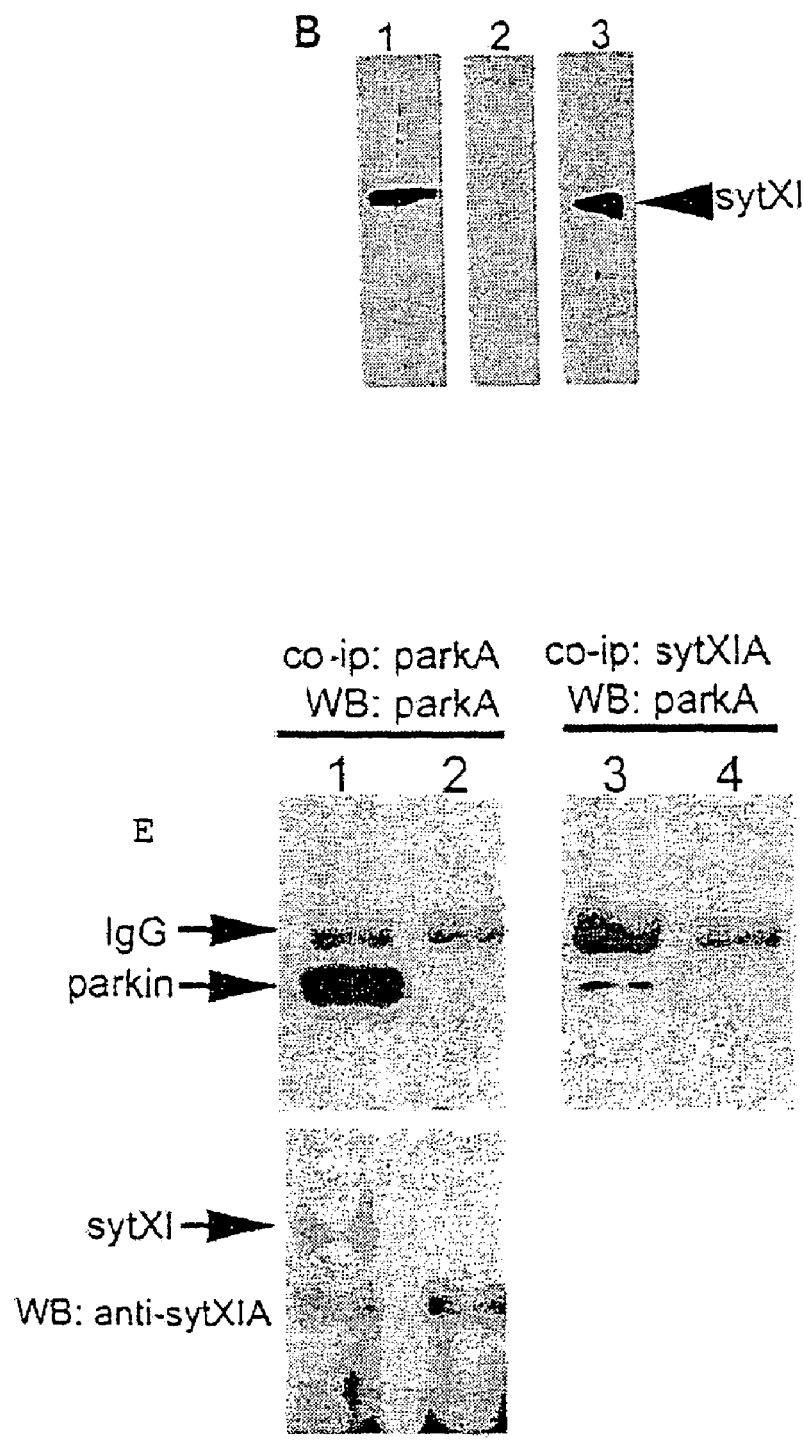

The specificity of the sytXIA antibody was further confirmed in western blots of protein extracts from PC12 cells (FIG. 2B). PC12 cell protein extracts in strong triple detergent buffer were immunoblotted with anti-sytXIA, anti-sytXIA preabsorbed with sytXIA peptide, or with sytXIB peptide. The antisytXIA antibody recognized a single band at 64 kDa (FIG. 2B, lane 1). The p64 band was not detected when the anti-sytXIA antibody was preabsorbed with the sytXIA peptide (FIG. 2B, lane 2), while preabsorption with a different peptide (sytXIB) failed to inhibit the anti-sytXIA immunoreactivity (FIG. 2B, lane 3). Taken together, these observations further confirm the specificity of the anti-sytXIA antibody. Western blots of protein extracts isolated using weak detergent buffer (0.2 or 0.5% NP40 or Triton-X100) gave two sytXI positive bands at 64 and 110 kDa, suggesting that sytXI may form homodimers.

These results confirm the specificity of the anti-syt11 antibody.

EXAMPLE III

Parkin Interacts with the Full-length Synaptotagmins 1 and 11

This example describes co-immunoprecipitation experiments showing that parkin interacts with full-length synaptotagmins 1 and 11.

Co-immunoprecipitation of 293T cells coexpressing the GFP-hsyt11AB fusion protein and hemaglutinin-parkin (HA-parkin) found that parkin co-precipitated the hsyt11AB fragment. To determine whether parkin interacted with the full-length synaptotagmin, the full-length synaptotagmin 1 (syt1) and syt11 cDNAs were cloned into the pEGFP vector. Briefly, the full-length cDNAs of human syt1 and syt11 were obtained by polymerase chain reaction (PCR) from a human adult brain cDNA library cloned in the pGAD10 expression plasmid (Clontech) using primer pairs spanning the entire reading frame. Primers used for cloning human synaptotagmin I were: forward primer: TGGTGAGCGAGAGTCAC-CATGA (SEQ ID NO:11); reverse primers: B1, TTTCCTT-TACTTCTTGACG (SEQ ID NO:12) B2, TGAAGGACTTAGGGGCTCTCT (SEQ ID NO:13). Primers used for cloning human sytnaptotagmin XI: forward primer: GAGGGTTCCCAGAGCTGTCT (SEQ ID NO:14); reverse primer: CACATCCCTCCCCAGCTTG (SEQ ID NO:15). The human cDNA sequences of human synaptotagmin I and XI are shown in FIGS. 12A and 12C, respectively, as represented in GenBank accession numbers BC058917 (FIGS. 12A and 12B) and BC039205 (FIGS. 12C and 12D). All other expression plasmids were similarly constructed using specific PCR primer pairs. The mutant parkin cDNAs, parkinG289R and parkinC418R, were gifts from Professor Alexis Brice (INSERM U289, Hôpital de la Salpetriére, Paris, France).

For cell transfections, cells were plated 24 h prior to transfection. On the following day, cDNA plasmids were treated with polyfect transfectant reagent (Qiagen) and transfected into HEK293 cells according to the manufacturer's protocol. At the desired time point (24, 48, and 72 h) after transfection, cells were fixed for immunofluorescence labeling, or extracted for immunoprecipitation and western blots. For cells that were examined longer than 24 h after transfection, the media were changed once.

To perform in vitro co-immunoprecipitation experiments, HA-tagged parkin expression cDNAs (pCMV-HA-parkin, pCMV-HA-truncated parkins, pCMV-HA-parkin$^{C418R}$, pCMV-HA-parkin$^{G289R}$) were co-transfected with the respective GFP tagged fusion protein expression vectors (pEGFP-hsyt11AB, pEGFP-syt1, pEGFP-syt11, or pEGFP) into HEK293 cells grown in standard media conditions at 60-80% confluency in 100 mm$^2$ dishes. Controls were cells transfected only with the pCMV-HA-parkin or non-transfected cells. In certain experiments, β-actin antibody (Sigma; St. Louis Mo.) and β-COP antibody was used. The following reagents were purchased from Roche Diagnostics: mouse anti-HA, anti-HA-peroxidase, anti-myc-peroxidase, anti-HA-agarose. After 48 hours, proteins were extracted essentially as described in Example II with detergent buffer containing 0.5% NP40 and protease inhibitor mixture (Roche Molecular Biochemicals; Indianapolis Ind.). Protein extracts were immunoprecipitated (ip) with anti-GFP (Chemicon; Temecula CA), or rat anti-HA agarose matrix (Roche). Immunoprecipitation products were immunoblotted with anti-GFP antibody and anti-HA conjugated peroxidase.

FIG. 2C shows in vitro interaction of GFP-syt1 and syt11 with HA-parkin. Protein extracts from HEK293 cells overexpressing HA-parkin and the corresponding GFP fusion proteins were co-immunoprecipitated (co-IP) with a mouse anti-GFP antibody. The immunoprecipitation products were detected with rat anti-HA-peroxidase (top panel) and a rabbit anti-GFP antibody (bottom panel).

The pEGFP-syt1 and pEGFP-syt11 vectors were individually cotransfected with the pCMV-HA-parkin plasmid into 293T cells. The pEGFP plasmid was used as a vector control. After 24 hours, protein extracts were obtained and co-precipitated with mouse anti-GFP antibody to pull down GFP-fusion proteins. The co-IP products were immunoblotted with rabbit anti-GFP (FIG. 2C, bottom panel) or rat anti-HA-conjugated peroxidase (FIG. 2C, top panel). The anti-HA peroxidase detected the HA-parkin band only in samples with GFP-syt1 and GFP-syt11 but not in samples containing the GFP control, indicating that the HA-parkin specifically co-precipitated with the synaptotagmin fusion proteins but not with the GFP tag. Thus, both the syt1 and syt11 proteins co-precipitated parkin, but the GFP tag did not.

To account for the possibility that the large GFP tag might influence parkin and synaptotagmin interaction, the syt1 cDNA was transferred into the pCMV-myc expression plasmid. Co-immunoprecipitation of protein extracts from 293T cells coexpressing the HA-parkin and GFP-syt1 with anti-HA-agarose, followed by detection with anti-myc-conjugated peroxidase or anti-HA-conjugated peroxidase, found that the HA-parkin also co-precipitated with the myc-syt1. These observations indicate that the large GFP tag has no influence on the interaction between parkin and synaptotagmin. Therefore, GFP-tagged synaptotagmins were used for subsequent analyses.

To determine whether endogenous parkin interacts with synaptotagmins, in vivo co-immunoprecipitation experiments were performed in PC12 cells. PC12 cells were grown in DMEM containing 10% heat-inactivated serum, 5% fetal bovine serum, and penicillin/streptomycin in a 37° C. incubator with 10% $CO_2$. Media were changed every 3 days. PC12 cells were grown for 48 hours, and proteins were extracted in co-ip buffer (50 mM Tris-HCl, pH 7.5, 0.2% Triton X-100, 150 mM NaCl, and one protease inhibitor pellet (Roche) per 10 ml buffer). Protein extracts were precleared with mouse or rabbit IgG conjugated agarose and incubated with the respective antibodies overnight in the cold room. The primary antibodies were pulled down with anti-mouse or anti-rabbit IgG conjugate agarose for two hours. The final pellets were washed 7 times with co-ip buffer, and the coprecipitates were eluted from the secondary antibody-conjugated agarose with SDS-PAGE buffer. Co-ip products were immunoblotted with either anti-parkin or anti-syt antibodies.

FIG. 2D shows in vivo interaction of endogenous parkin with syt1 in PC12 cells. Co-ip of protein extracts from PC12 cells with 5 µl (lane 1) and 1 µl (lane 2) mouse anti-syt1, and 1 µl mouse IgG (lane 3). Co-IP products were detected with rabbit anti-parkin and mouse anti-syt1 antibodies simultaneously. Endogenous parkin was detected in the anti-syt1 immunoprecipitate, but not in the control immunoprecipitate using mouse IgG. Lane 4 shows a blot of the PC12 protein lysate.

Co-immunoprecipitation using mouse anti-syt1 antibody pulled down both syt1 and endogenous parkin (FIG. 2D). The mouse IgG failed to precipitate either the syt1 or parkin, suggesting the specificity of the endogenous co-ip. Co-ip using anti-parkin or anti-syt11 antibodies failed to co-precipitate parkin with syt11. The failure to find any endogeneous parkin-syt precipitate was likely a result of the insolubility of the endogenous syt11 in the buffer used for co-immunoprecipitation.

To determine whether parkin interacted with endogenous sytXI, protein extract from human cerebral cortex was immunoprecipitated with the anti-parka antibody. For co-immunoprecipitation of human brain extracts, a 1.4 g sample of human cerebral cortex was chopped into small pieces and resuspended in 7 ml of cold lysis buffer (100 mM Tris-HCl, pH 7.5, 150 mM NaCl, 1% Triton X-100, 0.05% SDS, 0.05% deoxycholic acid, and 1 protease inhibitor pellet/10 ml buffer). The cell suspension was homogenized by a glass homogenizer. Protein lysate was aliquoted into 1 ml aliquots and microfuged at top speed in the cold room. Protein extracts were precleared with rabbit IgG conjugated agarose and protein A conjugated agarose for 3 h at 4° C., and the precleared lysate was incubated with rabbit anti-parkA or mouse anti-sytXI antibody overnight in the cold room. The primary antibodies were pulled down with protein A conjugated agarose for 4 h at 4° C. The final pellets were washed five times with co-ip buffer, and the coprecipitates were eluted from the secondary antibody-conjugated agarose with SDS-PAGE buffer. Co-ip products were immunoblotted with either chick anti-parkA or anti-sytXIA antibody.

Following co-ip of human cerebral cortex extracts, the precipitate was then detected with either chick anti-parkA or antisytXIA antibody (FIG. 2E, lanes 1 and 2). The anti-parkA antibody detected a single parkin band in the anti-parka precipitate (FIG. 2E, lane 1, top panel), while the anti-sytXIA antibody detected the sytXI protein band (FIG. 2E, lane 1, bottom panel). When the same protein extract was coimmunoprecipitated with the anti-sytXI antibody, parkin was specifically coprecipitated with sytXI (FIG. 2E, lane 3). The absence of both the sytXI and the parkin bands in the control reactions (FIG. 2E, lanes 2 and 4) demonstrated the specificity of the parkin-sytXI interactions in the cells, confirming that endogenous parkin interacted with endogenous sytXI.

These results indicate that parkin interacts with synaptotagmins 1 and 11.

EXAMPLE IV

The RING2 Motif is Essential for Synaptotagmin Binding

These experiments describe characterization of the role of the RING motifs of parkin in synaptotagmin binding.

To determine which domain of parkin binds to synaptotagmin, several truncated parkins tagged with the HA epitope were constructed (FIG. 3A). The truncated parkin cDNA expression plasmids expressed sufficient truncated parkins for coexpression with GFP-syts (FIG. 3C). Each truncated construct was coexpressed with GFP-sytxI. After 24 h, protein extracts were immunoprecipitated with rat anti-HA-conjugated agarose followed by western blot detection with anti-GFP antibody. Truncated parkins lacking amino acid residues 204-293 (p1-203, p294-385, and p294-465) failed to interact with the full length synaptotagmin XI. The failure of these truncated parkins to interact with sytXI was not the result of decreased expression levels of the truncated parkins. Expression levels of the p1-203 and p294-465 parkins were much higher than the constructs that interacted with sytXI (FIG. 3C). Truncated parkins containing the whole or part of the p204-293 domain (p1-465, p1-314, p78-465, p78-238, p257-465) interacted with sytXI, all having different binding affinities (FIG. 3B). These observations indicate that amino acid residues 204-293, which contain the RING1 domain, are important for parkin interaction with sytXI.

Data from the binding assays suggest that there are at least two sytXI binding sites on parkin. The first binding site is located between amino acid residues 204 and 238. This was supported by the observation that the p78-238 peptide, which does not contain the RING1 domain, interacted with sytXI while the p1-203 peptide did not bind (FIG. 3). The second binding site is located within the RING1 domain between amino acid residues 257 and 293. This was supported by the observation that peptide p257-465 interacted with sytXI, whereas peptides p294-385 and p294-465 did not bind (FIG. 3). This observation was further supported by the effect of disease-causing amino acid substitutions in parkin. Parkin containing a missense mutation in the RING1 finger motif (parkinC289G) interacted weakly with sytXI (2.5-fold less) compared with parkinC418R (FIG. 3B). In addition, both mutated parkins fails to ubiquitinate sytXI (FIG. 4) although parkinC418R does not lose the ability to bind to sytXI (FIG. 3B).

Similar results were seen with other parkin truncation mutants having different boundaries, where the parkin binding site was mapped to the RING2 finger motif. Similar results were also observed for syt1.

These results indicate that the syt11 binding site maps to the RING finger motif.

EXAMPLE V

Ubiquitination of Synaptotagmins by Parkin

This example describes ubiquitination of synaptotagmins by parkin.

Parkin is an E3 ubiquitin ligase, an essential enzyme required for the ubiquitination of specific substrates targeted for degradation by the proteasome complex or the lysosome (Shimura et al., supra, 2000; Zhang et al., supra, 2000). To determine whether synaptotagmins are substrates of parkin, in vitro ubiquitination assays were performed as described by Zhang et al., *Proc. Natl. Acad. Sci. USA* 97:13354-13359 (2000), which is incorporated herein by reference. Briefly, HEK293 cells were transfected with 5 µg of PCMV-Myc-Ubiquitin, pEGFP-Syt1 or -Syt11, and different PCMV-HA-parkins (wild type, truncated, and missense). After 24 (or sometimes 36) hrs, cells were incubated in normal media containing 20 µM lactacystin or 20 µM proteasome inhibitor I for 4 hrs. Cells were washed with cold DPBS.

For ubiquitination assays, cells were extracted with triple detergent buffer (20 mM Hepes, pH 7.2, 150 mM NaCl, 1% Triton X-100, 0.1% SDS, 0.5% deoxycholate). Proteins were extracted: with RIPA buffer containing protease inhibitor pellet (Roche, 1 pellet per 10 ml buffer), and 2 µM N-ethylamimide to inhibit deubiquitination enzymes. Protein extracts were immunoprecipitated with mouse antiGFP antibody, and the IP products were detected with anti-HA, anti-myc, and rabbit anti-GFP.

In the ubiquitination experiments, HEK 293 cells were cotransfected with HA-tagged or control parkin cDNA plasmids and myc-tagged ubiquitin, with either GFP-tagged syt1 or GFP-tagged syt11 (FIG. 4). GFP was used as a negative control for substrate specificity, while truncated HA-tagged parkin proteins (p78-465, p1-203, p294-385, p294-465 in FIGS. 4A-C)(p1-314 and p77-465 in FIGS. 4D-F) were used as negative controls for the wild type parkin. HEK293 cells overexpressing HA-parkins and the corresponding myc-ubiquitin and GFP-tagged proteins were treated with lactacystin for 4 hours, and protein extracts were immunoprecipitated with anti-GFP antibody. Products of the ubiquitination assays for syt1 were detected in FIG. 4D with antibodies to myc- (top), GFP-(middle), and HA-tags (bottom). For detection of parkin ubiquitination of syt11 as shown in FIG. 4E, western blots were detected with anti-myc (top) and anti-GFP (bottom) antibodies. In both assays, cells co-expressing GFP-syt1 and HA-parkin formed more ubiquitin-conjugated syt1 complexes than cells expressing HA-parkin and the controls. Note the lack of ubiquitinated products in cells expressing HA-parkin and GFP and in other negative controls.

As shown in FIG. 4, when cells were incubated with lactacystin, an inhibitor of the proteasome complex, cells expressing the wild type parkin and GFP-syt11 (FIG. 4A-C and E) or GFP-syt1 (FIG. 4D) showed an accumulation of ubiquitin-synaptotagmin conjugates above background controls. Wild type parkin had no effect on the polyubiquitination of the GFP tag. Truncated parkins showed little effect on the levels of ubiquitinated synaptotagmin conjugates, although one of the peptides (p78-465) could bind to synaptotagmins (FIG. 3), and the levels of expression of the truncated parkins were high compared with the wild type parkin. The presence of ubiquitin-conjugated syt found in cells co-expressing only GFP-syt and myc-ubiquitin was likely a result of the presence of endogenous parkin in HEK293 cells. The pattern of ubiquitinated syts indicated the presence of a variety of species containing ubiquitin chains of different lengths.

To determine whether disease-associated point mutations affected the ability of parkin to ubiquitinate syts, ubiquitination assays were also performed for missense mutated parkin$^{C289G}$ and parkin$^{C41BR}$. Both mutant parkins produced undetectable levels of ubiquitinated sytXI compared with the wild-type parkin (FIG. 4). Under longer exposure, all truncated and missense mutated parkin transfected cells produced weak levels of ubiquitin-conjugated sytXI comparable to cells transfected with only GFP-sytXI, but the levels of the ubiquitinated sytXI were significantly lower than those produced by wild-type parkin. This background level of ubiquitinated sytXI was probably produced by endogenous parkin or by an unidentified E3 ubiquitin ligase in HEK293 cells and is consistent with observations by other investigators using HEK293 cells (Ren et al., *J. Neurosci.* 23:3316-3324 (2003)). In both co-ip (FIG. 3) and ubiquitination (FIG. 4) experiments, a majority of mutant parkins could be detected in the pellet fractions that were dissolved in the SDS-PAGE sample buffer.

Western blot analysis of the same protein samples with an anti-GFP antibody detected a high MW GFP-sytXI band near the top of the well loaded with the parkin-sytXI co-expressed sample (FIG. 4). This band was likely the insoluble ubiquitinylated sytXI complex since the anti-myc antibody also strongly detected the same complex. This band was faintly observed in the controls. The smaller MW ubiquitinylated sytXI species were undetectable by the antiGFP antibody. These findings are consistent with ubiquitinylation experiments of α- and β-tubulin (Ren et al., supra, 2003) and synphilin-1 (Chung et al., *Nat. Med.* 7:1144-1150 (2001)) in HEK293 cells. In these experiments, the ubiquitinylated substrates were undetectable by the antibodies against the respective proteins, but the antibodies against ubiquitin or its tag strongly detected the respective parkin-mediated ubiquitinylated substrates.

Similar results were also found for syt1. As shown in FIG. 4F, mutated parkins, C289G and C418R, exhibited reduced ubiquitination of syt1 and syt11. Cells expressing parkin mutants and GFP-syt1 or 11 produce a lower amount of ubiquitin-conjugated syt. Note the weak ubiquitination of syt11 by mutant C289G. Thus, the parkin$^{C289G}$ mutant inhibits the ubiquitination of syt1 but weakly ubiquitinates syt11. In contrast, the parkin$^{C418G}$ mutant inhibits the ubiquitination of both syt1 and 11 equally. The ubiquitination patterns in cells coexpressing the mutant parkins and syts were weaker than in cells expressing wild type parkin and syts (FIG. 4F, top panel). Western blots of the protein extracts from cells expressing parkin and syts and treated with lactacystin for 4 hours detected a low amount of the mutants compared to the wild type parkin (FIG. 4F). The mutant parkin was found abundantly in the insoluble pellet (FIG. 4F).

Since parkin-mediated ubiquitinylated substrates undergo degradation by the proteasome-dependent pathway (Zhang et al., *Proc. Natl. Acad. Sci. USA* 97:13354-13359 (2000); Imai et al., *Cell* 105:891-902 (2001); Imai et al., *Mol. Cell.* 10:55-67 (2002); Ren et al., *J. Neurosci.* 23:3316-3324 (2003); Corti et al., *Hum. Mol. Genet.* 12:1427-1437 (2003); Engelender et al., *Nat. Genet.* 22:110-114 (1999)), pulse-chase experiments were performed to determine the turnover of GFP-sytXI in HA-vector and HA-parkin$^{1-465}$ transfected HEK293 cells. To determine whether parkin accelerates GFP-sytXI degradation, HEK293 cells were co-transfected with GFP-sytXI and HA-vector or GFP-sytXI and HA-parkin plasmids. After 24 h, cells were washed once with DMEM containing 5% dialyzed FBS and no Met and Cys amino acids. Cells were incubated in this media for 30 min, and grown in the same media containing 100 µCi/ml of $^{35}$S-Met/Cys (EXPRE$^{31}$S$^{35}$S ($^{35}$S) Protein Labeling Mix, Amersham) for 30 min. Cells were then chased at the indicated time points. Protein extracts were isolated using RIPA buffer (20 mM HEPES, pH 7.5, 15.0 mM NaCl, 0.1% SDS, 0.5% deoxycholate, 1% Triton-X100, 1 mM EDTA, protease mixture pellet). GFP-sytXI was immunoprecipitated with rabbit anti-GFP antibody (CHEMICON; Temecula CA) as described above.

Figures 5A, 5B:
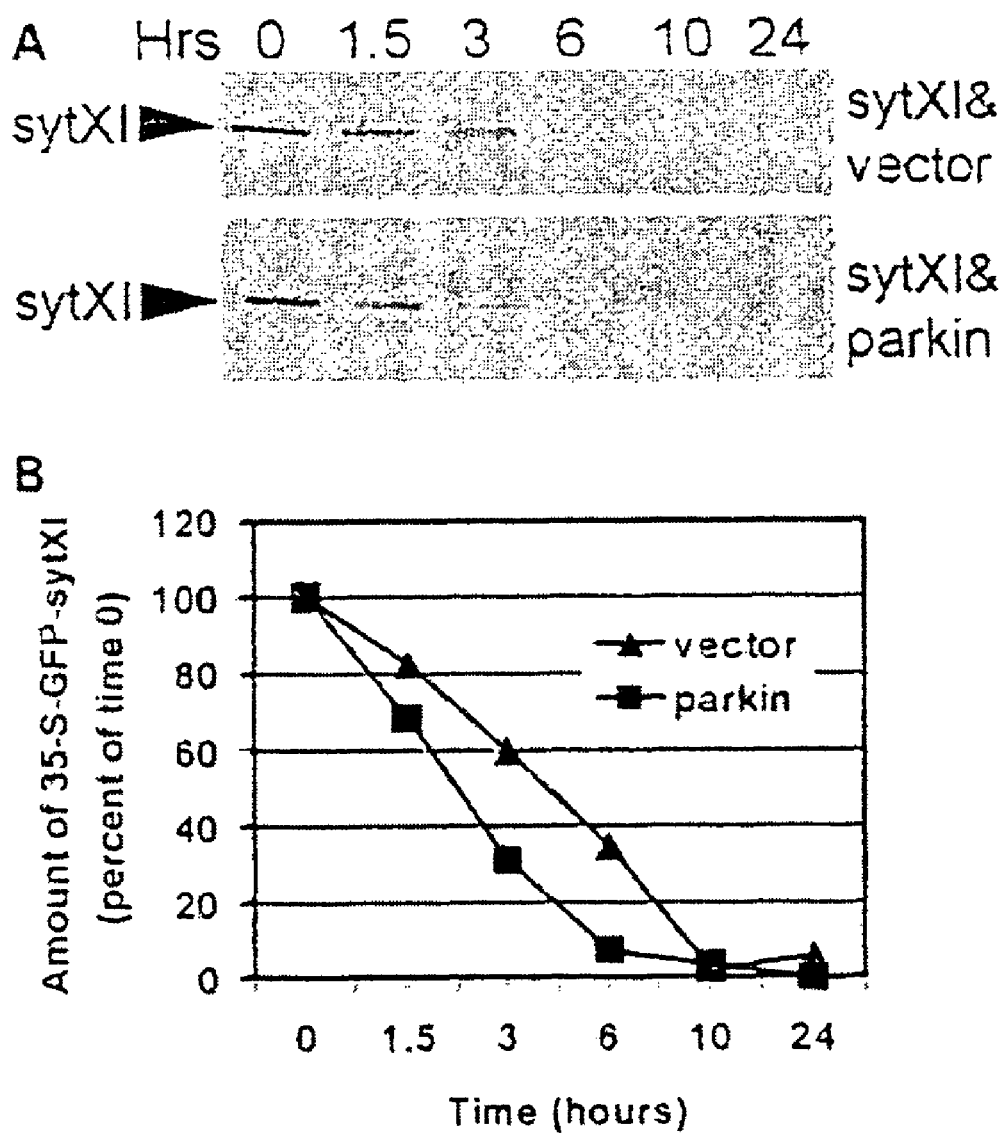
FIGS. 5A and B show that parkin accelerates the turnover of GFP-sytXI. Pulse-chase analysis of the degradation of GFP-sytXI in HEK293 cells expressing either HA-vector or HA-parkin at 0, 1.5, 3, 6 and 24 h was performed, and GFP-sytXI was immunoprecipitated with anti-GFP antibody. The immunoprecipitates were analyzed by gel electrophoresis (FIG. 5A) and quantified (FIG. 5B). Data are from one of two independent experiments. The second experiment had an even stronger parkin effect.

Parkin increased the degradation of GFP-sytXI in HA-parkin$^{1-465}$ transfected HEK293 cells (FIG. 5). Approximately 40% of newly synthesized GFP-sytXI was degraded after 1.5 h chase in HA-parkin$^{1-465}$ expressing cells, whereas it took 3 h to degrade the equivalent amount of GFP-sytXI in HA-vector transfected cells.

These results demonstrate that parkin ubiquitinates both syt1 and 11.

EXAMPLE VI

Parkin Colocalizes with Synaptotagmins and Recruits Synaptotagmins to Perinuclear Complexes This example describes the cellular location of parkin and synaptotagmins.

The interaction of two proteins is likely to be physiologically relevant if they occupy the same subcellular compartment. To investigate parkin-syt co-localization, immunofluorescence experiments were performed. Briefly, for COS1 cell cultures, COS1 cells were grown in DMEM medium supplemented with 10% FBS and penicillin/streptomycin, in 37° C. incubator with 5% $CO_2$. Media were changed every 3 days. One day prior to transfection, 50,000 cells were seeded in a 1 cm coverslip previously coated with 20 µg/ml collagen IV. PC12 cells were grown as described in Example III.

Immunofluorescent labeling and confocal laser microscopy was performed as follows. Cells were fixed with 4% paraformaldehyde in DPBS for 20 min on ice, and incubated in solution A (DPBS, 3% goat serum, 0.05% Triton X-1000) for 30 minutes. Cells were then incubated with selected mouse or rabbit primary antibody diluted in solution A for 1 hr at room temperature. Cells were then washed 5 times with cold DPBS and incubated with the corresponding secondary antibody conjugated to either fluorescein isothiocyanate (FITC) or tetramethylrhodamine isothiocyanate (TRITC) diluted in solution A for 1 hr at room temperature. Cells were then again washed 5 times with cold DPBS and covered with a slide in 80% glycerol and 10 mM sodium gallate for fading protection. Cells were viewed with a Leica TCSSP (true confocal scanner spectrophotometry) microscope through the oil immersion 100× lens. Images were acquired sequentially to prevent bleaching between FITC or GFP with TRITC fluorescence.

To investigate parkin-syt co-localization, PC12 cells were induced with NGF for 7 days. PC12 cells were induced with 50 ng/ml NGF for 7 days, and immunofluoroscently co-labeled with antibodies to rabbit parkin (stained red, FIG. 6P) and mouse syt1 (stained green, FIG. 6Q), or chicken parkin (stained green, FIG. 6A) and rabbit-syt11 (stained red, FIG. 6D). Images were acquired by Leica TCSSP microscopy using a 100× oil immersion lens. Stacked images were merged (FIGS. 6C and 6R). Yellow color of the merged images indicates colocalization of two proteins. Inserts in FIGS. 6A-C and P-R are from the cell body of the same cell from which the long neurite arises (shown at lower magnification). Parkin and syt colocalize in the perinuclear area and boutons (arrows) along the neurite.

The NGF-induced PC12 neurons were co-labeled with antibodies to rabbit parkin and mouse syt 1 (FIGS. 6P-R), or chick parkin and rabbit syt 11 (FIGS. 6A-C). Parkin colocalized with both syt1 and syt11 at positions around the nuclear membrane (FIG. 6R, lower arrow) and at boutons (FIGS. 6C and 6R, white arrows) along the neurites. Parkin or GFP-syt present in other regions of the cell did not colocalize. These results indicate that endogenous parkin colocalizes with endogenous syt1 and syt11 in PC12 cells.

To investigate the effect of parkin on the distribution and levels of synaptotagmin, HEK293 were co-transfected with both the GFP-syt and HA-parkin vectors. After 36 hours, cells were labeled with anti-HA antibody.

Figure 7:
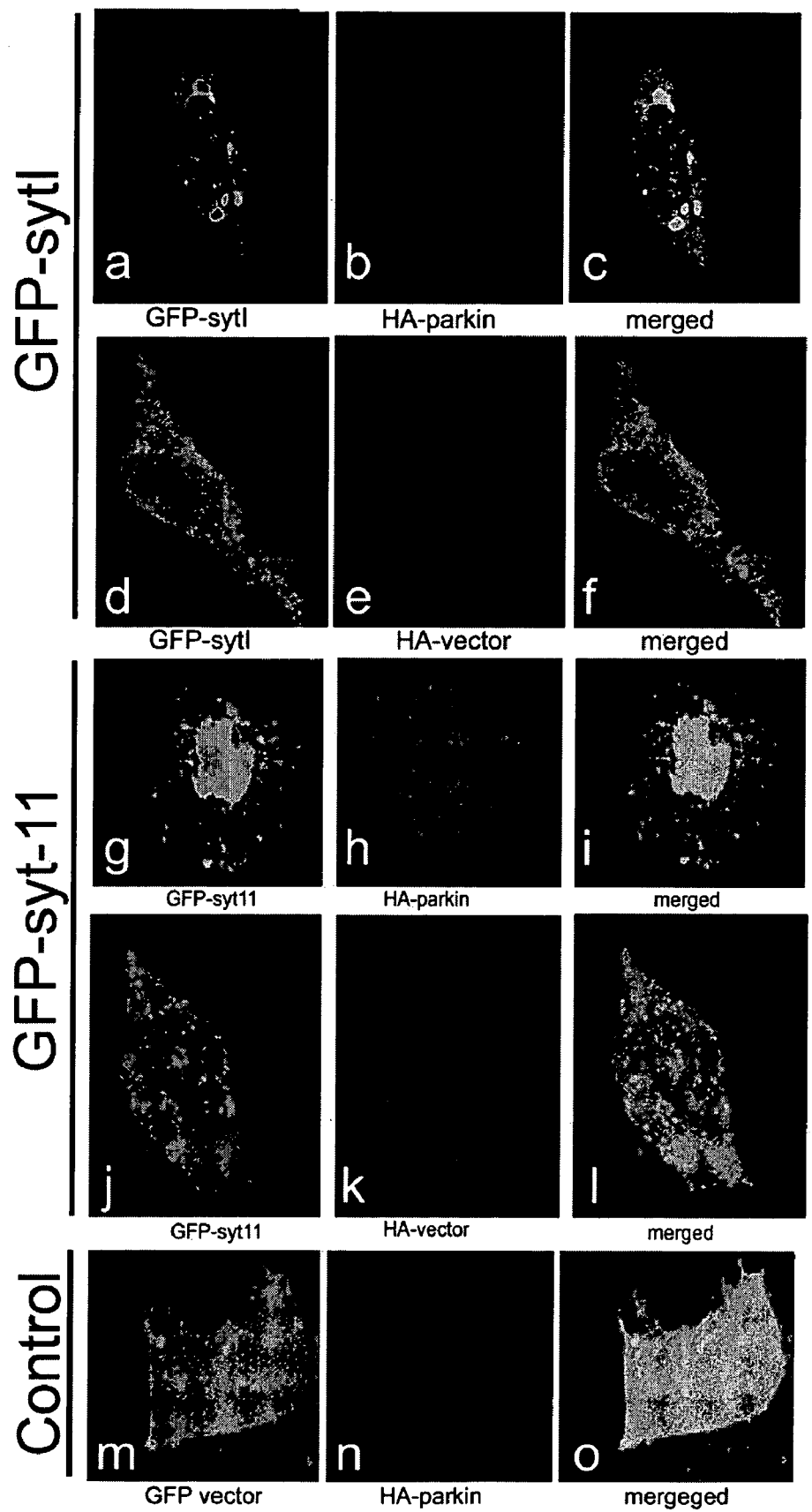
FIGS. 7A-O shows immunofluorescence of HEK293 cells, which were co-transfected with GFP-syt1 and HA-parkin (FIGS. 7A-C), GFP-syt1 and HA-vector (FIGS. 7D-F), GFP-syt11 and HA-parkin (FIGS. 7G-I), GFP-syt11 and HA-vector (FIGS. 7J-L), or GFP-vector and HA-parkin (FIGS. 7M-O). Transfected cells were labeled with anti-HA, and images were acquired by the Leica TCSSP using the 100× oil immersion lens.

Cells were co-transfected with GFP-syt1 and HA-parkin (FIGS. 7A-C), GFP-syt1 and HA-vector (FIGS. 7D-F), GFP-syt11 and HA-parkin (FIGS. 7G-I), GFP-syt11 and HA-vector (FIGS. 7J-L), or GFP-vector and HA-parkin (FIGS. 7M-O). Transfected cells were labeled with anti-HA, and images were acquired by the Leica TCSSP using the 100× oil immersion lens. Note the difference of colocalization of parkin with syt1 and syt11.

In HEK293 cells co-expressing both parkin and syt, HA-parkin and GFP-syt colocalized in aggregates adjacent to the perinuclear membrane (FIGS. 7A-C, 7G-I). In these cells, the levels of GFP-syt were much lower compared to the controls. In the controls, where HEK293 cells were cotransfeced with only the GFP-syt and HA vector, GFP-syt was found distributed throughout the cells in cytoplasmic vesicles. Likewise, when HA-parkin was expressed with GFP, it was diffusely distributed throughout the cells (FIGS. 7M-O).

These results indicate that parkin colocalizes with syts in cotransfected HEK293 cells and alters their normal cellular distribution.

EXAMPLE VII

SytXI is Localized in the Cell Bodies and Neurites of Human Substantia Nigra Neurons The death of substantia nigra neurons and the formation of Lewy bodies are hallmarks of many forms of PD, and some constituent proteins of Lewy bodies are mutated in inherited forms of PD. To establish a potential link between sytXI and parkin in the pathogenesis of neurodegeneration in classic PD, immunohistochemical labeling of substantia nigra sections from two normal and two sporadic PD patients was performed using antibodies to sytXI (anti-sytXIA), parkin and ubiquitin.

For immunohistochemical labeling of human substantia nigra sections, human brain 7 µm sections were stained with rabbit antisytXIA (10 µg/ml), parka (5 µg/ml), ubiquitin (1/500) antibodies using the immunohistochemical labeling protocols described in Huynh et al. (*Ann. Neurol.* 48:737-744 (2000)). Briefly, brains sections were deparafinized and demasked by Biomedia's Autozyme solution (Fisher). Sections were then blocked with 3% normal goat serum and incubated with the primary antibody overnight in the cold room. The next day, sections were developed using the Elite Vector ABC kit (Vector, San Diego, Calif., USA), and the Biomedia's diaminobenzidene substrate kit (Fisher). For peptide preabsorption, 10 µg of anti-sytXIA antibody were preincubated with 1000-fold sytXIA peptide overnight in the cold room. The next day, the preincubated antibody was microfuged for 10 min and diluted in 1 ml of the staining buffer. Images were acquired using the 20× and 63× oil immersion lenses and captured by a SPOT digital camera.

As shown in FIG. 6D-O, the normal human substantia nigra neurons were strongly stained by antibodies to sytXI and parkin. The anti-sytXIA antibody labeled both the cell bodies and neurite extensions of the nigral neurons (FIGS. 6D, G and J), similar to the anti-parka antibody (FIGS. 6F, I and L). The sytXI immunoreactivities were specific, since anti-sytXIA preabsorbed with the sytXIA peptide failed to label the nigral neurons (FIGS. 6E, H and K).

FIGS. 6M-O depict the immunohistochemical labeling of a nigral neuron from an individual with sporadic PD. The anti-sytXIA antibody labeled the core of the intracellular Lewy bodies (LBs; FIG. 6N, black arrow) similar to the anti-ubiquitin antibody (FIG. 6M). The sytXI LBs staining was weak compared with ubiquitin staining; of note is the strong labeling of the neuropil. This labeling was specific since anti-sytXIA antibody preabsorbed with the sytXIA peptide failed to label the Lewy body or the neuropil (FIG. 6O, black arrow). As reported previously (Huynh et al., *Ann. Neurol.* 48:737-744 (2000)), the Lewy bodies in these two sporadic PD brains did not stain with the anti-parka antibody.

These results show that sytXI is localized in the cell bodies and neurites of human substantia nigra neurons.

EXAMPLE VIII

Identification and Characterization of a Parkin-Interacting Polypeptide

This example describes the identification of a parkin-interacting polypeptide.

A yeast two-hybrid screen was performed as described in Example I. Briefly, to identify CNS proteins that interact with parkin, a yeast two-hybrid assay was performed on $1 \times 10^6$ independent yeast colonies from a human brain cDNA library. The screen used full length parkin as bait. Subsequent screening with yeast filter and liquid assays confirmed that the clone was positive.

Nucleotide sequencing showed that one clone identified in the yeast two-hybrid screen encoded the N-terminal domain of a small, novel synapsin-like protein (SLP). The sequence of the polypeptide is shown in FIG. 8.

Figure 9:
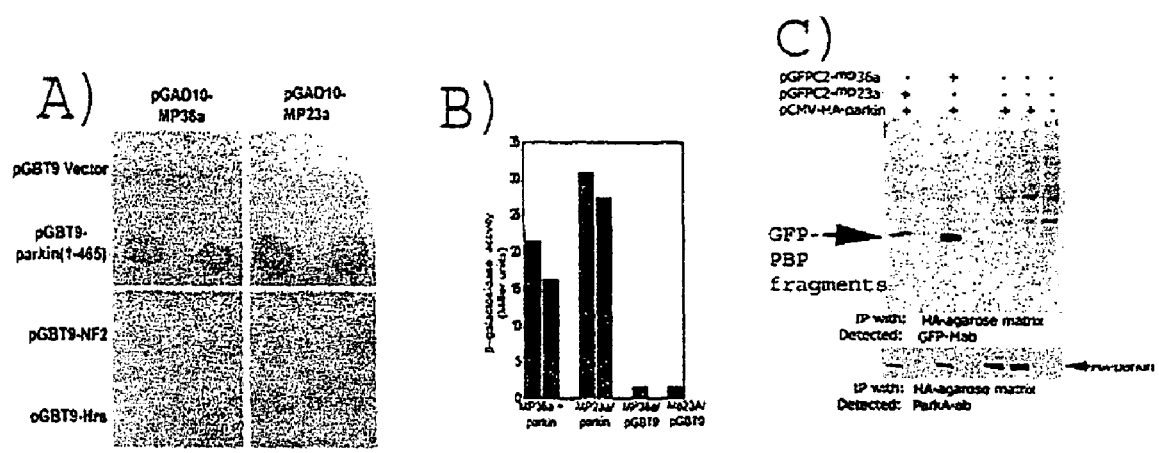
FIG. 9A shows a yeast two-hybrid filter binding assay with detection of β-galactosidase.
FIG. 9B shows a yeast two-hybrid liquid assay with detection of β-galactosidase.
FIG. 9C shows co-immunoprecipitation of MP36a and MP23a GFP fusions with HA-parkin. Immunoprecipitation was performed with HA-agarose matrix. MP36a and MP23a GFP fusions were detected with GFP antibody (upper panel), and parkin was detected with ParkA antibody (lower panel).
FIG. 9D shows co-immunoprecipitation of endogenous parkin with SLP in PC12 cells. Protein extracts were immunoprecipitated with rabbit anti-parkA or rabbit IgG control. IP products were immunoblotted with chick anti-parkin antibody (left), or rabbit anti-SLP (right). The anti-parkA antibody detected a 50 kDa parkin band in the anti-parkA co-ip. This band was absent in the chick IgG ip sample. The anti-SLP antibody detected a band at the predicted size of 36 kDa in the anti-parkA immunoprecipitated and the PC12 protein extract, but not in the sample precipitated with rabbit IgG, indicating that endogenous parkin co-precipitated native SLP.

As shown in FIG. 9A, both the MP36a and MP23a forms, also referred to as synapsin-like protein (SLP), interacted with parkin in the yeast filter assay. No binding was observed with the negative control plasmids pGBT9 vector, pGBT9-NF2, and pGBT9-Hrs. The binding with parkin was confirmed using liquid culture assays as described in Example I. As shown in FIG. 9B, MP36a and MP23a exhibited about 20-fold and 30-fold higher β-alactosidase activity in the presence of parkin, respectively, than with the negative control vector pGBT9.

To further test for interaction, co-immunoprecipitation experiments were performed as described in Example III. For co-immunoprecipitation experiments, constructs were generated as GFP fusions. Co-immunoprecipitation experiments showed that the full length protein interacted with parkin. Cells were transfected with the respective plasmids, as indicated in FIG. 9C. Co-immunoprecipitation of protein extracts from cells expressing HA-parkin and MP36a or MP23a GFP fusions were performed with HA-agarose, and the position of the respective GFP fusion proteins was determined by western blotting with GFP antibody. As shown in FIG. 9C, both MP36a and MP23a co-immunoprecipitated with parkin.

Figure 9D:
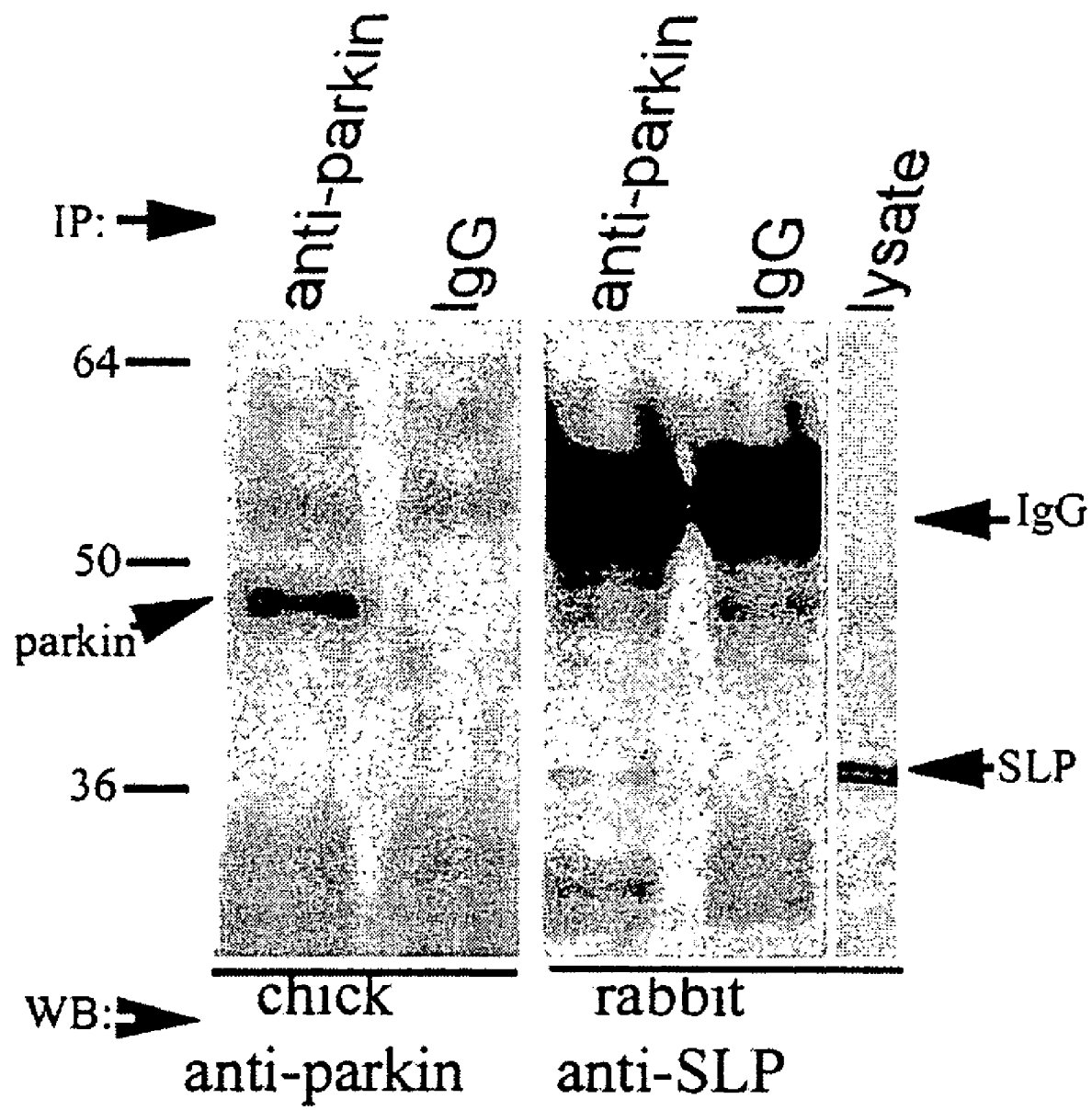

To determine whether endogenous parkin could bind to native SLP, co-immunoprecipitation experiments were performed in PC12 cells. Protein extracts were immunoprecipitated with rabbit anti-parkA or rabbit IgG control (FIG. 9D). IP products were immunoblotted with chick anti-parkin antibody (left), or rabbit anti-SLP (right). The anti-parkA antibody detected a 50 kDa parkin band in the anti-parkA co-ip. This band was absent in the chick IgG immunoprecipitate sample. The anti-SLP antibody detected a band at the predicted size of 36 kDa in the anti-parkA immunoprecipitate and the PC12 protein extract, but not in the sample precipitated with rabbit IgG, indicating that endogenous parkin co-precipitated native SLP.

Figure 10:
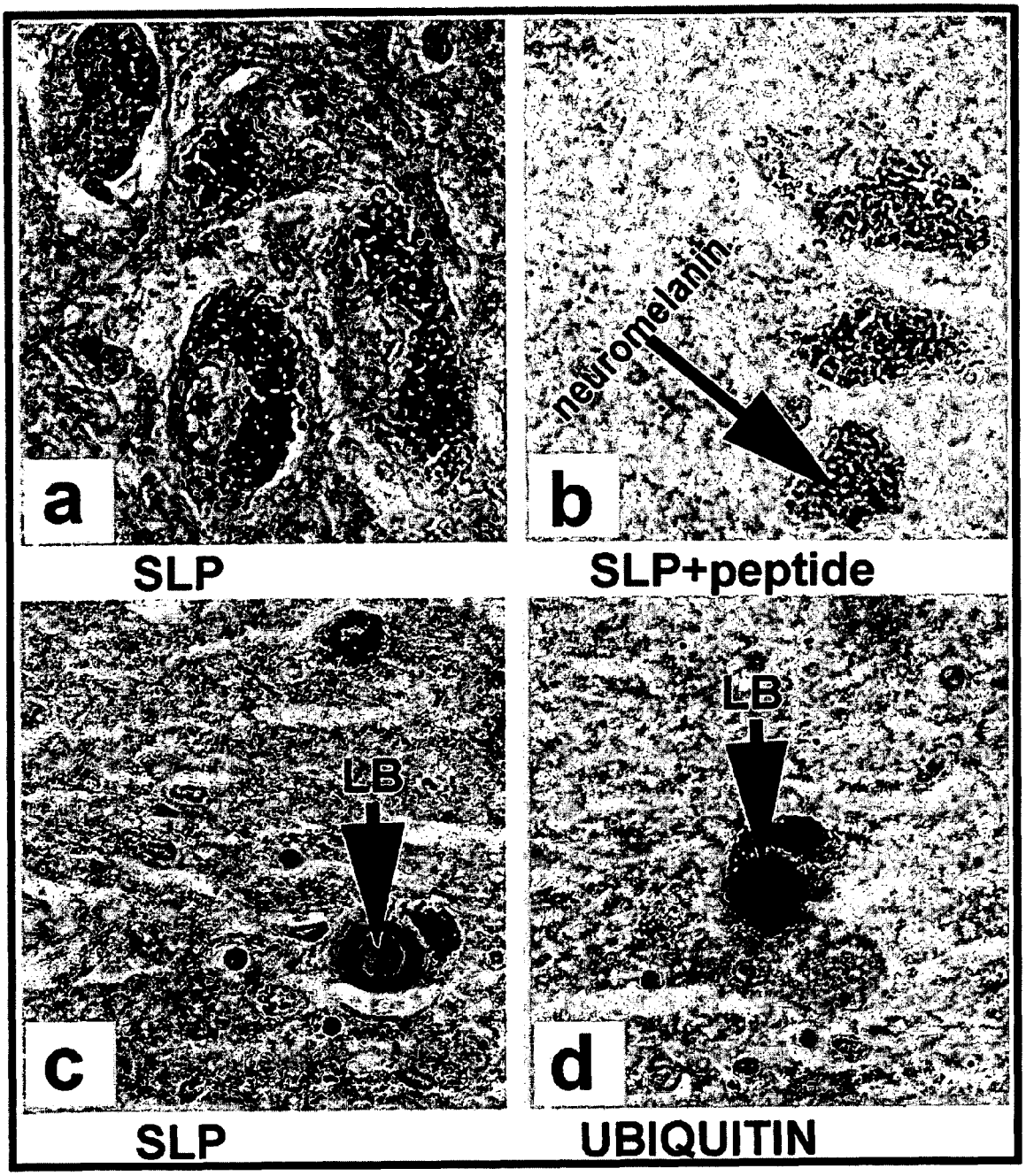
FIGS. 10A-D show expression of SLP and ubiquitin in human substantia nigra. Substantia nigra compacta sections were immunohistochemically stained with 10 μg/ml of affinity purified anti-SLP (FIGS. 10A and C), anti-SLP+SLP peptide (FIG. 10B), anti-ubiquitin (FIG. 10D) antibodies. The primary antibodies were detected using the Vector Elite Vectastain Rabbit ABC kit, and visualized with DAB. All sections were processed and stained identically. Both anti-SLP and anti-sytXI antibodies strongly labeled the neurites of neurons in the substantia nigra compacta. The anti-SLP antibody preabsorbed with the SLP peptide failed to react, indicating the specificity of the immunohistochemical labeling. The dark brown staining seen in the cell bodies is neuromelanin found in dopaminergic neurons.

The expression of SLP in human substantia nigra was also tested (FIG. 10). Substantia nigra compacta sections were immunohistochemically stained with 10 μg/ml of affinity purified anti-SLP (FIGS. 10A and C), anti-SLP+SLP peptide (FIG. 10B), anti-ubiquitin (FIG. 10D) antibodies. The primary antibodies were detected using the Vector Elite Vectastain Rabbit ABC kit, and visualized with 3,3'-diaminobenzidine (DAB). All sections were processed and stained identically. Both anti-SLP and anti-sytXI antibodies strongly labeled the neurites of neurons in the substantia nigra compacta. The anti-SLP antibody preabsorbed with the SLP peptide failed to react, indicating the specificity of the immunohistochemical labeling. The dark brown staining seen in the cell bodies is neuromelanin found in dopaminergic neurons. FIGS. 10C and D show the labeling of Lewy bodies (LBs) with anti-SLP (FIG. 10C) and anti-ubiquitin (FIG. 10D) antibodies.

Figure 11:
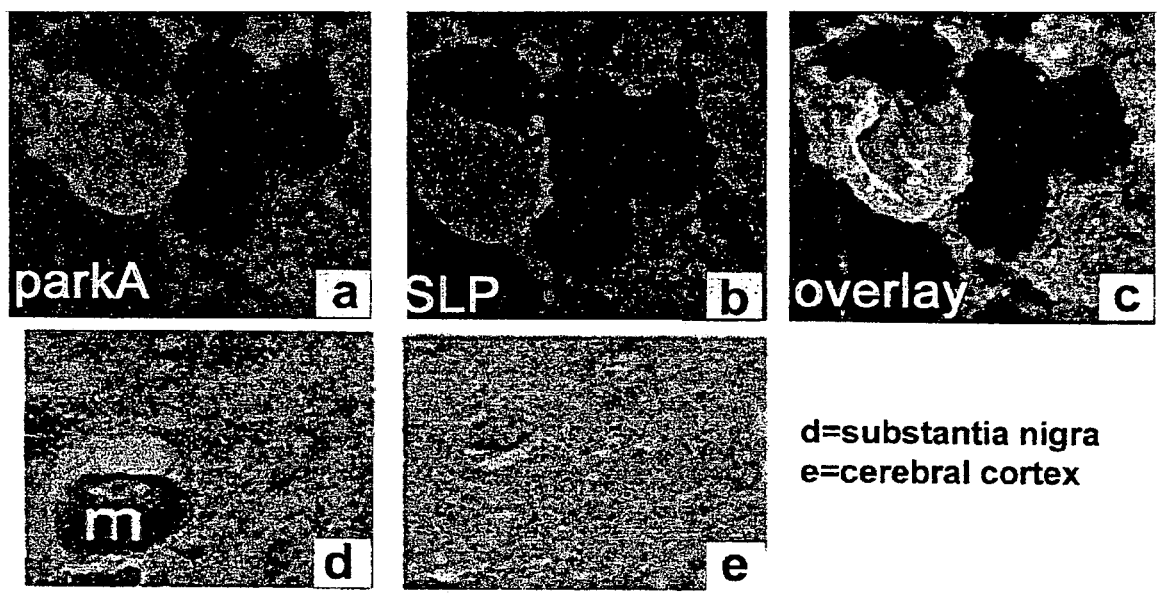
FIGS. 11A-C show immunofluorescence of cells showing the location of parkin and SLP. Cells were co-stained with parkin antibody (stained green, FIG. 11A) and SLP (stained red, FIG. 11B). The overlay image is shown in FIG. 11C, with yellow indicating co-localization of parkin and SLP.
FIGS. 11D and 11E show staining of the substantia nigra and cerebral cortex, respectively.

Colocalization of parkin and SLP was determined essentially as described in Example VI. Cells were co-labelled with parkin antibody (stained green, FIG. 11A) and antibody recognizing SLP (stained red, FIG. 11B). The overlay image indicates that parkin and SLP co-localize (stained yellow, FIG. 11C). Confocal immunofluorescence studies of NGF-induced PC12 neurons confirmed that both SLP colocalized with parkin at synaptic boutons. FIGS. 11D and 11E show staining of the substantia nigra and cerebral cortex, respectively. Ubiquitination experiments are performed as described in Example V.

These results indicate that SLP is a parkin binding protein that co-localizes with parkin in vivo. These results also indicate that SLP localizes to Lewy bodies, the pathologic hallmark of idiopathic PD, indicating that SLP can function in pathogenesis of PD, either directly (by mutation) or indirectly (by depletion).

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of identifying a candidate drug for treating Parkinson's disease, comprising contacting a parkin binding polypeptide selected from synaptotagmin I and synaptotagmin XI with one or more compounds and identifying a compound that alters the binding and/or colocalization of said parkin binding polypeptide with parkin.

2. The method of claim 1, wherein said compound decreases the binding and/or colocalization of said parkin binding polypeptide with parkin.

3. The method of claim 1, wherein said parkin binding polypeptide is synaptotagmin I.

4. The method of claim 1, wherein said parkin binding polypeptide is synaptotagmin XI.

* * * * *